United States Patent [19]
Bennett et al.

[11] Patent Number: 6,096,722
[45] Date of Patent: *Aug. 1, 2000

[54] ANTISENSE MODULATION OF CELL ADHESION MOLECULE EXPRESSION AND TREATMENT OF CELL ADHESION MOLECULE-ASSOCIATED DISEASES

[75] Inventors: C. Frank Bennett, Carlsbad, Calif.; Christopher K. Mirabelli, Dover, Mass.; Brenda Baker, Carlsbad, Calif.

[73] Assignee: Isis Pharmaceuticals Inc., Carlsbad, Calif.

[*] Notice: This patent is subject to a terminal disclaimer.

[21] Appl. No.: 09/085,759

[22] Filed: May 27, 1998

Related U.S. Application Data

[63] Continuation-in-part of application No. 08/440,740, May 12, 1995, Pat. No. 5,843,738, which is a continuation-in-part of application No. 08/063,167, May 17, 1993, Pat. No. 5,514,788, which is a continuation of application No. 07/969,151, Feb. 10, 1993, abandoned, which is a continuation-in-part of application No. 08/007,997, Jan. 21, 1993, Pat. No. 5,591,623, which is a continuation-in-part of application No. 07/939,855, Sep. 2, 1992, abandoned, which is a continuation-in-part of application No. 07/567,286, Aug. 14, 1990, abandoned.

[51] Int. Cl.$^7$ .......................... C07H 21/02; C07H 21/04; A61K 48/00
[52] U.S. Cl. .......................... 514/44; 536/23.1; 536/24.5; 435/6; 435/91.1; 435/325; 435/375
[58] Field of Search ................................. 435/91.1, 93.1, 435/375, 6, 325; 536/24.5, 23.1, 23.2, 24.3; 514/44

[56] References Cited

U.S. PATENT DOCUMENTS

| | | | |
|---|---|---|---|
| 5,514,788 | 5/1996 | Bennett et al. | 536/23.1 |
| 5,591,623 | 1/1997 | Bennett et al. | 435/375 |
| 5,789,573 | 8/1998 | Baker et al. | 536/24.5 |
| 5,843,738 | 12/1998 | Bennett et al. | 435/375 |

FOREIGN PATENT DOCUMENTS

WO 91/16900  11/1991  WIPO.

OTHER PUBLICATIONS

Andrea D. Branch, A good antisense molecule is hard to find, TIBS, 47–48, Feb. 1998.
Trisha Gura, Antisense Has Growing Pains, Science, pp. 575–577, Oct. 1995.
Stanley Crooke, Antisense '97: A roundtable on the state of the industry, Nature Biotechnology, p. 522, Jun. 1997.
Stanley Crooke, Antisense Research and Applications, Chapter 1, Basic Principles of Antisense Therapeutics, Springer–Verlag Press, Berlin, Heidelberg, New York, p. 3, Jul. 1998.
Wegner et al., "Intercellular Adhesion Molecule–1 (ICAM–1) in the Pathogenesis of Asthma", Science 1990, 247, 456–459.
Cosimi et al., "In Vivo Effects of Monoclonal Antibody To ICAN–1 (CD54) In Nonhuman Primates With Renal Allografts [1]", J. Immunol. 1990 144, 4604–4612.
Isobe et al., "Specific Acceptance of Cardiac Allograft After Treatment with Antibodies to ICAM–1 and LFA–1", Science 1992, 255, 1125–1127.
Marlin, et al., "A soluble form of intercellular adhesion molecule–1 inhibits rhinovirus infection", Nature 1990, 344, 70–72.

*Primary Examiner*—George C. Elliott
*Assistant Examiner*—Janet Epps
*Attorney, Agent, or Firm*—Law Offices of Jane Massey Licata

[57] ABSTRACT

Compositions and methods are provided for the modulation of expression of cellular adhesion molecules. In accordance with preferred embodiments, oligonucleotides are provided which are specifically hybridizable with nucleic acids encoding intercellular adhesion molecule-1, vascular cell adhesion molecule-1, and endothelial leukocyte adhesion molecule-1. Methods of modulating expression of cellular adhesion molecules are provided, as are methods of treating conditions associated with cellular adhesion molecules. In a preferred embodiment, the cellular adhesion molecule is ICAM-1, and a preferred antisense sequence targeted to human ICAM-1 is demonstrated to have clinical utility in several disease indications.

22 Claims, 25 Drawing Sheets

FIG. 1A

```
                GCTATAAGGA TCACGCGGCCC CAGTCGACGC TGCTACTCAG AGTTGCAACC TCAGCCTCGCT

ATG GCT CCC AGC AGC CCC CGG GCA CTG CCC GCT CTG TTC CCA
MET ALA PRO SER SER PRO ARG ALA LEU PRO ALA LEU PHE PRO

GGA CCT GGC AAT GCC CAG ACA TCT GTG TCC CCC CGG GGA TCC GTG
GLY PRO GLY ASN ALA GLN THR SER VAL SER PRO ARG GLY SER VAL

CTG GTG ACA TGC AGC ACC TCC GAC CAG CCC ATC CTG CCC TTG CCT AAA
LEU VAL THR CYS SER THR SER ASP GLN PRO ILE LEU PRO LEU PRO LYS

AAG GAG TTG CTC CTG CCT GGG AAC AAC CGG AAG GTG TTG GGC ATA CAA GAA GAT AGC
LYS GLU LEU LEU LEU PRO GLY ASN ASN ARG LYS VAL LEU GLY ILE GLN GLU ASP SER

CAA CCA ATG TGC TAT TCA TAC AAC TGC CCT GAT GGG CAG TCA ACA AAA GCT AAG TTC CTC ACC GTG TAC
GLN PRO MET CYS TYR SER TYR ASN CYS PRO ASP GLY GLN SER THR LYS ALA LYS PHE LEU THR VAL TYR

TGG ACT CCA GAA CGG GTG GAA CTG GCA CTG CCC TCT TGG CAG CCA GTG CCA GGC AAG CTT ACC
TRP THR PRO GLU ARG VAL GLU LEU ALA LEU PRO SER TRP GLN PRO VAL PRO GLY LYS LEU THR

CTA CGC TGC CAG GAG GTG CAG GTG CTG GAA CGG GTG GAG GCA CCC CCC GCC CTC ACC GTG CTC CGT CTG GGG GAG
LEU ARG CYS GLN GLU VAL GLN VAL LEU GLU ARG VAL GLU ALA PRO PRO ALA LEU THR VAL LEU ARG LEU GLY GLU

AAG GAG CTG AAA CGG GAG GAG GAG GTG GGG GAG GAG CCC GAG GCT GTC ACC ACG ACG CTG CTG GTG CTG CTG GTG AGG
LYS GLU LEU LYS ARG GLU GLU GLU VAL GLY GLU GLU PRO GLU ALA VAL THR THR THR LEU LEU VAL LEU LEU VAL ARG

AGA GAT CAC CAT GGA GCC AAT TTC TCG TGC CGC ACT GAA CTG GAC CTG CAA GGG CTG GAG
ARG ASP HIS HIS GLY ALA ASN PHE SER CYS ARG THR GLU LEU ASP LEU GLN GLY LEU GLU
```

```
CTG TTT GAG AAC ACC TCG GCC CCC TAC CAG ACC TTT GTC CTG CCA ACT CCC CCA CAA
LEU PHE GLU ASN THR SER ALA PRO TYR GLN THR PHE VAL LEU PRO THR PRO PRO GLN

CTT GTC AGC CCC CGG GTC ATA GAG GTG GAC CAG GTC TCC TGT CTG TCC CTG GGG CTG
LEU VAL SER PRO ARG VAL ILE GLU VAL ASP GLN VAL SER CYS LEU SER LEU GLY LEU

TTC CCA GTC GAG GCC TCG GAG CAG CAC GTC CAC GAC AAC TTG AGG CCC ACA GGC ACC
PHE PRO VAL GLU ALA SER GLU GLN HIS VAL HIS ASP ASN LEU ARG PRO THR GLY THR

TAT GGC AAC GAC TCC TTC GCC AAG CAG AGT GTG ACC GTG AGC CAG GCA GGC ACC CAG
TYR GLY ASN ASP SER PHE ALA LYS GLN SER VAL THR VAL SER GLN ALA GLY THR GLN

CGG ACG TGT GCA CAC CCC AAC GTG ATT CTG ACG AAG CCA AGC CAG GAG ACA ATC TAC
ARG THR CYS ALA HIS PRO ASN VAL ILE LEU THR LYS PRO SER GLN GLU THR ILE TYR

AGC TTT CCG GCG CAC CTC AGA CCT CAG AAG GTG ACG CAG GCC TTC TCT GCA GTG
SER PHE PRO ALA HIS LEU ARG PRO GLN LYS VAL THR GLN ALA PHE SER ALA VAL

AAG TGT GCC CAC CTG CTG AAG GTG AAT CCA GTT CCA GCC TCC TGC CCA CTG GGC CCG
LYS CYS ALA HIS LEU LEU LYS VAL ASN PRO VAL PRO ALA SER CYS PRO LEU GLY PRO

AGG GCC CAG CTC CTG GCC CAG AAG ACG GAG AAC CGG CTT CGT GTC CAG TAT GCA ACC
ARG ALA GLN LEU LEU ALA GLN LYS THR GLU ASN ARG LEU ARG VAL GLN TYR ALA THR

CTG GAG GAG GCC ATA CAC AAG AAC ACC TGG ACG CCA CAG AAT TCC CAG CTG TAT GCC
LEU GLU GLU ALA ILE HIS LYS ASN THR TRP THR PRO GLN ASN SER GLN LEU TYR ALA

CGA CTG AGG GAT TGT CCG GGA AAC GAA TGG TRP CCA GAG CAG AAT AAG GAT CAG ATG
ARG LEU ARG ASP CYS PRO GLY ASN GLU TRP PRO GLU GLN ASN LYS ASP GLN MET

TGC CAG GCT TGG GGG AAC CCA TTG CCC GAG CTC TTG ACT AAG GAT CTA TGT CCA CTG CCC
CYS GLN ALA TRP GLY ASN PRO LEU PRO GLU LEU LEU THR LYS ASP LEU CYS PRO LEU PRO
```

FIG. 1B

```
ATC GGG GAA TCA GTG ACT GTC ACT CGA GAT CTT GAG GGC ACC TAC CTC TGT CGG GCC AGG AGC ACT
ILE GLY GLU SER VAL THR VAL THR ARG ASP LEU GLU GLY THR TYR LEU CYS ARG ALA ARG SER THR

CAA GGG GAG GTC ACC CGC GAG GTG ACC GTG AAT GTG CTC TCC CCC CGG TAT GAG ATT GTC ATC ATC
GLN GLY GLU VAL THR ARG GLU VAL THR VAL ASN VAL LEU SER PRO ARG TYR GLU ILE VAL ILE ILE

ACT GTG GTA GCA GCC GCA ATG ATA GTC ATA ATG GGC ACT GCA GGC CTC TAT AAC CGC CAG
THR VAL VAL ALA ALA ALA MET ILE VAL ILE MET GLY THR ALA GLY LEU TYR TYR ASN ARG GLN

CGG AAG ATC AAG AAA TAC AGA CTA CAA CAG GCC CAA AAA GGG ACC CCC ATG AAA CCG AAC ACA CAA
ARG LYS ILE LYS LYS TYR ARG LEU GLN GLN ALA GLN LYS GLY THR PRO MET LYS PRO ASN THR GLN

GCC ACG CCT CCC TGA ACCTATCCCG GGACAGGGCC TCTTCCTCGG CCTTCCCATA TTGGTGGCAG TGGTGCCACA
ALA THR PRO PRO ***

CTGAACAGAG TGGAAGACAT ATGCCATGCA GCTACACCTA CCGGCCCTGG GACGCCGGAG GACAGGGCAT TGTCCTCAGT

CAGATACAAC AGCATTTGGG GCCATGGTAC CTGCACACCT AAAACACTAG TGATCTGTAG TCACATGACT

AAGCCAAGAG GAAGGAGCAA GACTCAAGAC ATGATTGATG GATGTTAAAG TCTAGCCTGA TGAGAGGGGA AGTGGTGGGG

GAGACATAGC CCCACCATGA CTGGAAATA CTGAAACTTG CTGCCTATTG GGTATGCTGA GGCCCACAGA

CTTACAGAAG AAGTGGCCCT CCATAGACAT GTGTAGCATC AAAACACAAA GGCCCACACT TCCTGACGGA TGCCAGCTTG

GGCACTGCTG TCTACTGACC CCAACCCTTG ATGATATGTA TTTATTCATT TGTTATTTTA CCAGCTATTT ATTGAGTGTC

TTTTATGTAG GCTAAATGAA CATAGGTCTC TGGCCTCACG GAGCTCCCAG TCCATGTCAC ATTCAAGGTC ACCAGTACA

GTTGTACAGG TTGTACACTG CAGGAGAGTG CCTGGCAAAA AGATCAAATG GGGCTGGGAC TTCTCATTGG CCAACCTGCC

TTTCCCCAGA AGGAGTGATT TTTCTATCGG CACAAAAGCA CTATATGGAC TGGTAATGGT TCACAGGTTC AGAGATTACC
```

FIG. 1C

```
CAGTGAGGCC TTATTCCTCC CTTCCCCCCA AAACTGACAC CTTTGTTAGC CACCTCCCCA CCCACATACA TTTCTGCCAG
TGTTACAATG ACACTCAGCG GTCATGTCTG GACATGAGTG CCCAGGGAAT ATGCCCAAGC TATGCCTTGT CCTCTTGTCC
TGTTTGCATT TCACTGGGAG CTTGCACTAT TGCAGCTCCA GTTTCCTGCA GTGATCAGGG TCCTGCAAGC AGTGGGAAG
GGGCCAAGG TATTGGAGGA CTCCCTCCCA GCTTTGGAAG GGTCATCCGC GTGTGTGTGT GTAGACAAGC
TCTCGCTCTG TCACCCAGGC TGGAGTGCAG TGGTGCAATC ATGGTTCACT GCAGTCTTGA CCTTTGGGC TCAAGTGATC
CTCCCACCTC AGCCTCCTGA GTAGCTGGGA CCATAGGCTC ACAACACCAC ACCTGGCAAA TTTGATTTT TTTTTTTTT
TCAGAGACGG GGTCTCGCAA CATTGCCCAG ACTTCCTTTG TGTTAGTTAA TAAAGCTTTC TCAACTGCCA AAAAAAAAAA
AAAAAAA
```

TTCACATCAA AACTCCTATA CTGACCTGAG ACAGAGGCAG CAGTGATACC CACCTGAGAG ATCCTGTGTT TGA

ACAACTG CTTCCAAAA CGGAAAGTAT TTCAAGCCTA AACCTTTGGG TGAAAAGAAC TCTTGAAGTC ATG ATT
                                                                                                                                    met ile GCT TCA CAG TTT CTC TCA GCT CTC ACT TTG GTG CTT CTC ATT AAA GAG AGT GGA GCC TGG
ala ser gln phe leu ser ala leu thr leu val leu leu ile lys glu ser gly ala trp TCT TAC AAC ACC TCC ACG GAA GCT ATG GCT ACT TAT GAT GAG GCC AGT GCT TGT CAG CAA
ser tyr asn thr ser thr glu ala met ala thr tyr asp glu ala ser ala cys gln gln AGG TAC ACA CAC CTG GTT GCA ATT CAA AAC GAA GAG TAC CTA AAC TCC ATA
arg tyr thr his leu val ala ile gln asn glu glu tyr leu asn ser ile TTG AGC TAT TCA CCA AGT TAT TAC TGG ATT GGA ATC AGA GCC AAG AAC GTC AAT GTG TGG GTC
leu ser tyr ser pro ser tyr tyr trp ile gly ile arg lys val asn val trp val TGG GTA GGA ACC CAG AAA CCT CTG ACA GAA GCC AAG AAC TGG GCT CCA GGT GAA CCC
trp val gly thr gln lys pro leu thr glu ala lys asn trp ala pro gly glu pro AAC AAT AGG CAA AAA GAT GAG GAC TGC GTG GAG ATC TAC ATC TAC ATC AAG AAG AGA GAA AAA GAT GTG
asn asn arg gln lys asp glu asp cys val glu ile tyr ile lys lys arg glu lys asp val GGC ATG TGG AAT GAT GAG AGG TGC AGC AAG AAG CTT GCC CTA TGC CTA ACC ATC AAT TAC ACT
gly met trp asn asp glu arg cys ser lys lys leu ala leu cys tyr thr ala ala TGT ACC AAT ACA TCC TGC AGT GGC CAC GGT GAA TGT GTA GAG ACC ATC AAT GTG AAC TGT ACA GCC
cys thr asn thr ser cys ser gly his gly glu cys val glu thr ile asn asn tyr thr TGC AAG TGT GAC CCT GGC TTC AGT GGA CTC AAG TGT CAA ATT GTG AAC TGT ACA GCC
cys lys cys asp pro gly phe ser gly leu lys cys gln ile val asn cys thr ala

FIG. 2B

```
CTG GAA TCC CCT GAG CAT GGA AGC CTG GTT TGC AGT CAC CCA CTG GGA AAC TTC AGC TAC
leu glu ser pro glu his gly ser leu val cys ser his pro leu gly asn phe ser tyr AAT TCT TCC TGC TCT ATC AGC TGT GAT AGG GGT TAC CTG CCA CTG AGC ATG GAG ACC ATG
asn ser ser cys ser ile ser cys asp arg gly tyr leu pro leu ser met glu thr met CAG TGT ATG TCC TCT GGA GAA TCC AGT GCT CCT ATT CCA GCC TGC AAT GTG GTT GAG TGT
gln cys met ser ser gly glu ser ala pro ile pro ala cys asn val val glu cys GAT GCT GTG ACA AAT CCA GCC TGT TTC CAA AAC CCT GGA AGC TTC
asp ala val thr asn pro ala cys phe gln asn pro gly ser phe CCA TGG AAC ACA ACC TGT ACA TTT GAC GAA GGA GAA CTA ATG AGC TTC ATG
pro trp asn thr thr cys thr phe asp glu gly glu leu met ser phe met AGC CTT CAG TGT ACC TCA TCT GGG AAT CCT CAG TCC AAG GAC ACG AGG CAT TTC AAA GCT GTG
ser leu gln cys thr ser ser gly asn pro gln ser lys asp thr arg his phe lys ala val ACA TGC AGG GCC GTC CGC CAG TCA AAA TCC TGC ACC TGT GAG GAA GGC TTC ATC CCA TTG CAG
thr cys arg ala val arg gln ser lys ser cys thr cys glu glu gly phe ile pro leu gln GGA GAG TTC ACC TTC AAA TCA GAC TGC ACT CAA GTG GGG CAG CAG ATC CAA TTG CAG GTT CCT
gly glu phe thr phe lys ser asp cys thr gln val gly gln gln ile gln leu gln val pro GGA CCA GCC CAG GTT GCC ACT CAA GAA TGC TGG ACA TGG TAC CCC GAG GAC CAA CAG CCA ATC CCA GTT GTT TGT
gly pro ala gln val ala thr gln glu cys trp thr trp tyr pro glu asp gln gln ile pro val val cys GAA GCT TTC CAG TGC ACA TGC TCC AAC CCC GAG CGA CCC GAG GGA CGA GGC TAC ATG AAT TGT CTT CCT
glu ala phe gln cys thr cys ser asn pro glu arg pro glu gly arg gly tyr met asn cys leu pro
```

```
AGT GCT TCT GGC AGT TTC CGT TAT GGG TCC AGC TGT GAG TTC TCC TGT GAG CAG GGT TTT
ser ala ser gly ser phe arg tyr gly ser ser cys glu phe ser cys glu gln gly phe GTG TTG AAG GGA TCC AAA AGG CTC CAA TGT GGC CCC ACA GGG GAG TGG GAC AAC GAG AAG
val leu lys gly ser lys arg leu gln cys gly pro thr gly glu trp asp asn glu lys CCC ACA TGT GAA GCT GTG AGA TGC GAT GCT GTC CAC CAG CCC AAG GGT TTG GTG AGG
pro thr cys glu ala val arg cys asp ala val his gln pro pro lys gly leu val arg TGT GCT CAT TCC CCT ATT GGA GAA TTC ACC TAC AAG TCC TCT TGT GCC TTC AGC TGT GAG
cys ala his ser pro ile gly glu phe thr tyr lys ser ser cys ala phe ser cys glu GAG GGA TTT GAA TTA TAT GGA TCA ACT CAA CTT GAG TGC ACA TCT GAG TGT CAA CAA ACA
glu gly phe glu leu tyr gly ser thr gln leu glu cys thr ser gln gly gln thr GAA GAG GTT CCT TCC TGC CAA GTA AAA GTG TCA AGC CTG GCA GTT CCG GGA AAG ATC
glu glu val pro ser cys gln val lys val ser ser leu ala val pro gly lys ile AAC ATG AGC TGC AGT GGG GAG CCC GTG TTT GGC ACT GTG TGC AAG TTC GCC TGT CCT GAA
asn met ser cys ser gly glu pro val phe gly thr val cys lys phe ala cys pro glu GGA TGG ACG CTC AAT GGC TCT GCA GCT CGG TGT ACA GGA CAC TGG ACA GGA CTT TCT
gly trp thr leu asn gly ser ala arg cys thr gly ala thr gly his trp ser gly CTG CTA CCT ACC TGT GAA CTC TCC ACT GAG TCC AAC ATT CCC TTG GTA GCT GGA CTT CGG
leu leu pro thr cys glu leu ser thr glu ser asn ile pro leu val ala gly leu GCT GCT GGA CTC TCC CTG CTG ACA TTA GCA CCA TTT CTC CTC TGG CTT CGG AAA TGC TTA
ala ala gly leu ser leu leu thr leu ala pro phe leu leu trp leu arg lys cys leu CGG AAA GCA AAG AAA TTT GTT CCT GCC AGC AGC TGC CAA AGC CTT GAA TCA GAC GGA AGC
arg lys ala lys lys phe val pro ala ser ser cys gln ser leu glu ser asp gly ser
```

FIG. 2C

```
TAC CAA AAG CCT TCT TAC ATC CTT TAA GTTCAAA AGAATCAGAA ACAGGTGCAT CTGGGAACT A
tyr gln lys pro ser tyr ile leu ***

GAGGATAC ACTGAAGTTA ACAGAGACAG ATAACTCTCC TCGGGTCTCT GGCCCTTCTT GCCTACTATG CCAG

ATGCCT TTATGGCTGA AACCGCAACA CCCATCACCA CTTCAATAGA TCAAAGTCCA GCAGGCAAGG ACGGCCT

TCA ACTGAAAAGA CTCAGTGTTC CCTTCCTAC TCTCAGGATC AAGAAAGTGT TGGCTAATGA AGGGAAAGGA

TATTTCTTC CAAGCAAAGG TGAAGAGACC AAGACTCTGA AATCTCAGAA TTCCTTTCT AACTCTCCCT TG

CTCGCTGT AAAATCTTGG CACAGAAACA CAATATTTTG TGGCTTTCTT TCTTTTGCCC TTCACAGTGT TTCGA

CAGCT GATTACACAG TTGCTGTGTCAT AAGAATGAAT AATAATTATC CAGAGTTTAG AGGAAAAAAA TGACTAAA

AA TATTATAACT TAAAAAAATG ACAGATGTTG AATGCCCACA GGCAAATGCA TGGAGGGTTG TTAATGGTGC

AAATCCTACT GAATGCTCTG TGCGAGGGTT ACTATGCACA ATTTAATCAC TTTCATCCCT ATGGATTCA GTG

CTTCTTA AAGAGTTCTT AAGGATTGTG ATATTTTTAC TGTAATGCT GTCAACTATG ATATGGTAAA AGTACTTA

ATTC AATACAAGTG TGGTAGGGAC TTAAAAAACT TGTAAAAACT GTCAACTATG ATATGGTAAA AGTACTTA

T TCTAGATTAC CCCCTCATTG TTTATTAACA AATTATGTTA CATCTGTTT AATTTATTT CAAAAAGGA A

ACTATTGTC CCCTAGCAAG GCATGATGTT AACCAGAATA AAGTTCTGAG TGTTTTTACT ACAGTTGTTT TTTG

AAAACA TGGTAGAATT GGAGAGTAAA AACTGAATGG AAGGTTTGTA TATTGTCAGA TATTTTTCA GAAATAT

GTG GTTCCACGA TGAAAAACTT CCATGAGGCC AAACGTTTTG AACTAATAAA AGCATAAATG CAAACACACA

AAGGTATAAT TTTATGAATG TCTTTGTTGG AAAAGAATAC AGAAAGATGG ATGTGCTTTG CATTCCTACA AA

GATGTTTG TCAGATGTGA TATGTAAACA TAATTCTTGT ATATTTCTTGT AGATTTTAAA TTCACAATAG AAACT
```

FIG. 2D

CACCA TGTAAAAGAG TCATCTGGTA GATTTTTAAC GAATGAAGAT GTCTAATAGT TATTCCCTAT TTGTTTTC

TT CTGTATGTTA GGGTGCTCTG GAAGAGAGGA ATGCCTGTGT GAGCAAGCAT TTATGTTTAT TTATAAGCAG

ATTTAACAAT TCCAAAGGAA TCTCCAGTTT TCAGTTGATC ACTGGCAATG AAAAATTCTC AGTCAGTAAT TGC

CAAAGCT GCTCTAGCCT TGAGGAGTGT GAGAATCAAA ACTCTCCTAC ACTTCCATTA ACTTAGCATG TGTTGA

AAAA AAAAGTTTCA GAGAAGTTCT GGCTGAACAC TGGCAACGAC AAAGCCAACA GTCAAAACAG AGATGTGAT

A AGGATCAGAA CAGCAGAGGT TCTTTTAAAG GGGCAGAAAA ACTCTGGGAA ATAAGAGAGA ACAACTACTG T

GATCAGGCT ATGTATGGAA TACAGTGTTA TTTTCTTTGA AATTGTTTAA GTGTTGTAAA TATTTATGTA AACT

GCATTA GAAATTAGCT GTGTGAAATA CCAGTGTGGT TGTGTGTTGA GTTTATTGA TATGTCAGAC CTATTTGACA TAACACTATA

TTA AAATATTTTA TAATTTTTAA AGTATATATT TATTTTAAGCT TATGTCAGAC CTATTTGACA TAACACTATA

AAGGTTGACA ATAAATGTGC TTATGTTT

```
CGGGCCTCAC TGGCTTCAGG AGCTGAATAC CCTCCCAGGC ACACACAGGT GGGACACAAA TAAGGGTTTT GGA

ACCACTA TTTTCTCATC ACGACAGCCA CTTAAA ATG CCT GGG AAG ATG GTC GTG ATC CTT GGA GCC
                                     met pro gly lys met val val ile leu gly ala TCA AAT ATA CTT TGG ATA ATG TTT GCA GCT TCT CAA GCT TTT AAA ATC GAG ACC CCA
ser asn ile leu trp ile met phe ala ala ser gln ala phe lys ile glu thr pro GAA TCT AGA TAT CTT GCT CAG ATT GGT GAC TCC GTC TCA TTG ACT TGC AGC ACA GGC
glu ser arg tyr leu ala gln ile gly asp ser val ser leu thr cys ser thr gly TGT GAG TCC CCA TTT TTC TCT TGG AGA ACC CAG ATA GAT AGT CCA AAT GGG AAG GTG
cys glu ser pro phe phe ser trp arg thr gln ile asp ser pro asn gly lys val ACG AAT GAG GGG ACC ACA TCT ACG CTG ACA ATG AAT CCT GTT AGT TTT GGG AAC GAA CAC
thr asn glu gly thr thr ser thr leu thr met asn pro val ser phe gly asn glu his TCT TAC CTG TGC ACA GCA ACT TGT GAA GAG ATT CAT CCA GAT GTT TCA AAA TTG GAA CAG ATC CAG GTG GAG
ser tyr leu cys thr ala thr cys glu glu ile his pro asp val ser lys leu glu gln ile gln val glu ATC TAC TCT TTT CCT AAG GAT AGT TCA CAT CTC ATG AAG AGT CAG ATT CAT CCA GAT GTT TAC CCA TTT GGC CCT CTG GAG GCT GGG AAG
ile tyr ser phe pro lys asp ser cys his leu met lys ser gln ile his leu tyr pro phe leu glu ala gly lys CCG ATC ACA GAT CAT CTC ATG AAG AGT CAG GAA TTT CTG GAG AGG GAC AGG ATA GAC
pro ile thr asp his leu met lys ser gln glu phe leu glu arg asp arg ile asp TTA AAA GGA GAT AAG AGT TTG CAA GTA ACC TTT ACT CCT GTC ATT GAG GAT GCA GAC AGG AAG
leu lys gly asp lys ser leu gln val thr phe thr pro val ile glu asp ala asp arg lys TCC CTG GAA ACC AAG TTG GAA GTA ACC TTT ACT CCT GTC ATT GAG GAT ATT GGA AAA
ser leu glu thr lys leu glu val thr phe thr pro val ile glu asp ile gly lys GTT CTT GTT TGC CGA GCT AAA TTA CAC ATT GAT GAA ATG GAT TCT GTG CCC ACA GTA AGG
val leu val cys arg ala lys leu his ile asp glu met asp ser val pro thr val arg
```

FIG. 3B

```
CAG GCT GTA AAA GAA TTG CAA GTC TAC ATA TCA CCC AAG AAT ACA GTT ATT TCT GTG AAT
gln ala val lys glu leu gln val tyr ile ser pro lys asn thr val ile ser val asn CCA TCC ACA AAG CTG CAA GAA GGT GGC TCT GTG ACC ATG ACC TGT AGC GAG GGT CTA
pro ser thr lys leu gln glu gly gly ser val thr met thr cys ser glu gly leu CCA GCT CCA GAG ATT TTC TGG TTT TCT AAG AAA TTA GAT AAT GGG GGA CAG CAC CTT TCT
pro ala pro glu ile phe trp phe ser lys lys leu asp asn gly gly gln his leu ser GGA AAT GCA ACT CTC ACC TTA ATT ATT GCT ATG AGG GAA ATG GAA GAT TCT TAT GTG TGT
gly asn ala thr leu thr leu ile ile ala met arg glu met glu asp ser tyr val cys GAA GTT AAT TTG AAT GTT ATT AAA AGA AGA AAA AGA CGG GTG CTC GTG ACT GTT CAA GCA TTC
glu val asn leu asn val ile lys arg arg lys arg arg val leu val thr val gln ala phe CCT AGA GAT CCA GAA ATC GAA GGT GGC CTG CGG AAT ACG GAT ACT GTC ACT CTA GAG TGT
pro arg asp pro glu ile glu gly gly leu arg asn thr asp thr val thr leu glu cys AGC TGC AAG GTT CCT AGC TAC GTG TAC CCC CTT TTG GAG GAT ATG GAT GAT GAA GGG AAC
ser cys lys val pro ser tyr val tyr pro leu leu glu asp met asp asp glu gly asn GAG ACT ATT CTG GAG ATG ATC AAT ATA ATA GAG CTT ACC ATT GAA GAT ACT GGA ACG TAT
glu thr ile leu glu met ile asn ile ile glu leu thr ile glu asp thr gly thr tyr AAA AGT TTG AAG ATG TTT GAA ACC TTC TTC TTC CTT CCT AAA TTC GAA GAT TTT CTT CAA
lys ser leu lys met phe glu thr phe phe phe leu pro lys phe glu asp phe leu gln CAG GCT AAG TTA CAT CAT ATT GAT GAC ATG GAA ATG GAA TTC GAA ATG AAA CAA CAG AGG ACG ACC CTT CTT TCC
gln ala lys leu his his ile asp asp met glu met glu phe glu met lys gln gln arg thr thr leu leu ser ACA CTT TAT GTC AAT GTT GCC CCC AGA GAT GAT ACA ACC GTC TTG GTC ACC ATC CCT TCC
thr leu tyr val asn val ala pro arg asp asp thr thr val leu val thr ile pro ser CTG GAG GAA GGC AGT TCT GTG AAT ATG ATG ACA TGC TTG AGC CAG GGC TTT CCT GCT CCG AAA
leu glu glu gly ser ser val asn met met thr cys leu ser gln gly phe pro ala pro lys
```

```
ATC CTG TGG AGC AGG CAG CTC CCT AAC GGG GAG CTA CAG CCT CTT TCT GAG AAT GCA ACT
ile leu trp ser arg gln leu pro asn gly glu leu gln pro leu ser glu asn ala thr CTC ACC TTA ATT TCT ACA AAA ATG GAA ATG TCT GGG TAT TTA TGT GAA GGA ATT AAC
leu thr leu ile ser thr lys met glu met ser gly tyr leu cys glu gly ile asn CAG GCT GGA AGA AGC AGA GAA AAG GAA GTG GAA TTA ATC ATC CAA GTT CCA AAA GAC ATA
gln ala gly arg ser arg arg lys glu val glu leu ile ile gln val pro lys asp ile AAA CTT ACA GCT TTT CCT TCT GAG AGT GTC AAA GGA GAC ACT GTC ATC ATC TCT TGT
lys leu thr ala phe pro ser glu ser val lys gly asp thr val ile ile ser cys ACA GAA AAT GTT CCA GAA ACA TGG ATA ATC CTG AAG AAA AAA GCG GAG ACA GGA GAC
thr cys gly asn val pro glu thr trp ile ile leu lys lys lys ala glu thr gly asp ACA GTA CTA AAA TCT ATA GAT GGC GCC TAT ACC ATC CGA AAG GCC CAG TTG AAG GAT GCG
thr val leu lys ser ile asp gly ala tyr thr ile arg lys ala gln leu lys asp ala GGA GTA TAT GAA TGT TGT GAA AAC AAA GTT GGC TCA CAA TTA AGA AGT TTA ACA CTT
gly val tyr glu cys cys glu asn lys val gly ser gln leu arg ser leu thr leu GAT GTT CAA GGA AGA GAA AAC AAC AAA AAT CCT GCC ATT GGA ATG ATA ATT TCT CCT GAG CTT CTC TAT
asp val gln gly arg glu asn asn lys asn pro ala ile gly met ile ile ser pro glu leu leu tyr TTT GCA TCC TCC TTA ATA ATA CCT GCC ATT GAC ATG ATA ATT TAC TTT GCA AGA AAA GCC
phe ala ser ser leu ile ile pro ala ile asp met ile ile tyr phe ala arg lys ala AAC ATG AAG GGG TCA TAT AGT TAT TCT CTT GTA GAA GCA CAG TCA AAA TCA AAA GTG TAG CTAATGCTTG
asn met lys gly ser tyr ser tyr ser leu val glu ala gln ser lys ser lys val ***

ATATGTTCAA CTGGAGACAC TATTTATCTG TGCAAATCCT TGATACTGCT CATCATTCCT TGAGAAAAAC AAT

GAGCTGA GAGGCAGACT TCCCTGAATG TATTGAACTT GGAAAGAAAT GCCCATCTAT GTCCCTTGCT GTGAGC

AAGA AGTCAAAGTA AAACTTGCTG CCTGAAGAAC AGTAACTGCC ATCAAGATGA GAGAACTGGA GGAGTCCT

T GATCTCTGTATA TACAATAACA TAATTTGTAC ATATGTAAAA TAAAATTATG CCATAGCAAG ATTGCTTAAAA
```

FIG. 3C

TAGCAACAC TCTATATTTA GATTGTTAAA ATAACTAGTG TTGCTTGGAC TATTATAATT TAATGCATGT TAGG

AAAATT TCACATTAAT ATTTGCTGAC AGCTGACCTT TGTCATCTTT CTTCTATTTT ATTCCCTTTC ACAAAAT

TTT ATTCCTATAT AGTTTATTGA CAATAATTTC AGTTTTGTA AGATGCCGG GTTTATATT TTTATAGACA

AATAATAAGC AAAGGGAGCA CTGGGTTGAC TTTCAGGTAC TAAATACCTC AACCTATGGT ATAATGGTTG AC

TGGGTTTC TCTGTATAGT ACTGGCATGG TACGGAGATG TTTCACGAAG TTTGTTCATC AGACTCCTGT GCAAC

TTTCC CAATGTGGGCC TAAAAATGCA ACTTCTTTTT ATTTTCTTTT GTAAATGTTT AGGTTTTTT GTATAGTA

AA GTGATAATTT CTGGAATTAA AAA

FIG. 3D

SEQUENCE LISTING (1) GENERAL INFORMATION:

(iii) NUMBER OF SEQUENCES: 109

(2) INFORMATION FOR SEQ ID NO: 1:

(i) SEQUENCE CHARACTERISTICS:
        (A) LENGTH: 18
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 1:

TGGGAGCCAT AGCGAGGC                                                 18

(2) INFORMATION FOR SEQ ID NO: 2:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 2:

GAGGAGCTCA GCGTCGACTG                                               20

(2) INFORMATION FOR SEQ ID NO: 3:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 3:

GACACTCAAT AAATAGCTGG T                                             21

(2) INFORMATION FOR SEQ ID NO: 4:

(i) SEQUENCE CHARACTERISTICS:
        (A) LENGTH: 18
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 4:

GAGGCTGAGG TGGGAGGA                                                 18

(2) INFORMATION FOR SEQ ID NO: 5:

(i) SEQUENCE CHARACTERISTICS:
        (A) LENGTH: 18
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 5:

```
CGATGGGCAG TGGGAAAG                                                   18

(2) INFORMATION FOR SEQ ID NO: 6:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 6:

GGGCGCGTGA TCCTTATAGC                                                 20

(2) INFORMATION FOR SEQ ID NO: 7:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 7:

CATAGCGAGG CTGAGGTTGC                                                 20

(2) INFORMATION FOR SEQ ID NO: 8:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 8:

CGGGGGCTGC TGGGAGCCAT                                                 20

(2) INFORMATION FOR SEQ ID NO: 9:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 9:

AGAGCCCCGA GCAGGACCAG                                                 20

(2) INFORMATION FOR SEQ ID NO: 10:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 10:

TGCCCATCAG GGCAGTTTGA                                                 20
```

(2) INFORMATION FOR SEQ ID NO: 11:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 11:

GGTCACACTG ACTGAGGCCT                                        20

(2) INFORMATION FOR SEQ ID NO: 12:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 12:

CTCGCGGGTG ACCTCCCCTT                                        20

(2) INFORMATION FOR SEQ ID NO: 13:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 13:

TCAGGGAGGC GTGGCTTGTG                                        20

(2) INFORMATION FOR SEQ ID NO: 14:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 14:

CCTGTCCCGG GATAGGTTC A                                        20

(2) INFORMATION FOR SEQ ID NO: 15:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 15:

CCCCCACCAC TTCCCCTCTC                                        20

(2) INFORMATION FOR SEQ ID NO: 16:

(i) SEQUENCE CHARACTERISTICS:
        (A) LENGTH: 20

```
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 16:

TTGAGAAAGC TTTATTAACT                                              20

(2) INFORMATION FOR SEQ ID NO: 17:

(i) SEQUENCE CHARACTERISTICS:
          (A) LENGTH: 14
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 17:

AGCCATAGCG AGGC                                                    14

(2) INFORMATION FOR SEQ ID NO: 18:

(i) SEQUENCE CHARACTERISTICS:
          (A) LENGTH: 12
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 18:

CCATAGCGAG GC                                                      12

(2) INFORMATION FOR SEQ ID NO: 19:

(i) SEQUENCE CHARACTERISTICS:
          (A) LENGTH: 10
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 19:

ATAGCGAGGC                                                         10

(2) INFORMATION FOR SEQ ID NO: 20:

(i) SEQUENCE CHARACTERISTICS:
          (A) LENGTH: 16
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 20:

TGGGAGCCAT AGCGAG                                                  16

(2) INFORMATION FOR SEQ ID NO: 21:

(i) SEQUENCE CHARACTERISTICS:
          (A) LENGTH: 16
          (B) TYPE: Nucleic Acid
          (C) STRANDEDNESS: Single
          (D) TOPOLOGY: Linear
```

(iv) ANTI-SENSE: Yes (xi) SEQUENCE DESCRIPTION: SEQ ID NO: 21:

GGAGCCATAG CGAGGC                                                      16

(2) INFORMATION FOR SEQ ID NO: 22:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 22:

GCCCAAGCTG GCATCCGTCA                                                  20

(2) INFORMATION FOR SEQ ID NO: 23:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 23:

TCTGTAAGTC TGTGGGCCTC                                                  20

(2) INFORMATION FOR SEQ ID NO: 24:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 24:

AGTCTTGCTC CTTCCTCTTG                                                  20

(2) INFORMATION FOR SEQ ID NO: 25:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 25:

CTCATCAGGC TAGACTTTAA                                                  20

(2) INFORMATION FOR SEQ ID NO: 26:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 26:

```
TGTCCTCATG GTGGGGCTAT                                                      20

(2) INFORMATION FOR SEQ ID NO: 27:

(i) SEQUENCE CHARACTERISTICS:
           (A) LENGTH: 22
           (B) TYPE: Nucleic Acid
           (C) STRANDEDNESS: Single
           (D) TOPOLOGY: Linear (iv) ANTI-SENSE: Yes (xi) SEQUENCE DESCRIPTION:  SEQ ID NO: 27:

TCTGAGTAGC AGAGGAGCTC GA                                                   22

(2) INFORMATION FOR SEQ ID NO: 28:

(i) SEQUENCE CHARACTERISTICS:
           (A) LENGTH: 22
           (B) TYPE: Nucleic Acid
           (C) STRANDEDNESS: Single
           (D) TOPOLOGY: Linear (iv) ANTI-SENSE: Yes (xi) SEQUENCE DESCRIPTION:  SEQ ID NO: 28:

CAATCATGAC TTCAAGAGTT CT                                                   22

(2) INFORMATION FOR SEQ ID NO: 29:

(i) SEQUENCE CHARACTERISTICS:
           (A) LENGTH: 20
           (B) TYPE: Nucleic Acid
           (C) STRANDEDNESS: Single
           (D) TOPOLOGY: Linear (iv) ANTI-SENSE: Yes (xi) SEQUENCE DESCRIPTION:  SEQ ID NO: 29:

ACCACACTGG TATTTCACAC                                                      20

(2) INFORMATION FOR SEQ ID NO: 30:

(i) SEQUENCE CHARACTERISTICS:
           (A) LENGTH: 21
           (B) TYPE: Nucleic Acid
           (C) STRANDEDNESS: Single
           (D) TOPOLOGY: Linear (iv) ANTI-SENSE: Yes (xi) SEQUENCE DESCRIPTION:  SEQ ID NO: 30:

GTATGGAAGA TTATAATATA T                                                    21

(2) INFORMATION FOR SEQ ID NO: 31:

(i) SEQUENCE CHARACTERISTICS:
           (A) LENGTH: 21
           (B) TYPE: Nucleic Acid
           (C) STRANDEDNESS: Single
           (D) TOPOLOGY: Linear (iv) ANTI-SENSE: Yes (xi) SEQUENCE DESCRIPTION:  SEQ ID NO: 31:

CACAATCCTT AAGAACTCTT T                                                    21

(2) INFORMATION FOR SEQ ID NO: 32:
```

(i) SEQUENCE CHARACTERISTICS:
    (A) LENGTH: 20
    (B) TYPE: Nucleic Acid
    (C) STRANDEDNESS: Single
    (D) TOPOLOGY: Linear (iv) ANTI-SENSE: Yes (xi) SEQUENCE DESCRIPTION: SEQ ID NO: 32:

ACCTCTGCTG TTCTGATCCT                                       20

(2) INFORMATION FOR SEQ ID NO: 33:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 33:

CTGCTGCCTC TGTCTCAGGT                                       20

(2) INFORMATION FOR SEQ ID NO: 34:

(i) SEQUENCE CHARACTERISTICS:
        (A) LENGTH: 15
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 34:

GGTATTTGAC ACAGC                                            15

(2) INFORMATION FOR SEQ ID NO: 35:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 35:

AATCATGACT TCAAGAGTTC T                                     21

(2) INFORMATION FOR SEQ ID NO: 36:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 36:

TGAAGCAATC ATGACTTCAA G                                     21

(2) INFORMATION FOR SEQ ID NO: 37:

(i) SEQUENCE CHARACTERISTICS:
        (A) LENGTH: 20
        (B) TYPE: Nucleic Acid

```
            (C) STRANDEDNESS: Single
            (D) TOPOLOGY: Linear (iv) ANTI-SENSE: Yes (xi) SEQUENCE DESCRIPTION: SEQ ID NO: 37:

TATAGGAGTT TTGATGTGAA                                              20

(2) INFORMATION FOR SEQ ID NO: 38:

(i) SEQUENCE CHARACTERISTICS:
            (A) LENGTH: 21
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 38:

ACAATGAGGG GGTAATCTAC A                                            21

(2) INFORMATION FOR SEQ ID NO: 39:

(i) SEQUENCE CHARACTERISTICS:
            (A) LENGTH: 21
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 39:

GACAATATAC AAACCTTCCA T                                            21

(2) INFORMATION FOR SEQ ID NO: 40:

(i) SEQUENCE CHARACTERISTICS:
            (A) LENGTH: 21
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 40:

CCAGGCATTT TAAGTTGCTG T                                            21

(2) INFORMATION FOR SEQ ID NO: 41:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 41:

CCTGAAGCCA GTGAGGCCCG                                              20

(2) INFORMATION FOR SEQ ID NO: 42:

(i) SEQUENCE CHARACTERISTICS:
            (A) LENGTH: 21
            (B) TYPE: Nucleic Acid
            (C) STRANDEDNESS: Single
            (D) TOPOLOGY: Linear (iv) ANTI-SENSE: Yes
```

(xi) SEQUENCE DESCRIPTION: SEQ ID NO: 42:

GATGAGAAAA TAGTGGAACC A                                             21

(2) INFORMATION FOR SEQ ID NO: 43:

(i) SEQUENCE CHARACTERISTICS:
       (A) LENGTH: 19
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 43:

CTGAGCAAGA TATCTAGAT                                                19

(2) INFORMATION FOR SEQ ID NO: 44:

(i) SEQUENCE CHARACTERISTICS:
       (A) LENGTH: 19
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 44:

CTACACTTTT GATTTCTGT                                                19

(2) INFORMATION FOR SEQ ID NO: 45:

(i) SEQUENCE CHARACTERISTICS:
       (A) LENGTH: 22
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 45:

TTGAACATAT CAAGCATTAG CT                                            22

(2) INFORMATION FOR SEQ ID NO: 46:

(i) SEQUENCE CHARACTERISTICS:
       (A) LENGTH: 22
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 46:

TTTACATATG TACAAATTAT GT                                            22

(2) INFORMATION FOR SEQ ID NO: 47:

(i) SEQUENCE CHARACTERISTICS:
       (A) LENGTH: 22
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 47:

AATTATCACT TTACTATACA AA                                            22

(2) INFORMATION FOR SEQ ID NO: 48:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 48:

AGGGCTGACC AAGACGGTTG T                                     21

(2) INFORMATION FOR SEQ ID NO: 49:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 49:

CCATCTTCCC AGGCATTTTA                                      20

(2) INFORMATION FOR SEQ ID NO: 50:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 50:

AACCCAGTGC TCCCTTTGCT                                      20

(2) INFORMATION FOR SEQ ID NO: 51:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 51:

GGCCACATTG GGAAAGTTGC                                      20

(2) INFORMATION FOR SEQ ID NO: 52:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 52:

GAAGTCAGCC AAGAACAGCT                                      20

(2) INFORMATION FOR SEQ ID NO: 53:

(i) SEQUENCE CHARACTERISTICS:
        (A) LENGTH:   20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 53:

ACAGGATCTC TCAGGTGGGT                                                    20

(2) INFORMATION FOR SEQ ID NO: 54:

(i) SEQUENCE CHARACTERISTICS:
        (A) LENGTH:   20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 54:

CCAAAGTGAG AGCTGAGAGA                                                    20

(2) INFORMATION FOR SEQ ID NO: 55:

(i) SEQUENCE CHARACTERISTICS:
        (A) LENGTH:   20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 55:

CTGATTCAAG GCTTTGGCAG                                                    20

(2) INFORMATION FOR SEQ ID NO: 56:

(i) SEQUENCE CHARACTERISTICS:
        (A) LENGTH:   20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 56:

TTCCCCAGAT GCACCTGTTT                                                    20

(2) INFORMATION FOR SEQ ID NO: 57:

(i) SEQUENCE CHARACTERISTICS:
        (A) LENGTH:   20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 57:

GGGCCAGAGA CCCGAGGAGA                                                    20

(2) INFORMATION FOR SEQ ID NO: 58:

(i) SEQUENCE CHARACTERISTICS:
        (A) LENGTH:   20
        (B) TYPE: Nucleic Acid
        (C) STRANDEDNESS: Single (D) TOPOLOGY: Linear (iv) ANTI-SENSE: Yes (xi) SEQUENCE DESCRIPTION: SEQ ID NO: 58:

ACGTTTGGCC TCATGGAAGT                                               20

(2) INFORMATION FOR SEQ ID NO: 59:

(i) SEQUENCE CHARACTERISTICS:
        (A) LENGTH:   20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 59:

GGAATGCAAA GCACATCCAT                                               20

(2) INFORMATION FOR SEQ ID NO: 60:

(i) SEQUENCE CHARACTERISTICS:
        (A) LENGTH:   20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 60:

CGATGCAGAT ACCGCGGAGT                                               20

(2) INFORMATION FOR SEQ ID NO: 61:

(i) SEQUENCE CHARACTERISTICS:
        (A) LENGTH:   20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 61:

GCCTGGGAGG GTATTCAGCT                                               20

(2) INFORMATION FOR SEQ ID NO: 62:

(i) SEQUENCE CHARACTERISTICS:
        (A) LENGTH:   20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 62:

CCTGTGTGTG CCTGGGAGGG                                               20

(2) INFORMATION FOR SEQ ID NO: 63:

(i) SEQUENCE CHARACTERISTICS:
        (A) LENGTH:   20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 63:

GGCATTTTAA GTTGCTGTCG                                           20

(2) INFORMATION FOR SEQ ID NO: 64:

(i) SEQUENCE CHARACTERISTICS:
        (A) LENGTH:   20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 64:

CAGCCTGCCT TACTGTGGGC                                           20

(2) INFORMATION FOR SEQ ID NO: 65:

(i) SEQUENCE CHARACTERISTICS:
        (A) LENGTH:   21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 65:

CTTGAACAAT TAATTCCACC T                                         21

(2) INFORMATION FOR SEQ ID NO: 66:

(i) SEQUENCE CHARACTERISTICS:
        (A) LENGTH:   21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 66:

TTACCATTGA CATAAAGTGT T                                         21

(2) INFORMATION FOR SEQ ID NO: 67:

(i) SEQUENCE CHARACTERISTICS:
        (A) LENGTH:   20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 67:

CTGTGTCTCC TGTCTCCGCT                                           20

(2) INFORMATION FOR SEQ ID NO: 68:

(i) SEQUENCE CHARACTERISTICS:
        (A) LENGTH:   21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 68:

GTCTTTGTTG TTTTCTCTTC C                                         21

(2) INFORMATION FOR SEQ ID NO: 69:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 69:

TGAACATATC AAGCATTAGC                                    20

(2) INFORMATION FOR SEQ ID NO: 70:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 70:

GCAATCTTGC TATGGCATAA                                    20

(2) INFORMATION FOR SEQ ID NO: 71:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 71:

CCCGGCATCT TTACAAAACC                                    20

(2) INFORMATION FOR SEQ ID NO: 72:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 72:

AACATCTCCG TACCATGCCA                                    20

(2) INFORMATION FOR SEQ ID NO: 73:

(i) SEQUENCE CHARACTERISTICS:
        (A) LENGTH: 22
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 73:

TCACTGCTGC CTCTGTCTCA GG                                  22

(2) INFORMATION FOR SEQ ID NO: 74:

(i) SEQUENCE CHARACTERISTICS:

(A) LENGTH: 23
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 74:

TGATTCTTTT GAACTTAAAA GGA                                              23

(2) INFORMATION FOR SEQ ID NO: 75:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 75:

TTAAAGGATG TAAGAAGGCT                                                  20

(2) INFORMATION FOR SEQ ID NO: 76:

(i) SEQUENCE CHARACTERISTICS:
        (A) LENGTH: 19
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 76:

CATAAGCACA TTTATTGTC                                                   19

(2) INFORMATION FOR SEQ ID NO: 77:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 77:

TTTTGGGAAG CAGTTGTTCA                                                  20

(2) INFORMATION FOR SEQ ID NO: 78:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 78:

AACTGTGAAG CAATCATGAC T                                                21

(2) INFORMATION FOR SEQ ID NO: 79:

(i) SEQUENCE CHARACTERISTICS:
        (A) LENGTH: 22
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 79:

CCTTGAGTGG TGCATTCAAC CT                                             22

(2) INFORMATION FOR SEQ ID NO: 80:

(i) SEQUENCE CHARACTERISTICS:
            (A) LENGTH: 22
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 80:

AATGCTTGCT CACACAGGCA TT                                             22

(2) INFORMATION FOR SEQ ID NO: 81:

(i) SEQUENCE CHARACTERISTICS:
            (A) LENGTH: 18
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 81:

GCCTCGCTAT GGCTCCCA                                                  18

(2) INFORMATION FOR SEQ ID NO: 82:

(i) SEQUENCE CHARACTERISTICS:
            (A) LENGTH: 18
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 82:

CATGGCGCGG GCCGCGGG                                                  18

(2) INFORMATION FOR SEQ ID NO: 83:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 83:

TGCATCCCCC AGGCCACCAT                                                20

(2) INFORMATION FOR SEQ ID NO: 84:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 84:

TCTGAGTAGC AGAGGAGCTC                                          20

(2) INFORMATION FOR SEQ ID NO: 85:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 85:

TATGTCTCCC CCACCACTTC                                          20

(2) INFORMATION FOR SEQ ID NO:86:

(i) SEQUENCE CHARACTERISTICS:
        (A) LENGTH:18
        (B) TYPE: Nucleic Acid
        (C) STRANDEDNESS: Single
        (D) TOPOLOGY: Linear (xi) SEQUENCE DESCRIPTION: SEQ ID NO: 86:

CTTGTGTATA AGCTGGCC                                            18

(2) INFORMATION FOR SEQ ID NO:87:

(i) SEQUENCE CHARACTERISTICS:
        (A) LENGTH:18
        (B) TYPE: Nucleic Acid
        (C) STRANDEDNESS: Single
        (D) TOPOLOGY: Linear (xi) SEQUENCE DESCRIPTION: SEQ ID NO:87:

CCCGGACAAT CCCTCTCG                                            18

(2) INFORMATION FOR SEQ ID NO:88:

(i) SEQUENCE CHARACTERISTICS:
        (A) LENGTH:18
        (B) TYPE: Nucleic Acid
        (C) STRANDEDNESS: Single
        (D) TOPOLOGY: Linear (xi) SEQUENCE DESCRIPTION: SEQ ID NO:88:

TCTGCTGGGA ATTTTCTG                                            18

(2) INFORMATION FOR SEQ ID NO:89:

(i) SEQUENCE CHARACTERISTICS:
        (A) LENGTH:18
        (B) TYPE: Nucleic Acid
        (C) STRANDEDNESS: Single
        (D) TOPOLOGY: Linear (xi) SEQUENCE DESCRIPTION: SEQ ID NO:89:

CACATTGGAG TCTGCTGG                                            18

(2) INFORMATION FOR SEQ ID NO:90:

(i) SEQUENCE CHARACTERISTICS:
        (A) LENGTH:18
        (B) TYPE: Nucleic Acid
        (C) STRANDEDNESS: Single
        (D) TOPOLOGY: Linear (xi) SEQUENCE DESCRIPTION: SEQ ID NO:90:

CTCGGGCAAT GGGTTCCC                                                    18

(2) INFORMATION FOR SEQ ID NO:91:

(i) SEQUENCE CHARACTERISTICS:
        (A) LENGTH:18
        (B) TYPE: Nucleic Acid
        (C) STRANDEDNESS: Single
        (D) TOPOLOGY: Linear (xi) SEQUENCE DESCRIPTION: SEQ ID NO:91:

TTAGACACTT GAGCTCGG                                                    18

(2) INFORMATION FOR SEQ ID NO:92:

(i) SEQUENCE CHARACTERISTICS:
        (A) LENGTH:18
        (B) TYPE: Nucleic Acid
        (C) STRANDEDNESS: Single
        (D) TOPOLOGY: Linear (xi) SEQUENCE DESCRIPTION: SEQ ID NO:92:

ACAGTCACTG ATTCCCCG                                                    18

(2) INFORMATION FOR SEQ ID NO:93:

(i) SEQUENCE CHARACTERISTICS:
        (A) LENGTH:18
        (B) TYPE: Nucleic Acid
        (C) STRANDEDNESS: Single
        (D) TOPOLOGY: Linear (xi) SEQUENCE DESCRIPTION: SEQ ID NO:93:

ATCTCGAGTG ACAGTCAC                                                    18

(2) INFORMATION FOR SEQ ID NO:94:

(i) SEQUENCE CHARACTERISTICS:
        (A) LENGTH:18
        (B) TYPE: Nucleic Acid
        (C) STRANDEDNESS: Single
        (D) TOPOLOGY: Linear (xi) SEQUENCE DESCRIPTION: SEQ ID NO:94:

CACAGAGGTA GGTGCCCT                                                    18

(2) INFORMATION FOR SEQ ID NO:95:

(i) SEQUENCE CHARACTERISTICS:
        (A) LENGTH:18
        (B) TYPE: Nucleic Acid
        (C) STRANDEDNESS: Single
        (D) TOPOLOGY: Linear (xi) SEQUENCE DESCRIPTION: SEQ ID NO:95:

CTCCCCTTGA GTGCTCCT                                                    18

(2) INFORMATION FOR SEQ ID NO:96:

(i) SEQUENCE CHARACTERISTICS:
        (A) LENGTH:18
        (B) TYPE: Nucleic Acid
        (C) STRANDEDNESS: Single
        (D) TOPOLOGY: Linear (xi) SEQUENCE DESCRIPTION: SEQ ID NO:96:

TGACAATCTC ATACCGGG                                              18

(2) INFORMATION FOR SEQ ID NO:97:

(i) SEQUENCE CHARACTERISTICS:
        (A) LENGTH:20
        (B) TYPE: Nucleic Acid
        (C) STRANDEDNESS: Single
        (D) TOPOLOGY: Linear (xi) SEQUENCE DESCRIPTION: SEQ ID NO:97:

CCACAGTGAT GATGACAATC                                            20

(2) INFORMATION FOR SEQ ID NO:98:

(i) SEQUENCE CHARACTERISTICS:
        (A) LENGTH:18
        (B) TYPE: Nucleic Acid
        (C) STRANDEDNESS: Single
        (D) TOPOLOGY: Linear (xi) SEQUENCE DESCRIPTION: SEQ ID NO:98:

TACGTGCTGA GGCCTGCA                                              18

(2) INFORMATION FOR SEQ ID NO:99:

(i) SEQUENCE CHARACTERISTICS:
        (A) LENGTH:18
        (B) TYPE: Nucleic Acid
        (C) STRANDEDNESS: Single
        (D) TOPOLOGY: Linear (xi) SEQUENCE DESCRIPTION: SEQ ID NO:99:

GGCGGTTATA GAGGTACG                                              18

(2) INFORMATION FOR SEQ ID NO:100:

(i) SEQUENCE CHARACTERISTICS:
        (A) LENGTH:20
        (B) TYPE: Nucleic Acid
        (C) STRANDEDNESS: Single
        (D) TOPOLOGY: Linear (xi) SEQUENCE DESCRIPTION: SEQ ID NO:100:

CCTGTTGTAG TCTGTATTTC                                            20

(2) INFORMATION FOR SEQ ID NO:101:

(i) SEQUENCE CHARACTERISTICS:
        (A) LENGTH:18
        (B) TYPE: Nucleic Acid
        (C) STRANDEDNESS: Single
        (D) TOPOLOGY: Linear (xi) SEQUENCE DESCRIPTION: SEQ ID NO:101:

CCGGTAGGTG TAGCTGCA                                              18

(2) INFORMATION FOR SEQ ID NO:102:

(i) SEQUENCE CHARACTERISTICS:
        (A) LENGTH:18
        (B) TYPE: Nucleic Acid
        (C) STRANDEDNESS: Single
        (D) TOPOLOGY: Linear (xi) SEQUENCE DESCRIPTION: SEQ ID NO:102:

```
CTGTTGTATC TGACTGAG                                                    18

(2) INFORMATION FOR SEQ ID NO:103:

(i) SEQUENCE CHARACTERISTICS:
        (A) LENGTH:18
        (B) TYPE: Nucleic Acid
        (C) STRANDEDNESS: Single
        (D) TOPOLOGY: Linear (xi) SEQUENCE DESCRIPTION: SEQ ID NO:103:

GATCAGATGC GTGGCCTA                                                    18

(2) INFORMATION FOR SEQ ID NO:104:

(i) SEQUENCE CHARACTERISTICS:
        (A) LENGTH:20
        (B) TYPE: Nucleic Acid
        (C) STRANDEDNESS: Single
        (D) TOPOLOGY: Linear (xi) SEQUENCE DESCRIPTION: SEQ ID NO:104:

GATCGCGTCG GACTATGAAG                                                  20

(2) INFORMATION FOR SEQ ID NO:105:

(i) SEQUENCE CHARACTERISTICS:
        (A) LENGTH: 18
        (B) TYPE: Nucleic Acid
        (C) STRANDEDNESS: Single
        (D) TOPOLOGY: Linear (xi) SEQUENCE DESCRIPTION: SEQ ID NO:105:

GACAGAGGTA GGTGCCCT                                                    18

(2) INFORMATION FOR SEQ ID NO:106:

(i) SEQUENCE CHARACTERISTICS:
        (A) LENGTH:20
        (B) TYPE: Nucleic Acid
        (C) STRANDEDNESS: Single
        (D) TOPOLOGY: Linear (xi) SEQUENCE DESCRIPTION: SEQ ID NO:106:

AGGGCCACTG CTCGTCCACA                                                  20

(2) INFORMATION FOR SEQ ID NO:107:

(i) SEQUENCE CHARACTERISTICS:
        (A) LENGTH:21
        (B) TYPE: Nucleic Acid
        (C) STRANDEDNESS: Single
        (D) TOPOLOGY: Linear (xi) SEQUENCE DESCRIPTION: SEQ ID NO:107:

GCCGAGGTCC ATGTCGTACGC                                                 21

(2) INFORMATION FOR SEQ ID NO:108:

(i) SEQUENCE CHARACTERISTICS:
        (A) LENGTH:20
        (B) TYPE: Nucleic Acid
        (C) STRANDEDNESS: Single
        (D) TOPOLOGY: Linear (xi) SEQUENCE DESCRIPTION: SEQ ID NO:108:

CAGCCATGGT TCCCCCCAAC                                                  20
```

-continued (2) INFORMATION FOR SEQ ID NO:109:

(i) SEQUENCE CHARACTERISTICS:
        (A) LENGTH:20
        (B) TYPE: Nucleic Acid
        (C) STRANDEDNESS: Single
        (D) TOPOLOGY: Linear (xi) SEQUENCE DESCRIPTION: SEQ ID NO:109:

GACGCATCGC GCCTACATCG                         20

ANTISENSE MODULATION OF CELL ADHESION MOLECULE EXPRESSION AND TREATMENT OF CELL ADHESION MOLECULE-ASSOCIATED DISEASES

CROSS-REFERENCES TO RELATED APPLICATIONS

This application is a continuation-in-part of application Ser. No. 08/440,740 (filed May 12, 1995, now U.S. Pat. No. 5,843,738), which is a continuation-in-part of application Ser. No. 08/063,167 (filed May 17, 1993, now U.S. Pat. No. 5,514,788) which is a continuation of application Ser. No. 07/969,151 (filed Feb. 10, 1993), now abandoned, which is a continuation-in-part of application Ser. No. 08/007,997 (filed Jan. 21, 1993, now U.S. Pat. No. 5,591,623), which is a continuation-in-part of application Ser. No. 07/939,855 (filed Sep. 2, 1992), now abandoned, which is a continuation-in-part of application Ser. No. 07/567,286 (filed Aug. 14, 1990), now abandoned. The contents of all of the aforementioned are herein incorporated by reference in their entirety.

FIELD OF THE INVENTION

The present invention provides compositions and methods for detecting and modulating levels of cellular adhesion molecules (CAMs), particularly human intercellular adhesion molecule-1 (ICAM-1) (also known as CD54). In particular, the invention relates to antisense compounds specifically hybridizable with nucleic acids encoding CAMs that can modulate the expression of such CAM proteins. Cams are proteins which are expressed on the surfaces of a variety of cell types and which mediate cell:cell interactions and subsequent cellular and biological responses, including, but not limited to, T cell activation, leukocyte transmigration and inflammation. Accordingly, modulation of the expression of CAMs by one or more antisense compounds of the invention allows for the control of cell:cell interactions and resulting effects such as, e.g., inflammation. The invention is thus directed to diagnostic methods for detecting, and prophylactic, palliative and therapeutic methods for preventing and treating, conditions associated with CAM-mediated processes or with abnormal expression of CAM proteins.

BACKGROUND OF THE INVENTION

Inflammation is a localized protective response elicited by tissues in response to injury, infection, or tissue destruction resulting in the destruction of the infectious or injurious agent and isolation of the injured tissue. A typical inflammatory response proceeds as follows: recognition of an antigen as foreign or recognition of tissue damage, synthesis and release of soluble inflammatory mediators, recruitment of inflammatory cells to the site of infection or tissue damage, destruction and removal of the invading organism or damaged tissue, and deactivation of the system once the invading organism or damage has been resolved. In many human diseases with an inflammatory component, the normal, homeostatic mechanisms which attenuate the inflammatory responses are defective, resulting in damage and destruction of normal tissue.

Cell-cell interactions are involved in the activation of the immune response at each of the stages described above. One of the earliest detectable events in a normal inflammatory response is adhesion of leukocytes to the vascular endothelium, followed by migration of leukocytes out of the vasculature to the site of infection or injury. The adhesion of these leukocytes, or white blood cells, to vascular endothelium is an obligate step in the migration out of the vasculature. Harlan, J. M., Blood 1985, 65, 513–525. In general, the first inflammatory cells to appear at the site of inflammation are neutrophils followed by monocytes, and lymphocytes. Cell-cell interactions are also critical for propagation of both B-lymphocytes and T-lymphocytes resulting in enhanced humoral and cellular immune responses, respectively.

The adhesion of white blood cells to vascular endothelium and other cell types is mediated by interactions between specific proteins, termed "cellular adhesion molecules," or CAMs, located on the plasma membrane of both white blood cells and vascular endothelium. The interaction between adhesion molecules is similar to classical receptor ligand interactions with the exception that the ligand is fixed to the surface of a cell instead of being soluble. The identification of patients with a genetic defect in leukocyte adhesion has enabled investigators to identify a family of proteins responsible for adherence of white blood cells. Leukocyte adhesion deficiency (LAD) is a rare autosomal trait characterized by recurrent bacterial infections and impaired pus formation and wound healing. The defect was shown to occur in the common B-subunit of three heterodimeric glycoproteins, Mac-1, leukocyte function-associated antigen-1 (LFA-1), and p150,95, normally expressed on the outer cell membrane of white blood cells. Anderson and Springer, Ann. Rev. Med. 1987, 38, 175–194. Patients suffering from LAD exhibit a defect in a wide spectrum of adherence-dependent functions of granulocytes, monocytes, and lymphocytes. Three ligands for LFA-1 have been identified, intercellular adhesion molecules 1, 2 and 3 (ICAM-1, ICAM-2 and ICAM-3). Both Mac-1 and p150,95 bind complement fragment C3bi and perhaps other unidentified ligands. Mac-1 also binds ICAM-1.

Other CAM molecules have been identified which are involved in the adherence of white blood cells to vascular endothelium and subsequent migration out of the vasculature. These include endothelial leukocyte adhesion molecule-1 (ELAM-1 or E-selectin), vascular cell adhesion molecule-1 (VCAM-1) and granule membrane protein-140 (GMP-140) and their respective receptors. PECAM-1 proteins are glycoproteins which are expressed on the surfaces of a variety of cell types (for reviews of PECAM-1 proteins, see Newman, J. Clin. Invest., 1997, 99, 3 and DeLisser et al., Immunol. Today, 1994, 15, 490). The adherence of white blood cells to vascular endothelium appears to be mediated in part if not in toto by ICAM-1, ICAM-2, ELAM-1, VCAM-1 and GMP-140. Dustin and Springer, J. Cell Biol. 1987, 107, 321–331. Expression on the cell surface of ICAM-1, ELAM-1, VCAM-1 and GMP-140 adhesion molecules is induced by inflammatory stimuli. In contrast, expression of ICAM-2 appears to be constitutive and not sensitive to induction by cytokines. In general, GMP-140 is induced by autocoids such as histamine, leukotriene $B_4$, platelet activating factor, and thrombin. Maximal expression on endothelial cells is observed 30 minutes to 1 hour after stimulation, and returns to baseline within 2 to 3 hours. The expression of ELAM-1 and VCAM-1 on endothelial cells is induced by cytokines such as interleukin-1β and tumor necrosis factor, but not gamma-interferon. Maximal expression of ELAM-1 on the surface of endothelial cells occurs 4 to 6 hours after stimulation, and returns to baseline by 16 hours. ELAM-1 expression is dependent on new mRNA and protein synthesis. Elevated VCAM-1 expression is detectable 2 hours following treatment with tumor necrosis factor, is maximal 8 hours following stimulation, and remains elevated for at least 48 hours following stimulation. Rice and Bevilacqua, *Science* 1989, 246, 1303–1306. ICAM-1 expression on endothelial cells is induced by cytokines interleukin-1 tumor necrosis factor and gamma-interferon. Maximal expression of ICAM-1 follows that of ELAM-1 occurring 8 to 10 hours after stimulation and remains elevated for at least 48 hours.

GMP-140 and ELAM-1 are primarily involved in the adhesion of neutrophils to vascular endothelial cells. VCAM-1 primarily binds T and B lymphocytes. In addition, VCAM-1 may play a role in the metastasis of melanoma, and possibly other cancers. ICAM-1 plays a role in adhesion of neutrophils to vascular endothelium, as well as adhesion of monocytes and lymphocytes to vascular endothelium, tissue fibroblasts and epidermal keratinocytes. ICAM-1 also plays a role in T-cell recognition of antigen presenting cell, lysis of target cells by natural killer cells, lymphocyte activation and proliferation, and maturation of T cells in the thymus. In addition, recent data have demonstrated that ICAM-1 is the cellular receptor for the major serotype of rhinovirus, which account for greater than 50% of common colds. Staunton et al., *Cell* 1989, 56, 849–853; Greve et al., *Cell* 1989, 56, 839–847.

It is has been hoped that inhibitors of CAM expression would provide a novel therapeutic class of anti-inflammatory agents with activity towards a variety of inflammatory diseases or diseases with an inflammatory component such as asthma, rheumatoid arthritis, allograft rejections, inflammatory bowel disease, various dermatological conditions, and psoriasis. In addition, inhibitors of ICAM-1, VCAM-1, and ELAM-1 may also be effective in the treatment of colds due to rhinovirus infection, AIDS, Kaposi's sarcoma and some cancers and their metastasis.

In particular, it is has been hoped that inhibitors of CAM expression, particularly ICAM-1 expression, would provide a novel therapeutic class of anti-inflammatory agents with activity towards a variety of inflammatory diseases or diseases with an inflammatory component including central nervous system diseases such as Alzheimer's disease and multiple sclerosis; blood vessel conditions such as vasculitis; eye conditions such as uveitis and herpes keratitis; kidney conditions such as renal allograft rejection and glomeronephritis; lung diseases such as asthma and lung allograft rejection; liver conditions such as liver allograft rejection, viral hepatitis, alcoholic hepatitis and cholangitis; heart diseases such as cardiac allograft rejection and atherosclerosis; joint conditions such as rheumatoid arthritis, thyroid conditions such as Grave's disease and Hashimoto's thyroiditis; gastrointestinal diseases such as inflammatory bowel disease, including colitis, ulcerative colitis, and Crohn's disease; various dermatological conditions, including psoriasis, scleroderma, contact dermatitis, lichen planus, fixed drug eruption, mycosis fungoides and alopecia areata; and various other disorders such as pancreatic and other allograft rejections and graft-versus-host disease.

To date, there are no known therapeutic agents which effectively prevent the expression of the cellular adhesion molecules ELAM-1, VCAM-1 and ICAM-1. The use of neutralizing monoclonal antibodies against ICAM-1 in animal models provide evidence that such inhibitors if identified would have therapeutic benefit for asthma; Wegner et al., *Science* 1990, 247, 456–459, renal allografts; Cosimi et al., *J. Immunol.* 1990, 144, 4604–4612, and cardiac allografts; Isobe et al., *Science* 1992, 255, 1125–1127. The use of a soluble form of ICAM-1 molecule was also effective in preventing rhinovirus infection of cells in culture. Marlin et al., *Nature* 1990, 344, 70–72.

Current agents which affect intercellular adhesion molecules include synthetic peptides, monoclonal antibodies, and soluble forms of the adhesion molecules. Monoclonal antibodies may prove to be useful for the treatment of acute inflammatory response due to expression of ICAM-1, VCAM-1 and ELAM-1. However, with chronic treatment, the host animal develops antibodies against the monoclonal antibodies thereby limiting their usefulness. In addition, monoclonal antibodies are large proteins which may have difficulty in gaining access to the inflammatory site. Soluble forms of the cellular adhesion molecules suffer from many of the same limitations as monoclonal antibodies in addition to the expense of their production and their low binding affinity. Thus, there is a long felt need for molecules which effectively inhibit intercellular adhesion molecules. Antisense oligonucleotides avoid many of the pitfalls of current agents used to block the effects of CAMs.

PCT/US90/02357 (Hession et al.) discloses DNA sequences encoding Endothelial Adhesion Molecules (ELAMs), including ELAM-1 and VCAM-1 and VCAM-1b. A number of uses for these DNA sequences are provided, including (1) production of monoclonal antibody preparations that are reactive for these molecules which may be used as therapeutic agents to inhibit leukocyte binding to endothelial cells; (2) production of ELAM peptides to bind to the ELAM ligand on leukocytes which, in turn, may bind to ELAM on endothelial cells, inhibiting leukocyte binding to endothelial cells; (3) use of molecules binding to ELAMS (such as anti-ELAM antibodies, or markers such as the ligand or fragments of it) to detect inflammation; (4) use of ELAM and ELAM ligand DNA sequences to produce nucleic acid molecules that intervene in ELAM or ELAM ligand expression at the translational level using antisense nucleic acid and ribozymes to block translation of a specific MRNA either by masking MRNA with antisense nucleic acid or cleaving it with a ribozyme. It is disclosed that coding regions are the targets of choice.

There remains a need for therapeutic agents with an enhanced ability to effectively prevent the expression of cellular adhesion molecules. Antisense compounds avoid many of the pitfalls of other agents that could potentially be used to block the effects of cellular adhesion molecules. The present invention is drawn to antisense oligonucleotides which modulate cellular adhesion molecule expression, and methods of using these compounds, including methods of treating diseases associated with cellular adhesion molecules, particularly ICAM-1.

SUMMARY OF THE INVENTION

In accordance with the present invention, antisense compounds are provided which specifically hybridize with a nucleic acid encoding a cellular adhesion molecule (CAM) and which modulate CAM expression, particularly ICAM-1, ELAM-1 and VCAM-1 expression. In preferred embodiments of the invention, the CAM and the nucleic acid encoding it, are those of human ICAM-1. Pharmaceutical compositions comprising the antisense compounds of the invention, and various methods of using the antisense compounds of the invention, are also herein provided. Therapeutic and prophylactic methods which use the compounds and compositions of the invention are also provided.

BRIEF DESCRIPTION OF THE DRAWINGS

FIGS. 1A–1D show the mRNA sequence of human intercellular adhesion molecule-1 (ICAM-1).

FIGS. 2A–2E show the mRNA sequence of human endothelial leukocyte adhesion molecule-1 (ELAM-1).

FIGS. 3A–3D show the mRNA sequence of human vascular cell adhesion molecule-1 (VCAM-1).

DETAILED DESCRIPTION OF THE INVENTION

Figure 4:
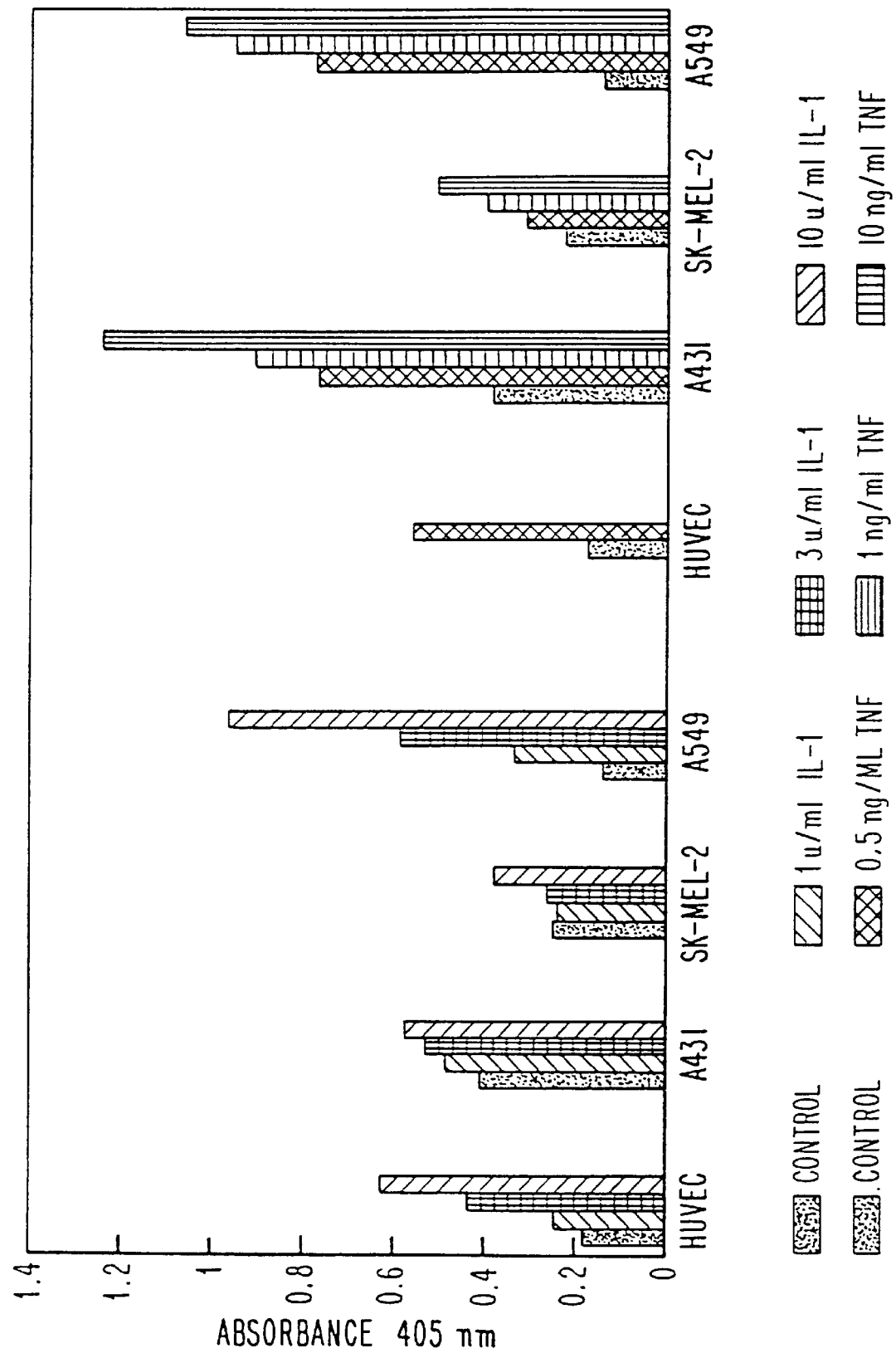
FIG. 4 is a graphical representation of the induction of ICAM-1 expression on the cell surface of various human cell lines by interleukin-1 and tumor necrosis factor.

The present invention employs antisense compounds, particularly oligonucleotides, for use in modulating the function of nucleic acid molecules encoding CAMs, ultimately modulating the amount of CAM produced. This is accomplished by providing oligonucleotides which specifically hybridize with nucleic acids, preferably mRNA, encoding CAMs.

This relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is a nucleic acid encoding a CAM; in other words, a CAM gene or mRNA expressed from a CAM gene. mRNA encoding a CAM, and particularly mRNA encoding ICAM-1, is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleases which form a region known to such persons as the 5'-untranslated region, the 3'-untranslated region, the 5' cap region and intron/exon junction ribonucleases. Thus, oligonucleotides may be formulated in accordance with this invention which are targeted wholly or in part to these associated ribonucleases as well as to the informational ribonucleases. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding ICAM-1, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'—5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of ICAM-1 expression. In the context of this invention "modulation" means either inhibition or stimulation; i.e., either a decrease or increase in expression. This modulation can be measured in ways which are routine in the art, for example by reverse transcriptase PCR, or Northern blot assay of mRNA expression, as taught in the examples of the instant application or by Western blot, immunoprecipitation or ELISA assay of protein expression, or by flow cytometry, as taught in the examples of the instant application.

As a consequence of the association between CAMs and normal and abnormal cell-cell interactions, inhibition of the expression of one or more CAMs is expected to potentially lead to, for example, the inhibition or amelioration of a variety of pathogenic, inflammatory events, tumorigenic and/or metastatic events and, accordingly, results in reduction of the undesirable consequences of such events. Such reduction is desirable for treating (i.e., providing prophylactic, palliative and/or therapeutic effects) various pathogenic, inflammatory and hyperproliferative disorders or diseases. Such inhibition of ICAM-1 is further desirable for preventing or ameliorating the development of such diseases or disorders in an animal suspected of being, or known to be, prone to such diseases or disorders.

The present invention also comprises methods of inhibiting a variety of CAM-mediated pathogenic, inflammatory and tumorigenic and/or metastatic events using the antisense compounds of the invention. Methods of treating conditions in which abnormal or excessive CAM expression and/or CAM-mediated inflammation occurs are also provided. These methods employ the antisense compounds of the invention and are believed to be useful therapeutically and as clinical research and diagnostic tools. The antisense compounds of the present invention may also be used for research purposes. Thus, for example, the specific hybridization exhibited by the antisense oligonucleotides of the present invention may be used for assays, purifications, cellular product preparations and in other methodologies which may be appreciated by persons of ordinary skill in the art.

The oligonucleotides of this invention can be used in diagnostics, therapeutics, prophylaxis, and as research reagents and in kits. Since the oligonucleotides of this invention hybridize to nucleic acids encoding CAMs, sandwich, calorimetric and other assays can easily be constructed to exploit this fact. Provision of means for detecting hybridization of oligonucleotide with a gene or mRNA encoding a CAM can routinely be accomplished. Such provision may include enzyme conjugation, radiolabelling or any other suitable detection systems. Kits for detecting the presence or absence of one or more CAMs may also be prepared.

The present invention is also suitable for diagnosing abnormal inflammatory states in tissue or other samples from patients suspected of having an inflammatory disease. The ability of the oligonucleotides of the present invention to inhibit inflammation may be employed to diagnose such states. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotides means to add the oligonucleotide (s), usually in a liquid carrier, to a cell suspension or tissue sample, either in vitro or ex vivo, or to administer the oligonucleotide(s) to cells or tissues within an animal. Similarly, the present invention can be used to distinguish CAM-associated pathologies from pathologies having other etiologies, in order that an efficacious treatment regimen can be designed. Furthermore, the present invention can be used to distinguish between phenomena and pathologies associated with a particular CAM (e.g., ICAM-1) from phenomena and pathologies associated with another CAM (e.g., VCAM-1).

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases. It is not necessary for all positions in a given compound to be uniformly modified, and in fact more than one of the following modifications may be incorporated in a single antisense compound or even in a single residue thereof, for example, at a single nucleoside within an oligonucleotide.

The antisense compounds in accordance with this invention preferably comprise from about 5 to about 50 nucleobases. Particularly preferred are antisense oligonucleotides comprising from about 8 to about 30 nucleobases (i.e., from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides. Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-51 to 5'-2'. Various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_4$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262. Further teaching of PNA compounds can be found in Nielsen et al. (*Science*, 1991, 254, 1497–1500).

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat.

No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl, O-alkyl-O-alkyl, O-, S-, or N-alkenyl, or O-, S- or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_2ON(CH_3)_2$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta* 1995, 78, 486–504) i.e., an alkoxyalkoxy group.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering* 1990, pages 858–859, Kroschwitz, J. I., ed. John Wiley & Sons, those disclosed by Englisch et al. (*Angewandte Chemie, International Edition* 1991, 30, 613–722), and those disclosed by Sanghvi, Y. S., Chapter 15, *Antisense Research and Applications* 1993, pages 289–302, Crooke, S. T. and Lebleu, B., ed., CRC Press. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications* 1993, CRC Press, Boca Raton, pages 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA* 1989, 86, 6553–6556), cholic acid (Manoharan et al., *Bioorg. Med. Chem. Lett.* 1994, 4, 1053–1059), a thioether, e.g., hexyl-S-tritylthiol (Manoharan et al., *Ann. N.Y. Acad. Sci.* 1992, 660, 306–309; Manoharan et al., *Bioorg. Med. Chem. Let.* 1993, 3, 2765–2770), a thiocholesterol (Oberhauser et al., *Nucl. Acids Res.* 1992, 20, 533–538), an aliphatic chain, e.g., dodecandiol or undecyl residues (Saison-Behmoaras et al., *EMBO J.* 1991, 10, 1111–1118; Kabanov et al., *FEBS Lett.* 1990, 259, 327–330; Svinarchuk et al., *Biochimie* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.* 1995, 36, 3651–3654; Shea et al., *Nucl. Acids Res.* 1990, 18, 3777–3783), a polyamine or a polyethylene glycol chain (Manoharan et al., *Nucleosides & Nucleotides* 1995, 14, 969–973), or adamantane acetic acid (Manoharan et al., *Tetrahedron Lett.* 1995, 36, 3651–3654), a palmityl moiety (Mishra et al., *Biochim. Biophys. Acta* 1995, 1264, 229–237), or an octadecylamine or hexylamino-carbonyl-oxycholesterol moiety (Crooke et al., *J. Pharmacol. Exp. Ther.* 1996, 277, 923–937).

Representative United States patents that teach the preparation of such oligonucleotide conjugates include, but are not limited to, U.S. Pat. Nos.: 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585, 481; 5,587,371; 5,595,726; 5,597,696; 5,599,923; 5,599,928 and 5,688,941.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids. Ribozymes are not comprehended by the present invention.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., 2'-fluoro- or 2'-O-methoxyethyl-substituted). Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl- substituted), or vice-versa. In one embodiment, the oligonucleotides of the present invention contain a 2'-O-methoxyethyl (2'-O—$CH_2CH_2OCH_3$) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—$CH_2CH_2OCH_3$) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also preferred. Chimeric oligonucleotides comprising one or more such modifications are presently preferred.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-O-methoxyethyl oligonucleotides (Martin, P., *Helv. Chim. Acta* 1995, 78, 486–504). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids. "Pharmaceutically acceptable salts" are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," *J. of Pharma Sci.* 1977, 66, 1–19).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems* 1991, 8, 91–192; Muranishi, *Critical Reviews in Therapeutic Drug Carrier Systems* 1990, 7, 1–33). One or more penetration enhancers from one or more of these broad categories may be included. Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems* 1991, page 92; Muranishi, *Critical Reviews in Therapeutic Drug Carrier Systems* 1990, 7, 1; El-Hariri et al., *J. Pharm. Pharmacol.* 1992 44, 651–654). Sodium caprate and sodium laurate are presently preferred, particularly in combination with one or more bile salts.

The physiological roles of bile include the facilitation of dispersion and absorption of lipids and fat-soluble vitamins (Brunton, Chapter 38 In: *Goodman & Gilman's The Pharmacological Basis of Therapeutics*, 9th Ed., Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives. A preferred bile salt is CDCA (Sigma Chemical Co.).

Complex formulations comprising one or more penetration enhancers may be used. For example, bile salts may be used in combination with fatty acids to make complex formulations.

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)[Lee et al., *Critical Reviews in Therapeutic Drug Carrier Systems* 1991, page 92; Muranishi, *Critical Reviews in Therapeutic Drug Carrier Systems* 1990, 7, 1–33; Buur et al., *J. Control Rel.* 1990, 14, 43–51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems* 1991, page 92); and perfluorochemical emulsions, such as FC-43 (Takahashi et al., *J. Pharm. Phamacol.* 1988, 40, 252–257).

Non-surfactants include, for example, unsaturated cyclic ureas, 1-alkyl- and 1-alkenylazacyclo-alkanone derivatives (Lee et al., *Critical Reviews in Therapeutic Drug Carrier Systems* 1991, page 92); and non-steroidal anti-inflammatory agents such as diclofenac sodium, indomethacin and phenylbutazone (Yamashita et al., *J. Pharm. Pharmacol.* 1987, 39, 621–626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinyl-pyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., *Current Op. Biotech.* 1995, 6, 698–708).

The oligonucleotides of the present invention specifically hybridize to nucleic acids (e.g., mRNAs) encoding a CAM protein. The antisense compounds of the present invention can be utilized as therapeutic compounds, as diagnostic tools or research reagents that can be incorporated into kits as well as other methodologies as will be apparent to persons of ordinary skill in the art.

For therapeutic uses, the pharmaceutical compositions of the present invention may be administered in a number of ways depending upon whether local or systemic treatment is desired and upon the area to be treated. Administration may be topical (including ophthalmic and to mucous membranes including vaginal and rectal delivery) pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

For certain conditions, particularly skin conditions including but not limited to, psoriasis, administration of compounds to the skin is preferred. Administration of compounds to the skin may be done in several ways including topically and transdermally. A common requirement for these modes of administration is penetration of the skin's permeability barrier and efficient delivery to the target.A preferred method for the delivery of biologically active substances to the skin is topical administration. "Topical administration" refers to the contacting, directly or otherwise, to all or a portion of the skin of an animal. Topical administration can be used as the route of administration when local delivery of a drug is desired at, or immediately adjacent to, the point of application of the drug composition or formulation. Three general types of topical routes of administration include administration of a drug composition to mucous membranes, skin or eyes. Compositions for topical administration may be a mixture of components or phases as are present in emulsions (including microemulsions and creams), and related formulations comprising two or more phases.delivery of nucleic acids, preferably oligonucleotides, to the epidermis and/or dermis of an animal to increase the bioavailability of the nucleic acid therein. As used herein, the term "bioavailability" refers to the amount of the administered drug therapy (in this case the oligonucleotide) that reaches and acts upon its target. The term is used for drugs whose efficacy is measured relative to the concentration in the blood even though the ultimate site of action of the drug might be outside the blood, e.g., intracellular. (See van Berge-Henegouwen et al., Gastroenterology, 1977: 300).

Transdermal drug delivery is a valuable route for the administration of lipid soluble therapeutics. The dermis is more permeable than the epidermis and therefore absorption is much more rapid through abraded, burned or denuded skin. Inflammation and other physiologic conditions that increase blood flow to the skin also enhance transdermal adsorption. Absorption via this route may be enhanced by the use of an oily vehicle (inunction) or through the use of penetration enhancers. Hydration of the skin and the use of controlled release topical patches are also effective ways to deliver drugs via the transdermal route. This route provides an effective means to deliver drugs for both systemic and local therapy.

In addition, iontophoresis (transfer of ionic solutes through biological membranes under the influence of an electric field) (Lee et al., *Critical Reviews in Therapeutic Drug Carrier Systems*, 1991, p. 163), phonophoresis or sonophoresis (use of ultrasound to enhance the absorption of various therapeutic agents across biological membranes, notably the skin and the cornea) (Lee et al., *Critical Reviews in Therapeutic Drug Carrier Systems*, 1991,p. 166), and optimization of vehicle characteristics relative to dose :deposition and retention at the site of administration (Lee et al., *Critical Reviews in Therapeutic Drug Carrier Systems*, 1991, p. 168) may be useful methods for enhancing the transport of drugs across mucosal sites in accordance with the present invention.

Formulations for topical administration may include transdermal patches, ointments, lotions, creams, emulsions, gels, drops, suppositories, sprays, liquids and powders. Conventional pharmaceutical carriers, aqueous, powder or oily bases, thickeners and the like may be necessary or desirable. Coated condoms, gloves and the like may also be useful. Pharmaceutical compositions for administration of oligonucleotide drugs to the skin may also include solutions, emulsions, and liposome-containing formulations. These compositions may be generated from a variety of components that include, but are not limited to, preformed liquids, self-emulsifying solids and self-emulsifying semisolids. The compositions of the present invention may be formulated into any of many possible dosage forms such as, but not limited to, tablets, capsules, liquid syrups, soft gels, suppositories, and enemas.

Pharmaceutically acceptable organic or inorganic carrier substances suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like. The formulations can be sterilized and, if desired, mixed with auxiliary agents, e.g., lubricants, preservatives, stabilizers, wetting agents, emulsifiers, salts for influencing osmotic pressure, buffers, colorings flavorings and/or aromatic substances and the like which do not deleteriously interact with the nucleic acid(s) of the formulation.

The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The know-how on the preparation of such compositions and formulations is generally known to those skilled in the pharmaceutical and formulation arts and may be applied to the formulation of the compositions of the present invention. Compositions for oral administration include powders or granules, suspensions or solutions in water or non-aqueous media, capsules, sachets or tablets. Enteric coatings may be useful. Thickeners, flavoring agents, diluents, emulsifiers, dispersing aids or binders may be desirable.

For pulmonary administration aerosolization of liquid particles may be preferred; this can be achieved by any suitable means, such as with a nebulizer. See, for example, U.S. Pat. No. 4,501,729. Nebulizers are commercially available devices which transform solutions or suspensions into a therapeutic aerosol mist either by means of acceleration of a compressed gas, typically air or oxygen, through a narrow venturi orifice or by means of ultrasonic agitation. Suitable nebulizers include those sold by Blaire® under the name PARI LC PLUS, PARI DURA-NEB 2000, PARI-BABY Size, PARI PRONEB Compressor with LC PLUS, PARI WALKHALER Compressor/Nebulizer System, PARI LC PLUS Reusable Nebulizer, and PARI LC Jet+ ®Nebulizer. Preferably, liquid or solid aerosols are produced at a rate of from about 10 to 150 liters per minute, more preferably from about 30 to 150 liters per minute, and most preferably about 60 liters per minute. Exemplary formulations for use in nebulizers consist of an oligonucleotide in a liquid, such as sterile, pyragen free water, or saline solution, wherein the oligonucleotide comprises up to about 40% w/w of the formulation. Preferably, the oligonucleotide comprises less than 20% w/w. If desired, further additives such as preservatives (for example, methyl hydroxybenzoate) antioxidants, and flavoring agents can be added to the composition.

Solid particles comprising an oligonucleotide can also be aerosolized using any solid particulate medicament aerosol generator known in the art. Such aerosol generators produce respirable particles, as described above, and further produce reproducible metered dose per unit volume of aerosol. Suitable solid particulate aerosol generators include insufflators and metered dose inhalers.

Compositions for parenteral administration may include sterile aqueous solutions which may also contain buffers, diluents and other suitable additives.

In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly anticancer or anti-inflammatory agents.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in vitro and in in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

Thus, in the context of this invention, by "therapeutically effective amount" is meant the amount of the compound which is required to have a therapeutic effect on the treated individual. This amount, which will be apparent to the skilled artisan, will depend upon the age and weight of the individual, the type of disease to be treated, perhaps even the gender of the individual, and other factors which are routinely taken into consideration when designing a drug treatment. A therapeutic effect is assessed in the individual by measuring the effect of the compound on the disease state in the animal. For example, if the disease to be treated is cancer, therapeutic effects are assessed by measuring the rate of growth or the size of the tumor, or by measuring the production of compounds such as cytokines, production of which is an indication of the progress or regression of the tumor.

The antisense compounds of the invention result in immunosuppressive and anti-inflammatory effects in vivo and may be used by those skilled in the art to provide prophylactic, palliative and therapeutic benefit to an animal, including a human, in need of such effects. The antisense compounds of the invention are also evaluated for their ability to inhibit the metastasis of cancer cells and are used to provide prophylactic, palliative or therapeutic relief from hyperproliferative disorders. Therapeutic methods using the antisense compounds of the invention include, but are not limited to, the following:

Immunoresponsive events that are mediated or influenced, either directly or indirectly, by a cellular adhesion molecule in an animal may be modulated by oligonucleotides of the present invention. Such immunoresponsive events can lead to undesirable effects such as, e.g., inflammation. The method of modulating immunoresponsive events mediated or influenced by a cellular adhesion molecule, particularly ICAM-1, comprises administering one or more of the antisense compounds of the invention (or a combination thereof with one or more anti-inflammatory or immunosuppressive non-antisense-based agents or NABAs; see below), in a pharmaceutical preparation if required, to the animal. Some specific therapeutic modalities for the antisense compounds of the invention follow as examples but are not intended to limit the scope of the invention.

Diapedesis, the transendothelial migration of immunoresponsive cells (such as leukocytes) from the circulatory system into injured or infected tissues, is thought to be a key event in inflammatory injury (for a review, see Albelda et al., *FASEB J.*, 1994, 8, 504). Administration of the antisense compounds of the invention, as part of an appropriate pharmaceutical composition if required, to an animal is expected to inhibit diapedesis and subsequent undesired immunoresponsive events such as, for example, inflammation and inflammatory damage. Such treatment may be in combination with one or more anti-inflammatory and/or immunosuppressive drugs (see below). Such administration can be systemic or directly to the site(s) of diapedesis, inflammation and/or inflammatory damage. The antisense compounds of the invention are evaluated for their ability to modulate diapedesis and subsequent undesired inflammation and/or inflammatory damage using, for example, the assays described in the references cited in this section, or in the in vitro flow model of Luscinskas et al. (*J. Immunol.*, 1996, 157, 326), and/or appropriate animal models.

The present invention also provides a method of avoiding allograft rejection including treating or preventing graft versus host disease (GVHD) in an animal comprising administering one or more of the antisense compounds of the invention, or a combination thereof with one or more anti-inflammatory or immunosuppressive agents, in a pharmaceutical preparation if required, to the animal. Such administration can be systemic or directly to the area(s) of the transplanted tissue(s) or organ(s), or administered ex vivo to tissue(s) or organ(s) prior to their transplantation. Such treatment may be in combination with one or more anti-inflammatory and/or immunosuppressive drugs (see below). The antisense compounds of the invention are evaluated for their ability to modulate allograft rejection using one or more assays known in the art and/or one or more appropriate animal models (see, e.g., Stepkowski et al., *J. Immunol.*, 1994, 153, 5336, and Example 21 in U.S. Pat. No. 5,514,788 to Bennett et al.).

The present invention also provides a method of treating various forms of arthritis in an animal comprising administering one or more of the antisense compounds of the invention, or a combination thereof with one or more anti-inflammatory or immunosuppressive agents, in a pharmaceutical preparation if required, to the animal. Such administration can be systemic or directly to involved tissues such as, e.g., synovial fluid. Increased expression of cellular adhesion molecules, including ELAM-1, VCAM-1, ICAM-1 and PECAM-1, has been detected in synovial fluid from patients having rheumatoid arthritis (Tak et al., *Clin. Immunol. Immunopathol.*, 1995, 77, 236). Such forms of arthritis include, for example, autoimmune forms of arthritis, including some forms of rheumatoid arthritis (RA), psoriatic arthritis (PA) and ankylosing spondylitis (AS); non-autoimmune forms of RA, PA and AS; infectious arthritis, such as results from infection with spirochetes (Lyme Disease, also known as LD or Lyme Arthritis, is caused by *Borrelia burgdorferi*, and some instances of Reiter's Syndrome, RS, appear to be associated with *Chlamydia trachomatis*), bacterial infection (staphylococci such as *Hemophilus influenzae*, streptococci, pneumococci, gram-negative bacilli and the like), viral infection (e.g., rubella, mumps, human parvovirus or hepatitis B), and/or fungal infection (e.g., *Sporothrix schenckii, Coccidioides immitis, Blastomyces dermatididis* or *Candida albicans*) (see *The Merck Manual of Diagnosis and Therapy*, 15th Ed., pp. 1239–1267, Berkow et al., eds., Rahay, N.J., 1987). Such treatment may be in combination with one or more additional anti-inflammatory and/or immunosuppressive drugs and, additionally or alternatively, when the arthritis to be treated results at least in part from infection of the animal by a pathogen, with one or more antibiotics (see below). The antisense compounds of the invention are evaluated for their ability to modulate arthritis and inflammatory damage resulting therefrom using one or more assays known in the art and/or one or more appropriate animal models (see, e.g., published PCT application No. WO 95/32285 to Benoist et al.).

The present invention also provides a method of treating various inflammatory disorders of the bowel in an animal comprising administering one or more of the antisense compounds of the invention, or a combination thereof with one or more anti-inflammatory or immunosuppressive agents, in a pharmaceutical preparation if required, to the animal. Such disorders include, for example, Crohn's disease and other forms of regional enteritis; and various forms of colitis including ulcerative colitis and granulomatous, ischemic and radiation colitis (see *The Merck Manual of Diagnosis and Therapy*, 15th Ed., pp. 797–806, Berkow et al., eds., Rahway, N.J., 1987). Such treatment may be in combination with one or more additional antisense compounds or anti-inflammatory and/or immunosuppressive drugs (see below). The antisense compounds of the invention are evaluated for their ability to modulate a inflammatory disorder of the bowel using one or more assays known in the art and/or one or more appropriate animal models (see, e.g., Example 20 in U.S. Pat. No. 5,514,788 to Bennett et al. and Okayasu et al., *Gastroenterol.*, 1990, 98, 694).

The present invention also provides a method of treating various autoimmune diseases and disorders including but not limited to autoimmune thyroid disorders; autoimmune forms of arthritis; multiple sclerosis; some forms of juvenile diabetes mellitus; myasthenia gravis; pemphigus vulgaris; and systemic lupus erythematosus (SLE or lupus) (for a review of autoimmune disorders, see Steinman, *Sci. Amer.*, 1993, 269, 107). Administration of the antisense compounds of the invention, as part of an appropriate pharmaceutical composition if required, to an animal is expected to prevent or inhibit the development of the autoimmune disease and subsequent undesired events. Such treatment may be in combination with one or more anti-inflammatory and/or immunosuppressive drugs. Such administration can be systemic or directly to a specific tissue, depending on the nature of the disorder. The antisense compounds of the invention are evaluated for their ability to prevent or inhibit autoimmune diseases using appropriate assays and animal models known to those skilled in the art (see, for example, Burkhardt et al., *Rheumatol. Int.*, 1997, 17, 91).

The present invention provides a method of modulating undesirable events that are mediated or influenced, either directly or indirectly, by cellular adhesion molecules in an animal during or following cardiovascular injury or during the course of a cardiovascular disease or disorder. Some specific therapeutic modalities for the antisense compounds of the invention follow as examples but are not intended to limit the scope of the invention.

The present invention provides a method of reducing or preventing myocardial ischemia/reperfusion (MI/R) injury in an animal comprising administering one or more of the antisense compounds of the invention, or a combination thereof with one or more anti-inflammatory or immunosuppressive agents, in a pharmaceutical preparation if required, to the animal. Coronary artery reperfusion is an effective treatment for patients with acute myocardial infarction. However, reperfusion itself often leads to enhanced injury of myocardial tissue. Transmigration of PMNs into the ischemic myocardium is believed to play some role in myocardial ischemia/reperfusion injury (Entman et al., *FASEB J.*, 1991, 5, 2529; Lefer et al., *FASEB J.*, 1991, 5, 2029). ICAMI-1 is up-regulated in myocardial tissue isolated from human hearts failing from either dilated cardiomyopathy, acute myocarditis or ischemic heart disease (Devaux et al., *European Heart J.*, 1997, 18, 470). Administration of the antisense compounds of the invention, as part of an appropriate pharmaceutical composition if required, to an animal is expected to modulate MI/R injury. Such administration can be systemic or directly to the circulatory system. The antisense compounds of the invention are evaluated for their ability to modulate MI/R injury using one or more assays known in the art and/or one or more appropriate animal models such as, e.g., those described in the references cited in this section.

The present invention provides a method of reducing leukocyte-induced damage in an animal during or following a stroke or series of strokes, or of preventing leukocyte-induced damage from a stroke in an animal known to be prone to having strokes, in an animal comprising administering one or more of the antisense compounds of the invention, in a pharmaceutical preparation if required, to the animal. A stroke is a blockage or hemorrhage of a blood vessel in or leading to the brain (e.g., aneurysmal subarachnoid hemorrhage) that causes inadequate blood supply (ischemia) to the brain. After brain ischemia, leukocytes adhere to the perturbed vascular endothelium and are believed to aggravate reperfusion injury eventually leading, in some cases, to chronic vasospasm (i.e., a sudden constriction of an artery or vein), which in turn can have serious and undesired consequences. Adhesion molecules, including ICAM-1, are up-regulated in acute infarctions from brain sections of human subjects who died within 18 days of ischemic stroke (Lindsberg et al., *Circ.*, 1996, 94, 939). In an animal model, a monoclonal antibody to ICAM-1 inhibited vasospasm (Oshiro et al., Stroke, 1997, 28, 2031). Administration of the antisense compounds of the invention, as part of an appropriate pharmaceutical composition if required, to an animal is expected to stroke-related injuries. Such administration can be systemic or directly to the circulatory system. The antisense compounds of the invention are evaluated for their ability to modulate stroke-related injury using one or more assays known in the art and/or one or more appropriate animal models such as, for example, those described in the references cited in this section.

Patients having hyperproliferative disorders, which include both benign tumors and primary malignant tumors that have been detected early in the course of their development, may often be successfully treated by the surgical removal of the benign or primary tumor. If unchecked, however, cells from malignant tumors are spread throughout a patient's body through the processes of invasion and metastasis. Invasion refers to the ability of cancer cells to detach from a primary site of attachment and penetrate, e.g., an underlying basement membrane. Metastasis indicates a sequence of events wherein (1) a cancer cell detaches from its extracellular matrices, (2) the detached cancer cell migrates to another portion of the patient's body, often via the circulatory system, and (3) attaches to a distal and inappropriate extracellular matrix, thereby created a focus from which a secondary tumor can arise. Normal cells do not possess the ability to invade or metastasize and/or undergo apoptosis (programmed cell death) if such events occur (Ruoslahti, *Sci. Amer.*, 1996, 275, 72).

Disseminating precancerous or cancerous cells often display ectopic expression of adhesion molecules which may facilitate step (3) of the metastatic process as described above. Examples of such adhesion molecules include ICAM-1 and other CAMs (for a review, see Tang et al., *Invasion Metastasis*, 1994, 14, 109). Thus, modulation of ICAM-1 using the antisense compounds of the invention may result in a decreased ability of disseminating cancer cells to attach to a distal and/or inappropriate matrix, thereby modulating metastasis of the primary tumor. The present invention thus also provides a method of modulating or preventing metastasis in an animal comprising administering one or more of the antisense compounds of the invention, in a pharmaceutical preparation if required, to the animal. Such treatment may be in combination with one or more additional anticancer antisense compounds and/or chemotherapeutic drugs. The antisense compounds of the invention are evaluated for their ability to modulate metastasis using one or more assays known in the art and/or one or more appropriate animal models (see, e.g., Examples 16–18 in U.S. Pat. No. 5,514,788 to Bennett et al.).

If desired, the therapeutic antisense modulation of the expression of cellular adhesion molecules can be combined with additional therapies in order to achieve a requisite level of interference with, or prevention of, undesirable disorders or diseases. Such combinations can be carried out, for example, by simultaneously administering two or more antisense compounds targeted to one or more CAM, or, in treating an animal having inflammation, an antisense compound targeted to a CAM in combination with a non-antisense-based anti-inflammatory or immunosuppressive agent. If an animal having a hyperproliferative disease or disorder is to be treated, the antisense compound targeted to a CAM may be combined with a second anticancer agent, which may be a second antisense compound or a non-antisense-based agent. When used with the antisense compounds of the invention, such second agents may be used in simple combination, sequentially, or in combination with one or more other such non-antisense-based agents or physical treatments such as radiation therapy. When two (or more) antisense compounds, or a combination of one or more antisense compounds and one or more other chemotherapeutic agents, are to be administered simultaneously in a treatment regime, one preferred composition is one comprising a lipid vesicle, particularly a sterically stabilized lipid vesicle, comprising both (or all) of the compounds. In the context of the invention, the term "treatment regimen" is meant to encompass therapeutic, palliative and prophylactic modalities.

Two or more antisense compounds can be administered simultaneously as described above. Combination treatments can also be carried out by first (1) administering a first composition comprising a first antisense compound targeted to a cellular adhesion molecule (or a combination thereof with one or more anti-inflammatory, immunosuppressive and/or chemotherapeutic agents) for a first period of time and then (2) "switching" to administration of a second composition comprising a second antisense compound targeted to a cellular adhesion molecule (or a combination thereof with one or more anti-inflammatory or chemotherapeutic agents) for a second period of time.

For the purpose of treating hyperproliferative disorders, the antisense compounds of the invention can additionally or alternatively be used in combination with non-antisense-based chemotherapeutic agents. Examples of such agents that can be used in combination with the antisense compounds of the invention include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, nitrogen mustards, melphalan, methylcyclohexylnitrosurea, cyclophosphamide, 6-mercaptopurine, 6-thioguanine, cytarabine (CA), 5-azacytidine, hydroxyurea, deoxycoformycin, colchicine, 5-fluorouracil (5-FU), 4-hydroxyperoxycyclophosphoramide, 5-fluorodeoxyuridine (5-FUdR), methotrexate (MTX), vincristine, vinblastine, etoposide, trimetrexate, teniposide, cisplatin and diethylstilbestrol (DES). (See, generally, *The Merck Manual of Diagnosis and Therapy*, 15th Ed., pp. 1206–1228, Berkow et al., eds., Rahway, N.J., 1987).

The compounds of the invention can also be used in combination with anti-inflammatory and/or immunosuppressive agents. Examples of non-antisense-based anti-inflammatory or immunosuppressive agents that can be used in combination with the antisense compounds of the invention include but are not limited to salicylates; nonsteroidal anti-inflammatory drugs (NSAIDs), including indomethacin, ibuprofen, fenopofen, ketoprofen, naproxen, piroxicam, phenylbutazone, oxyphenbutazone, sulindac and meclofenamate; gold compounds, such as auranofin; D-penicillamine; cyclophosphamide; methotrexate; azathioprine; colchicine; hydroxychloroquine; corticotropin; steroids and corticosteroids such as, for example, hydrocortisone, deoxyhydrocortisone, fludrocortisone, prednisolone, methylprednisolone, prednisone, triamcinolone, dexamethasone, betamethasone and paramethasone. See, generally, *The Merck Manual of Diagnosis and Therapy*, 15th Ed., pp. 1239–1267 and 2497–2506, Berkow et al., eds., Rahway, N.J., 1987).

Antisense compounds of the invention may also be administered in combination with anti-infective drugs. Some forms of arthritis result from infection of an animal by a pathogen, such as a bacteria or spirochete, and subsequent immune system-mediated events, e.g., inflammation. An observation that may at least partially explain such undesirable immune responses is that extracts of the arthritis-related spirochete *Borrelia burgdorferi* induce the up-regulation of several cellular adhesion molecules (including ICAM-1, VCAM-1, E-selectin and P-selectin) on bEND.3 cells, an effect that is blocked by the anti-inflammatory agent prednisolone (Hurtenbach et al., *Int. J. Inmmunopharmacol.*, 1996, 18, 281; Boggemeyer et al., *Cell. Adhes. Commun.*, 1994, 2, 145). The present invention provides a method of treating spirochetal infection of an animal comprising administering one or more of the antisense compounds of the invention to an animal, in a pharmaceutical preparation if required.

If the undesired inflammation results from infection from a pathogen one or more antibiotics may also be used in combination with an antisense compound of the invention with or without an anti-inflammatory or immunosuppressive agent. The choice of antibiotic(s) to be used will depend on the nature of the pathogen(s) (i.e., bacteria such as cocci, bacilli, etc. or spirochetes). Such antibiotics include but are not limited to nafcillin (gram-positive cocci); penicillin G (gram-negative cocci); gentamicin and/or piperacillin (gram-negative bacilli); and one or more tetracyclines, one or more penicillin derivatives, erythromycin, doxycycline, chloramphenicol and/or streptomycin (spirochetes such as, e.g., *Borrelia burgdorferi* and *Treponema pallidum*). See, generally, *The Merck Manual of Diagnosis and Therapy*, 15th Ed., pp. 132–136, 236–243, 1239–1267 and 1918–1919, Berkow et al., eds., Rahway, N.J., 1987). One skilled in the art will appreciate that, depending on the cause and stage of development of an undesired immune response resulting from pathogenic infection, it may be preferable in some instances to administer, either simultaneously or sequentially, more complex combinations. That is, the present invention encompasses more complex compositions and treatment regimes such as those comprising, for example, (1) one or more antisense compounds targeted to ICAM-1, (2) one or more antibiotics, and (3) one or more anti-inflammatory/immunosuppressive drugs.

The oligonucleotides of the present invention can be used to detect the presence of CAM-specific nucleic acids in a cell or tissue sample. For example, radiolabeled oligonucleotides can be prepared by $^{32}$P labeling at the 5' end with polynucleotide kinase. (Sambrook et al., *Molecular Cloning. A Laboratory Manual*, Cold Spring Harbor Laboratory Press, 1989, Volume 2, pg. 10.59.) Radiolabeled oligonucleotides are then contacted with cell or tissue samples suspected of containing CAM mRNAs (and thus CAM protein), and the samples are washed to remove unbound oligonucleotide. Radioactivity remaining in the sample indicates the presence of bound oligonucleotide, which in turn indicates the presence of nucleic acids complementary to the oligonucleotide, and can be quantitated using a scintillation counter or other routine means. Expression of nucleic acids encoding these proteins is thus detected.

Radiolabeled oligonucleotides of the present invention can also be used to perform autoradiography of tissues to determine the localization, distribution and quantitation of CAM proteins for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing a CAM gene. Quantitation of the silver grains permits detection of the expression of mRNA molecules encoding these proteins and permits targeting of oligonucleotides to these areas.

Analogous assays for fluorescent detection of expression of CAM nucleic acids can be developed using oligonucleotides of the present invention which are conjugated with fluorescein or other fluorescent tags instead of radiolabeling. Such conjugations are routinely accomplished during solid phase synthesis using fluorescently-labeled amidites or controlled pore glass (CPG) columns. Fluorescein-labeled amidites and CPG are available from, e.g., Glen Research, Sterling Va. Other means of labeling oligonucleotides are known in the art (see, e.g., Ruth, Chapter 6 In: *Methods in Molecular Biology*, Vol. 26: *Protocols for Oligonucleotide Conjugates*, Agrawal, ed., Humana Press Inc., Totowa, N.J., 1994, pages 167–185).

Kits for detecting the presence or absence of expression of an ICAM-1 protein may also be prepared. Such kits include an oligonucleotide targeted to an appropriate gene, i.e., a gene encoding a CAM protein. Appropriate kit and assay formats, such as, e.g., "sandwich" assays, are known in the art and can easily be adapted for use with the antisense compounds of the invention. Hybridization of the antisense compounds of the invention with a nucleic acid encoding a CAM protein can be detected by means known in the art. Such means may include conjugation of an enzyme to the oligonucleotide, radiolabelling of the oligonucleotide or any other suitable detection systems.

The following examples illustrate the invention and are not intended to limit the same.

EXAMPLES

Example 1

Nucleoside Phosphoramidites for Oligonucleotide Synthesis

Deoxy and 2'-alkoxy amidites

2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506, 351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research*, 21, 3197 (1993)] using commercially available phosphoramidites (Glen Research, Inc., Sterling Va. or ChemGenes, Needham Mass.).

2'-Fluoro Aamidites

2'-Fluorodeoxyadenosine amidites

2'-fluoro oligonucleotides were synthesized as described previously [Kawasaki, et. al., *J. Med. Chem.*, 36, 831 (1993)] and U.S. Pat. No. 5,670,633, herein incorporated by reference. Briefly, the protected nucleoside $N^6$-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus $N^6$-benzoyl-9-beta-D-arabinofuranosyladenine was selectively protected in moderate yield as the 3',5'-ditetrahydropyranyl (THP) intermediate. Deprotection of the THP and $N^6$-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'-phosphoramidites.

2'-Fluorodeoxycytidine

2'-deoxy-2'-fluorocytidine was synthesized via amination of 2'-deoxy-2'-fluorouridine, followed by selective protection to give $N^4$-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites are prepared as follows, or alternatively, as per the methods of Martin, P., *Helvetica Chimica Acta*, 78, 486 (1995).

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The 10 residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) hin CH$_3$CN (1 L), cooled to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N$^4$-Benzoyl-2'-O-methoxyethyl-5'-O-dimethoxytrityl-5-methyl cytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N$^4$-Benzoyl-2'-O-methoxyethyl-5'-O-dimethoxytrityl-5-methylcytidine-3'-amidite N$^4$-Benzoyl-2'-O-methoxyethyl-5'-O-dimethoxytrityl-5-methylcytidine (74 g, 0.10 M) was dissolved in CH$_2$Cl$_2$ (1 L) Tetrazole diisopropylamine (7.1 g) and 2-cyanoethoxytetra(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc\Hexane (3:1) as the eluting solvent. The pure fractions were combined to give 90.6 g (87%) of the title compound.

2'-(Aminooxyethyl) Nucleoside Amidites and 2'-(dimethylaminooxyethyl) Nucleoside Amidites Aminooxyethyl and dimethylaminooxyethyl amidites are prepared as per the methods of U.S. patent applications Ser. No. 10/037,143, filed Feb. 14, 1998, and Ser. No. 09/016,520, filed Jan. 30, 1998, each of which is herein incorporated by reference.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide (Beaucage reagent) in acetonitrile for the stepwise thiation of the phosphite linkages. The thiation wait step was increased to 68 sec and was followed by the capping step. After cleavage from the controlled pore glass column and deblocking in concentrated ammonium hydroxide at 55° C. (18 hr), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. Nos. 5,256,775 or U.S. Pat. No. 5,366,878, herein incorporated by reference.

Alkylphosphorothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligo-nucleosides, also identified as amide-4 linked oligonucleo-sides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 4, 5 (1996). They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers."

[2'-O-Me]—[2'-deoxy]—[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 Ammonia/Ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligonucleotide recovered is then analyzed spectrophotometrically for yield and for purity by capillary electrophoresis and by mass spectrometer.

[2'-O-(2-Methoxyethy)]—[2'-deoxy]—[2'-O-(Methoxyethyl)] Chimeric Phosphorothioate Oligonucleotides

[2'-O-(2-methoxyethyl)]—[2'-deoxy]—[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]—[2'-deoxy Phosphorothioate]—[2'-O-(2-Methoxyethyl) Phosphodiester] Chimeric Oligonucleotide

[2'-O-(2-methoxyethyl phosphodiester]—[2'-deoxy phosphorothioate]—[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{-}$P nuclear magnetic resonance spectroscopy, and for some studies oligonucleotides were purified by HPLC, as described by Chiang et al., *J. Biol. Chem.* 266, 18162 (1991). Results obtained with HPLC-purified material were similar to those obtained with non-HPLC purified material.

Example 7

Cellular Assay for ICAM-1, VCAM-1 and ELAM-1 Expansion

Expression of ICAM-1, VCAM-1 and ELAM-1 on the surface of cells can be quantitated using specific monoclonal antibodies in an ELISA. Cells are grown to confluence in 96 well microtiter plates. The cells are stimulated with either interleukin-1 or tumor necrosis factor for 4 to 8 hours to quantitate ELAM-1 and 8 to 24 hours to quantitate ICAM-1 and VCAM-1. Following the appropriate incubation time with the cytokine, the cells are gently washed three times with a buffered isotonic solution containing calcium and magnesium such as Dulbecco's phosphate buffered saline (D-PBS). The cells are then directly fixed on the microtiter plate with 1 to 2% paraformaldehyde diluted in D-PBS for 20 minutes at 25° C. The cells are washed again with D-PBS three times. Nonspecific binding sites on the microtiter plate are blocked with 2% bovine serum albumin in D-PBS for 1 hour at 37° C. Cells are incubated with the appropriate monoclonal antibody diluted in blocking solution for 1 hour at 37° C. Unbound antibody is removed by washing the cells three times with D-PBS. Antibody bound to the cells is detected by incubation with a 1:1000 dilution of biotinylated goat anti-mouse IgG (Bethesda Research Laboratories, Gaithersberg, Md.) in blocking solution for 1 hour at 37° C. Cells are washed three times with D-PBS and then incubated with a 1:1000 dilution of streptavidin conjugated to 9-galactosidase (Bethesda Research Laboratories) for 1 hour at 37° C. The cells are washed three times with D-PBS for 5 minutes each. The amount of β-galactosidase bound to the specific monoclonal antibody is determined by developing the plate in a solution of 3.3 mM chlorophenolred-β-D-galactopyranoside, 50 mM sodium phosphate, 1.5 mM $MgCl_2$; pH=7.2 for 2 to 15 minutes at 37° C. The concentration of the product is determined by measuring the absorbance at 575 nm in an ELISA microtiter plate reader.

An example of the induction of ICAM-1 observed following stimulation with either interleukin-1β or tumor necrosis factor α in several human cell lines is shown in FIG. 4. Cells were stimulated with increasing concentrations of interleukin-1 or tumor necrosis factor for 15 hours and processed as described above. ICAM-1 expression was determined by incubation with a 1:1000 dilution of the monoclonal antibody 84H10 (Amac Inc., Westbrook, Me.). The cell lines used were passage 4 human umbilical vein endothelial cells (HUVEC), a human epidermal carcinoma cell line (A431), a human melanoma cell line (SK-MEL-2) and a human lung carcinoma cell line (A549). ICAM-1 was induced on all the cell lines, however, tumor necrosis factor was more effective than interleukin-1 in induction of ICAM-1 expression on the cell surface (FIG. 4).

Figure 5:
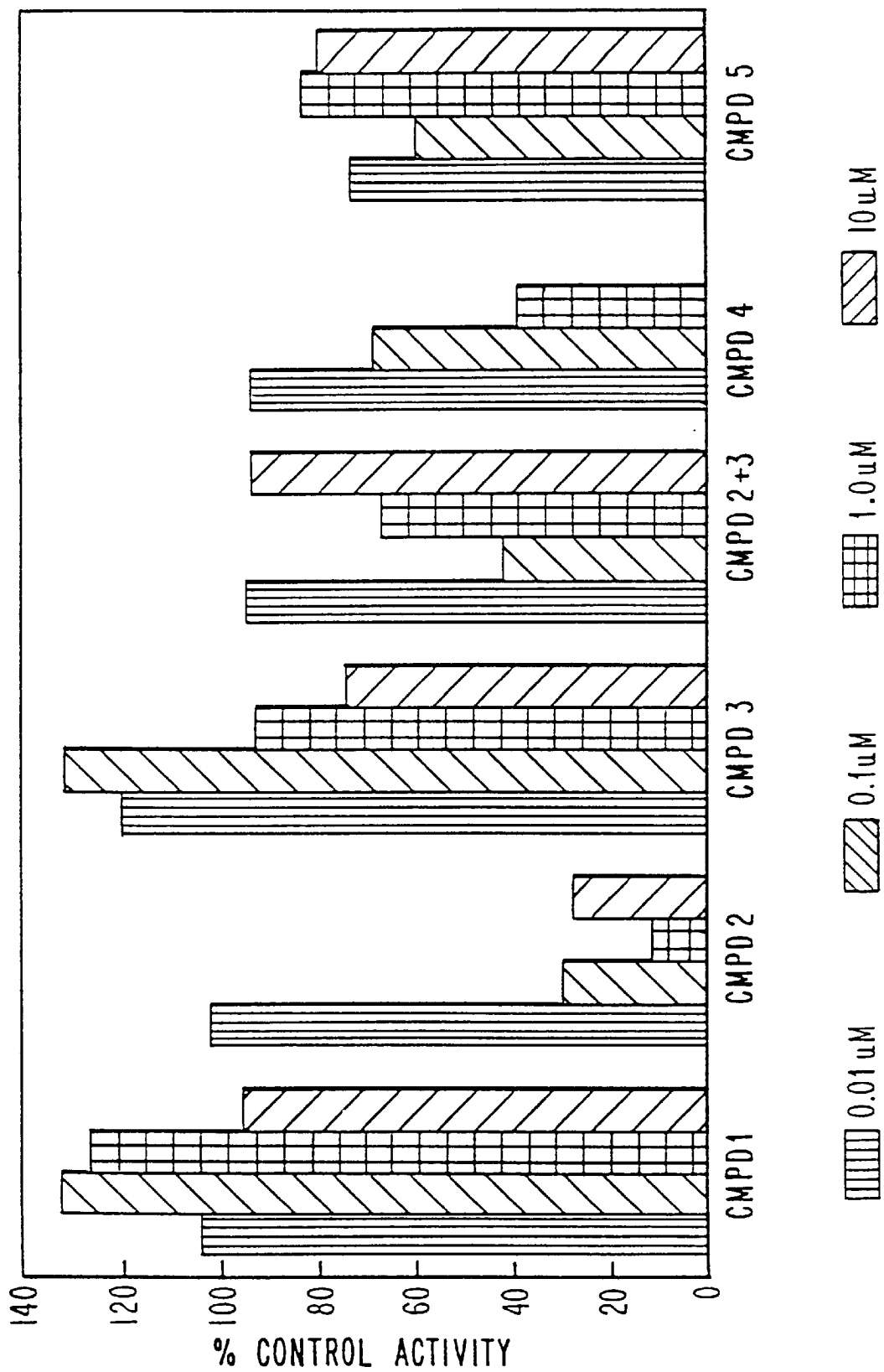
FIG. 5 is a graphical representation of the effects of selected antisense oligonucleotides on ICAM-1 expression on human umbilical vein endothelial cells.

Screening antisense oligonucleotides for inhibition of ICAM-1, VCAM-1 or ELAM-1 expression is performed as described above with the exception of pretreatment of cells with the oligonucleotides prior to challenge with the cytokines. An example of antisense oligonucleotide inhibition of ICAM-1 expression is shown in FIG. 5. Human umbilical vein endothelial cells (HUVEC) were treated with increasing concentration of oligonucleotide diluted in Opti MEM (GIBCO, Grand Island, N.Y.) containing 8 μM N-[1-(2,3-dioleyloxy)propyl]-N,N,N-trimethylammonium chloride (DOTMA) for 4 hours at 37° C. to enhance uptake of the oligonucleotides. The medium was removed and replaced with endothelial growth medium (EGM-UV; Clonetics, San Diego, Calif.) containing the indicated concentration of oligonucleotide for an additional 4 hours. Interleukin-1β was added to the cells at a concentration of 5 units/ml and incubated for 14 hours at 37° C. The cells were quantitated for ICAM-1 expression using a 1:1000 dilution of the monoclonal antibody 84H10 as described above. The oligonucleotides used were;

COMPOUND 1—(ISIS 1558) a phosphodiester oligonucleotide designed to hybridize with position 64–80 of the mRNA covering the AUG initiation of translation codon aving the sequence

5'-TGGGAGCCATAGCGAGGC-3' (SEQ ID NO: 1).

COMPOUND 2—(ISIS 1570) a phosphorothioate containing oligonucleotide corresponding to the same sequence as COMPOUND 1.

COMPOUND 3—a phosphorothioate oligonucleotide complementary to COMPOUND 1 and COMPOUND 2 exhibiting the sequence

5'-GCCTCGCTATGGCTCCCA-3' (SEQ ID NO: 81).

COMPOUND 4—(ISIS 1572) a phosphorothioate containing oligonucleotide designed to hybridize to positions 2190–2210 of the mRNA in the 3' untranslated region containing the sequence

5'-GACACTCAATAAATAGCTGGT-3' (SEQ ID NO: 3).

COMPOUND 5—(ISIS 1821) a phosphorothioate containing oligonucleotide designed to hybridize to human 5-lipoxygenase mRNA used as a control containing the sequence

5'-CATGGCGCGGGCCGCGGG-3' (SEQ ID NO: 82).

The phosphodiester oligonucleotide targeting the AUG initiation of translation region of the human ICAM-1 mRNA (COMPOUND 1) did not inhibit expression of ICAM-1; however, the corresponding phosphorothioate containing oligonucleotide (COMPOUND 2) inhibited ICAM-1 expression by 70% at a concentration of 0.1 μM and 90% at 1 μM concentration (FIG. 4). The increased potency of the phosphorothioate oligonucleotide over the phosphodiester is probably due to increased stability. The sense strand to COMPOUND 2, COMPOUND 3, modestly inhibited ICAM-1 expression at 10 μM. If COMPOUND 2 was prehybridized to COMPOUND 3 prior to addition to the cells, the effects of COMPOUND 2 on ICAM-1 expression were attenuated suggesting that the activity of COMPOUND 2 was due to antisense oligonucleotide effect, requiring hybridization to the mRNA. The antisense oligonucleotide directed against 3' untranslated sequences (COMPOUND 4) inhibited ICAM-1 expression 62% at a concentration of 1 μM (FIG. 5). The control oligonucleotide, targeting human 5-lipoxygenase (COMPOUND 5) reduced ICAM-1 expression by 20%. These data demonstrate that oligonucleotides are capable of inhibiting ICAM-1 expression on human umbilical vein endothelial cells and suggest that the inhibition of ICAM-1 expression is due to an antisense activity.

Figure 6A:
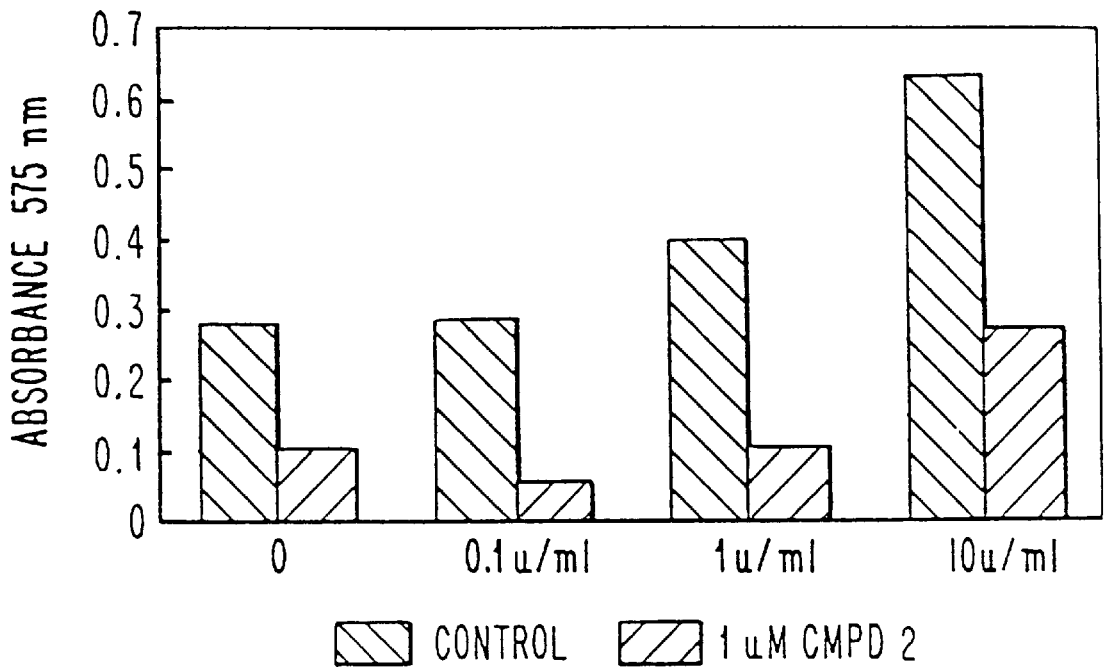
FIGS. 6A and 6B are a graphical representation of the effects of an antisense oligonucleotide on the expression of ICAM-1 in human umbilical vein endothelial cells stimulated with tumor necrosis factor and interleukin-1.
Figure 6B:
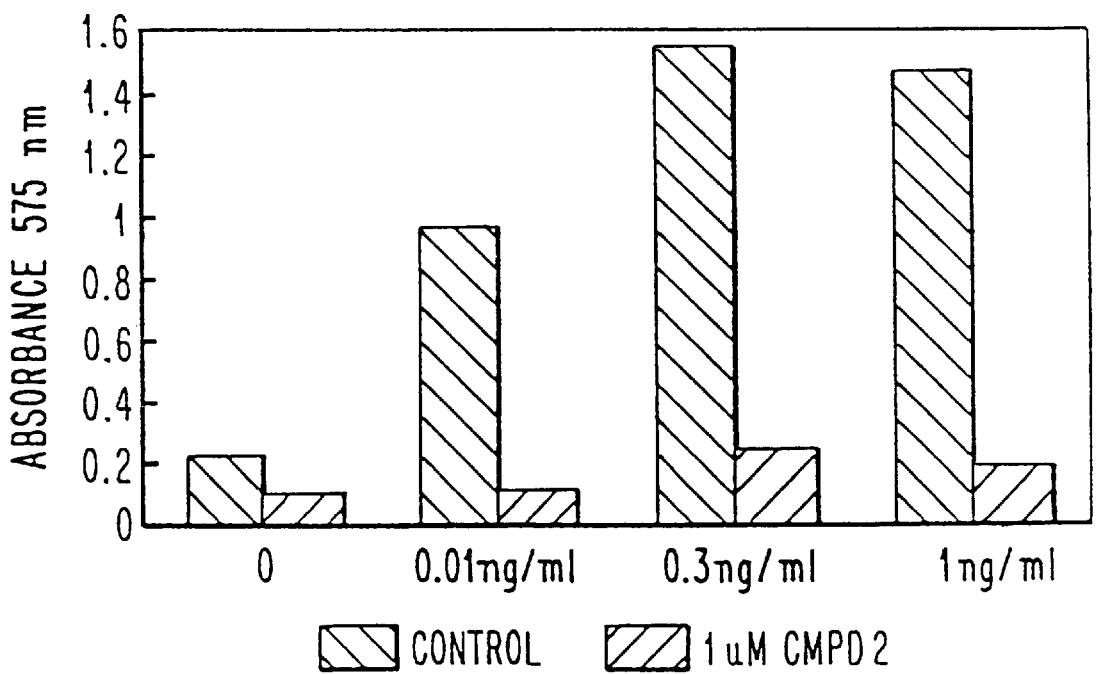

The antisense oligonucleotide COMPOUND 2 at a concentration of 1 μM inhibits expression of ICAM-1 on human umbilical vein endothelial cells stimulated with increasing concentrations of tumor necrosis factor and interleukin-1 (FIG. 6). These data demonstrate that the effects of COMPOUND 2 are not specific for interleukin-1 stimulation of cells.

Analogous assays can also be used to demonstrate inhibition of ELAM-1 and VCAM-1 expression by antisense oligonucleotides.

Example 8

Cellular Assay for Effects of Antisense Oligonucleotides on ICAM-1, VCAM-1 and ELAM-1 Expansion A second cellular assay which can be used to demonstrate the effects of antisense oligonucleotides on ICAM-1, VCAM-1 or ELAM-1 expression is a cell adherence assay. Target cells are grown as a monolayer in a multiwell plate, treated with oligonucleotide followed by cytokine. The adhering cells are then added to the monolayer cells and incubated for 30 to 60 minutes at 37° C. and washed to remove nonadhering cells. Cells adhering to the monolayer may be determined either by directly counting the adhering cells or prelabeling the cells with a radioisotope such as $^{51}Cr$ and quantitating the radioactivity associated with the monolayer as described. Dustin and Springer, *J. Cell Biol.* 1988, 107, 321–331. Antisense oligonucleotides may target either ICAM-1, VCAM-1 or ELAM-1 in the assay.

Figure 7:
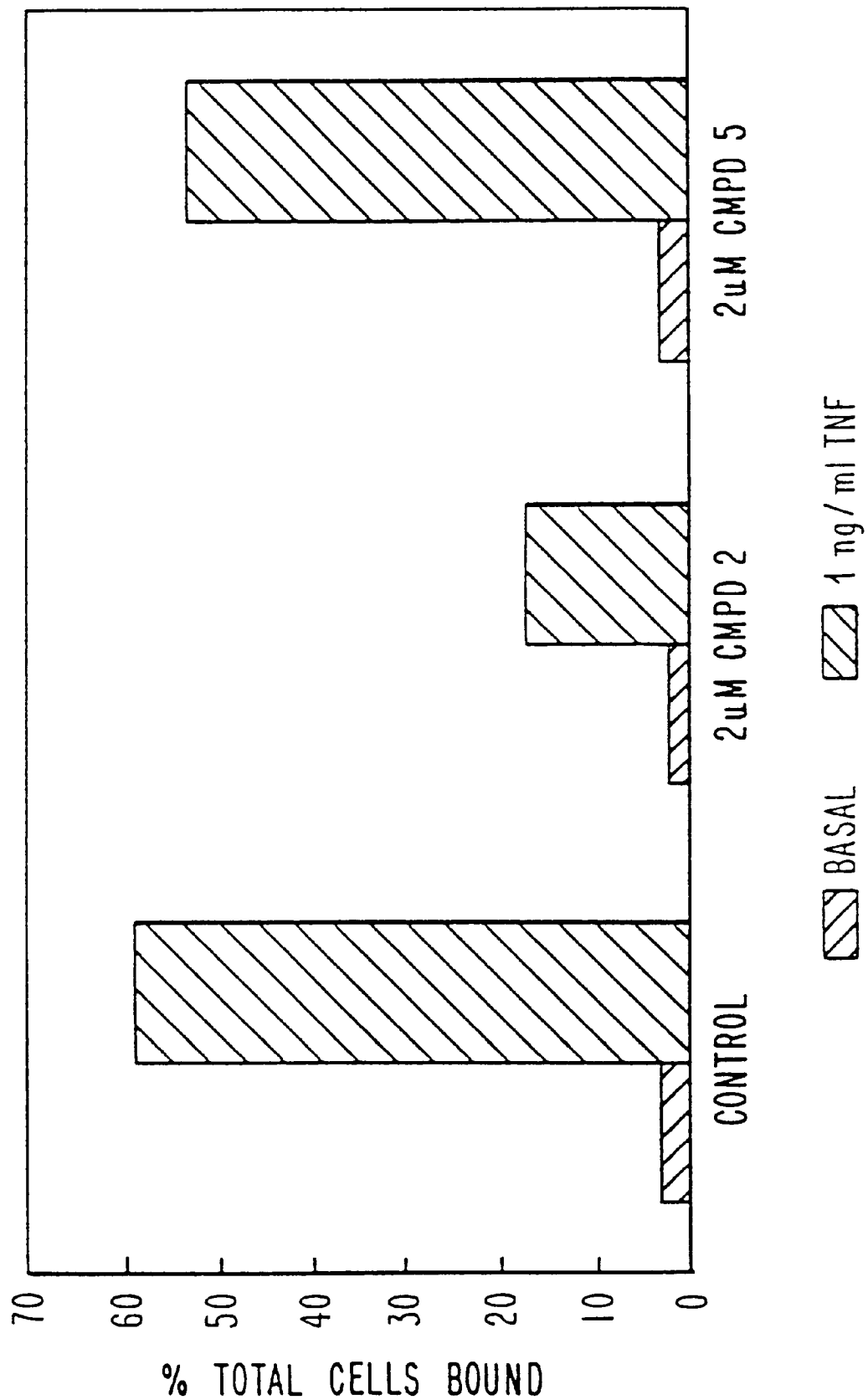
FIG. 7 is a graphical representation of the effect of antisense oligonucleotides on ICAM-1 mediated adhesion of DMSO differentiated HL-60 cells to control and tumor necrosis factor treated human umbilical vein endothelial cells.

An example of the effects of antisense oligonucleotides targeting ICAM-1 mRNA on the adherence of DMSO differentiated HL-60 cells to tumor necrosis factor treated human umbilical vein endothelial cells is shown in FIG. 7. Human umbilical vein endothelial cells were grown to 80% confluence in 12 well plates. The cells were treated with 2 μM oligonucleotide diluted in Opti-MEM containing 8 μM DOTMA for 4 hours at 37° C. The medium was removed and replaced with fresh endothelial cell growth medium (EGM-UV) containing 2 μM of the indicated oligonucleotide and incubated 4 hours at 37° C. Tumor necrosis factor, 1 ng/ml, was added to cells as indicated and cells incubated for an additional 19 hours. The cells were washed once with EGM-UV and $1.6×10^6$ HL-60 cells differentiated for 4 days with 1.3% DMSO added. The cells were allowed to attach for 1 hour at 37° C. and gently washed 4 times with Dulbecco's phosphate-buffered saline (D-PBS) warmed to 37° C. Adherent cells were detached from the monolayer by addition of 0.25 ml of cold (4° C.) phosphate-buffered saline containing 5 mM EDTA and incubated on ice for 5 minutes. The number of cells removed by treatment with EDTA was determined by counting with a hemocytometer. Endothelial cells detached from the monolayer by EDTA treatment could easily be distinguished from HL-60 cells by morphological differences.

In the absence of tumor necrosis factor, 3% of the HL-60 cells bound to the endothelial cells. Treatment of the endothelial cell monolayer with 1 ng/ml tumor necrosis factor increased the number of adhering cells to 59% of total cells added (FIG. 7). Treatment with the antisense oligonucleotide COMPOUND 2 or the control oligonucleotide COMPOUND 5 did not change the number of cells adhering to the monolayer in the absence of tumor necrosis factor treatment (FIG. 7). The antisense oligonucleotide, COMPOUND 2 reduced the number of adhering cells from 59% of total cells added to 17% of the total cells added (FIG. 7). In contrast, the control oligonucleotide COMPOUND 5 did not significantly reduce the number of cells adhering to the tumor necrosis factor treated endothelial monolayer, i.e., 53% of total cells added for COMPOUND 5 treated cells versus 59% for control cells.

These data indicate that antisense oligonucleotides are capable of inhibiting ICAM-1 expression on endothelial cells and that inhibition of ICAM-1 expression correlates with a decrease in the adherence of a neutrophil-like cell to the endothelial monolayer in a sequence specific fashion. Because other molecules also mediate adherence of white blood cells to endothelial cells, such as ELAM-1, and VCAM-1 it is not expected that adherence would be completely blocked.

Example 9

Cell Culture and Treatment with Oligonucleotides

The human lung carcinoma cell line A549 was obtained from the American Type Culture Collection (Bethesda Md.). Cells were grown in Dulbecco's Modified Eagle's Medium (Irvine Scientific, Irvine Calif.) containing 1 gm glucose/liter and 10% fetal calf serum (Irvine Scientific). Human umbilical vein endothelial cells (HUVEC) (Clonetics, San Diego Calif.) were cultured in EGM-UV medium (Clonetics). HUVEC were used between the second and sixth passages. Human epidermal carcinoma A431 cells were obtained from the American Type Culture Collection and cultured in DMEM with 4.5 g/l glucose. Primary human keratinocytes were obtained from Clonetics and grown in KGM (Keratinocyte growth medium, Clonetics).

Cells grown in 96-well plates were washed three times with Opti-MEM (GIBCO, Grand Island, N.Y.) prewarmed to 37° C. 100 µl of Opti-MEM containing either 10 µg/ml N-[1-(2,3-dioleyloxy)propyl]-N,N,N-trimethylammonium chloride (DOTMA, Bethesda Research Labs, Bethesda Md.) in the case of HUVEC cells or 20 µg/ml DOTMA in the case of A549 cells was added to each well. Oligonucleotides were sterilized by centrifugation through 0.2 µm Centrex cellulose acetate filters (Schleicher and Schuell, Keene, N.H.). oligonucleotides were added as 20× stock solution to the wells and incubated for 4 hours at 37° C. Medium was removed and replaced with 150 µl of the appropriate growth medium containing the indicated concentration of oligonucleotide. Cells were incubated for an additional 3 to 4 hours at 37° C. then stimulated with the appropriate cytokine for 14 to 16 hours, as indicated. ICAM-1 expression was determined as described in previous examples. The presence of DOTMA during the first 4 hours incubation with oligonucleotide increased the potency of the oligonucleotides at least 100-fold. This increase in potency correlated with an increase in cell uptake of the oligonucleotide.

Example 10

ELISA screening of additional antisense oligonucleotides for activity against ICAM-1 gene expression in Interleukin-1β-stimulated cells Antisense oligonucleotides were originally designed that would hybridize to five target sites on the human ICAM-1 mRNA. oligonucleotides were synthesized in both phosphodiester (P=O; ISIS 1558, 1559, 1563, 1564 and 1565) and phosphorothioate (P=S; ISIS 1570, 1571, 1572, 1573, and 1574) forms. The oligonucleotides are shown in Table 1. The gene sequence of human ICAM-1 is shown in FIG. 1.

TABLE 1

ANTISENSE OLIGONUCLEOTIDES WHICH TARGET HUMAN ICAM-1

| ISIS NO | SEQ ID NO | TARGET REGION | MODIFICATION |
|---|---|---|---|
| 1558 | 1 | AUG Codon (64–81) | P=O |
| 1559 | 2 | 5'-Untranslated (32–49) | P=O |
| 1563 | 3 | 3'-Untranslated (2190–3010) | P=O |
| 1564 | 4 | 3'-Untranslated (2849–2866) | P=O |
| 1565 | 5 | Coding Region (1378–1395) | P=O |
| 1570 | 1 | AUG Codon (64–81) | P=S |
| 1571 | 2 | 5'-Untranslated (32–49) | P=S |
| 1572 | 3 | 3'-Untranslated (2190–3010) | P=s |
| 1573 | 4 | 3'-Untranslated (2849–2866) | P=S |
| 1574 | 5 | Coding Region (1378–1395) | P=S |
| 1930 | 6 | 5'-Untranslated (1–20) | P=S |
| 1931 | 7 | AUG Codon (55–74) | P=S |
| 1932 | 8 | AUG Codon (72–91) | P=S |
| 1933 | 9 | Coding Region (111–130) | P=S |
| 1934 | 10 | Coding Region (351–370) | P=S |
| 1935 | 11 | Coding Region (889–908) | P=S |
| 1936 | 12 | Coding Region (1459–1468) | P=S |
| 1937 | 13 | Termination Codon (1651–1687) | P=S |
| 1938 | 14 | Termination Codon (1668–1687) | P=S |
| 1939 | 15 | 3'-Untranslated (1952–1971) | P=S |
| 1940 | 16 | 3'-Untranslated (2975–2994) | P=S |
| 2149 | 17 | AUG Codon (64–77) | P=S |
| 2163 | 18 | AUG Codon (64–75) | P=S |
| 2164 | 19 | AUG Codon (64–73) | P=S |
| 2165 | 20 | AUG Codon (66–80) | P=S |
| 2173 | 21 | AUG Codon (64–79) | P=s |
| 2302 | 22 | 3'-Untranslated (2114–2133) | P=S |
| 2303 | 23 | 3'-Untranslated (2039–2058) | P=S |
| 2304 | 24 | 3'-Untranslated (1895–1914) | P=S |
| 2305 | 25 | 3'-Untranslated (1935–1954) | P=S |
| 2307 | 26 | 3'-Untranslated (1976–1995) | P=S |
| 2634 | 1 | AUG-Codon (64–81) | 2'-fluoro A, C & U; P=S |
| 2637 | 15 | 3'-Untranslated (1952–1971) | 2'-fluoro A, C & U; |
| 2691 | 1 | AUG Codon (64–81) | P=O; except last 3 bases, P=S |
| 2710 | 15 | 3'-Untranslated (1952–1971) | 2'-O-methyl; P=O |
| 2711 | 1 | AUG Codon (64–81) | 2'-O-methyl; P=O |
| 2973 | 15 | 3'-Untranslated (1952–1971) | 2'-O-methyl; P=S |
| 2974 | 1 | AUG Codon (64–81) | 2'-O-methyl; P=S |
| 3064 | 27 | 5'-CAP (32–51) | P=S; G & C added as spacer to 3' |
| 3067 | 84 | 5'-CAP (32–51) | P=S |

TABLE 1-continued

ANTISENSE OLIGONUCLEOTIDES WHICH TARGET HUMAN ICAM-1

| ISIS NO | SEQ ID NO | TARGET REGION | MODIFICATION |
|---|---|---|---|
| 3222 | 84 | 5'-CAP (32–51) | 2'-O-methyl; P=O |
| 3224 | 84 | 5'-CAP (32–51) | 2'-O-methyl; P=S |
| 3581 | 85 | 3'-Untranslated (1959–1978) | P=S |

Inhibition of ICAM-1 expression on the surface of interleukin-1β-stimulated cells by the oligonucleotides was determined by ELISA assay as described in previous examples. The oligonucleotides were tested in two different cell lines. None of the phosphodiester oligonucleotides inhibited ICAM-1 expression. This is probably due to the rapid degradation of phosphodiester oligonucleotides in cells. Of the five phosphorothioate oligonucleotides, the most active was ISIS 1570, which hybridizes to the AUG translation initiation codon. A 2'-o-methyl phosphorothioate oligonucleotide, ISIS 2974, was approximately threefold less effective than ISIS 1570 in inhibiting ICAM-1 expression in HUVEC and A549 cells. A 2'-fluoro oligonucleotide, ISIS 2634, was also less effective.

Figure 8:
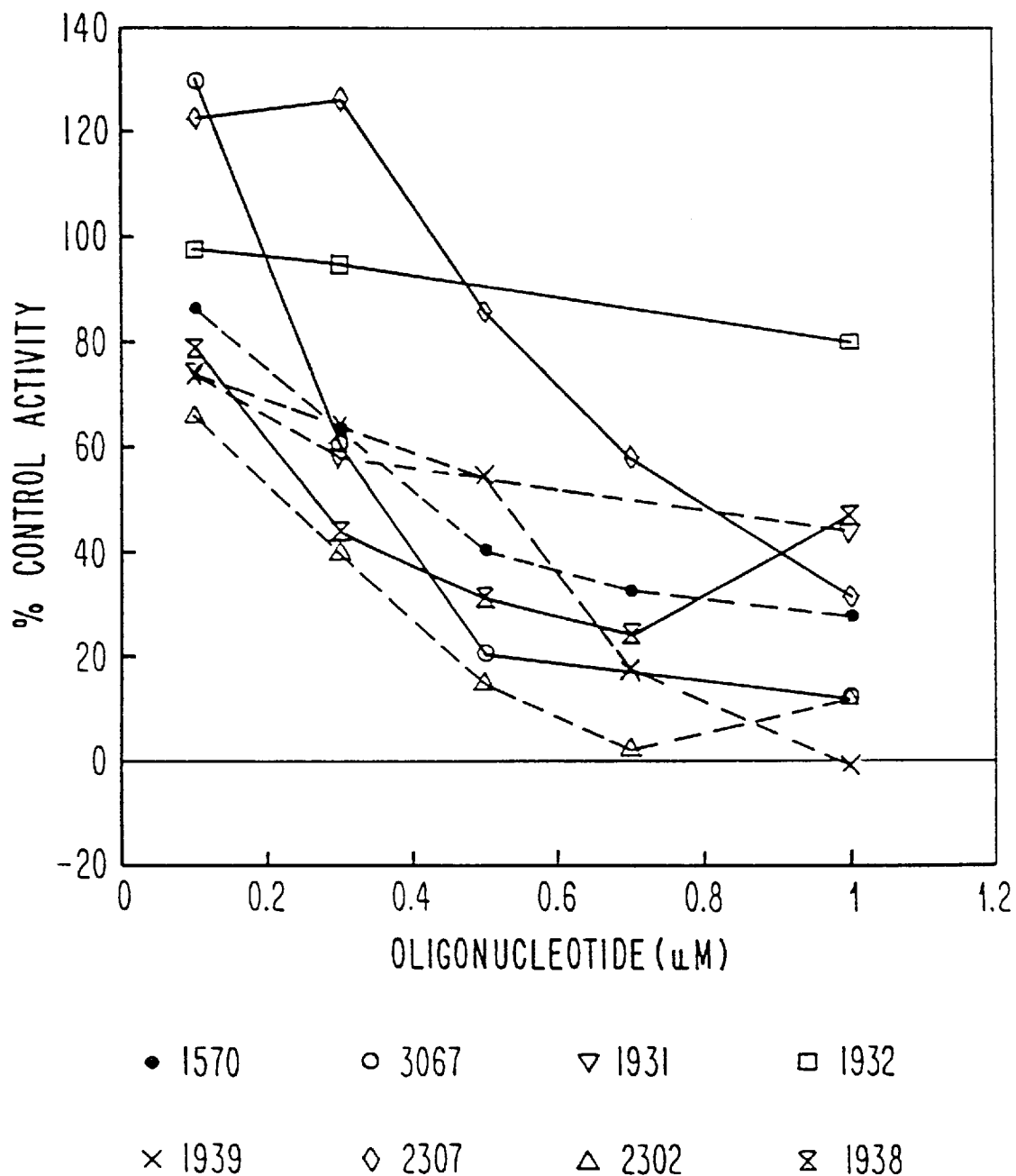
FIG. 8 is a graphical representation of the effects of selected antisense oligonucleotides on ICAM-1 expression in A549 human lung carcinoma cells.

Based on the initial data obtained with the five original targets, additional oligonucleotides were designed which would hybridize with the ICAM-1 mRNA. The antisense oligonucleotide (ISIS 3067, SEQ ID NO: 84) which hybridizes to the predicted transcription initiation site (5' cap site) was approximately as active in IL-1β-stimulated cells as the oligonucleotide that hybridizes to the AUG codon (ISIS 1570), as shown in FIG. 8. ISIS 1931 and 1932 hybridize 5' and 3', respectively, to the AUG translation initiation codon. All three oligonucleotides that hybridize to the AUG region inhibit ICAM-1 expression, though ISIS 1932 was slightly less active than ISIS 1570 and ISIS 1931. Oligonucleotides which hybridize to the coding region of ICAM-1 mRNA (ISIS 1933, 1934, 1935, 1574 and 1936) exhibited weak activity. Oligonucleotides that hybridize to the translation termination codon (ISIS 1937 and 1938) exhibited moderate activity.

Surprisingly, the most active antisense oligonucleotide was ISIS 1939, a phosphorothioate oligonucleotide targeted to a sequence in the 3'-untranslated region of ICAM-1 mRNA (see Table 1). Other oligonucleotides having the same sequence were tested, 2'-O-methyl (ISIS 2973) and 2'-fluoro (ISIS 2637); however, they did not exhibit this level of activity. Oligonucleotides targeted to other 3' untranslated sequences (ISIS 1572, 1573 and 1940) were also not as active as ISIS-1939. In fact, ISIS 1940, targeted to the polyadenylation signal, did not inhibit ICAM-1 expression.

Because ISIS 1939 proved unexpectedly to exhibit the greatest antisense activity of the original 16 oligonucleotides tested, other oligonucleotides were designed to hybridize to sequences in the 3'-untranslated region of ICAM-1 mRNA (ISIS 2302, 2303, 2304, 2305, and 2307, as shown in Table 1). ISIS 2307, which hybridizes to a site only five bases 3' to the ISIS 1939 target, was the least active of the series (FIG. 8). ISIS 2302, which hybridizes to the ICAM-1 mRNA at a position 143 bases 3' to the ISIS 1939 target, was the most active of the series, with activity comparable to that of ISIS 1939. Examination of the predicted RNA secondary structure of the human ICAM-1 mRNA 3'-untranslated region (according to M. Zuker, Science 1989, 244, 48–52) revealed that both ISIS 1939 and ISIS 2302 hybridize to sequences predicted to be in a stable stem-loop structure. Current dogma suggests that regions of RNA secondary structure should be avoided when designing antisense oligonucleotides. Thus, ISIS 1939 and ISIS 2302 would not have been predicted to inhibit ICAM-1 expression.

The control oligonucleotide ISIS 1821 did inhibit ICAM-1 expression in HUVEC cells with activity comparable to that of ISIS 1934; however, in A549 cells ISIS 1821 was less effective than ISIS 1934. The negative control, ISIS 1821, was found to have a small amount of activity against ICAM expression, probably due in part to its ability to hybridize (12 of 13 base match) to the ICAM-1 mRNA at a position 15 bases 3' to the AUG translation initiation codon.

These studies indicate that the AUG translation initiation codon and specific 3'-untranslated sequences in the ICAM-1 mRNA were the most susceptible to antisense oligonucleotide inhibition of ICAM-1 expression.

Figure 9:
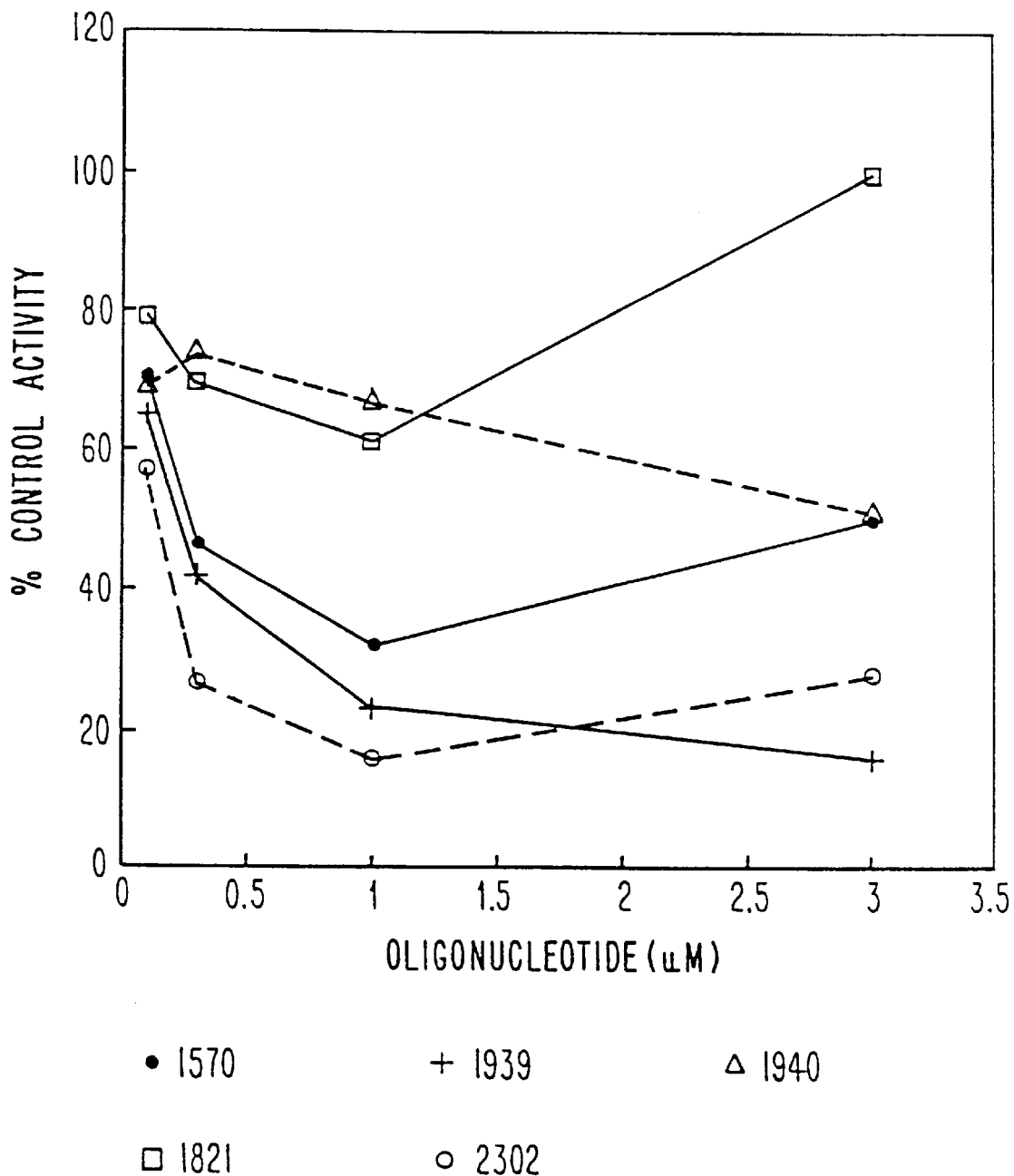
FIG. 9 is a graphical representation of the effects of selected antisense oligonucleotides on ICAM-1 expression in primary human keratinocytes.

In addition to inhibiting ICAM-1 expression in human umbilical vein cells and the human lung carcinoma cells (A549), ISIS 1570, ISIS 1939 and ISIS 2302 were shown to inhibit ICAM-1 expression in the human epidermal carcinoma A431 cells and in primary human keratinocytes (shown in FIG. 9). These data demonstrate that antisense oligonucleotides are capable of inhibiting ICAM-1 expression in several human cell lines. Furthermore, the rank order potency of the oligonucleotides is the same in the four cell lines examined. The fact that ICAM-1 expression could be inhibited in primary human keratinocytes is important because epidermal keratinocytes are an intended target of the antisense nucleotides.

Example 11

Antisense Oligonucleotide Inhibition of ICAM-1 Expression in Cells Stimulated with Other Cytokines Two oligonucleotides, ISIS 1570 and ISIS 1939, were tested for their ability to inhibit TNF-α and IFN-γ-induced ICAM-1 expression. Treatment of A549 cells with 1 μM antisense oligonucleotide inhibited IL-1β, TNF-α and IFN-γ-induced ICAM-1 expression in a sequence-specific manner. The antisense oligonucleotides inhibited IL-1β and TNF-α-induced ICAM-1 expression to a similar extent, while IFN-γ-induced ICAM-1 expression was more sensitive to antisense inhibition. The control oligonucleotide, ISIS 1821, did not significantly inhibit IL-1β- or TNF-α-induced ICAM-1 expression and inhibited IFN-γ-induced ICAM-1 expression slightly, as follows:

| Cytokine | Antisense Oligonucleotide (% Control Expression) | | |
|---|---|---|---|
| | ISIS 1570 | ISIS 1939 | ISIS 1821 |
| 3 U/ml IL-1β | 56.6 ± 2.9 | 38.1 ± 3.2 | 95 ± 6.6 |
| 1 ng/ml TNF-α | 58.1 ± 0.9 | 37.6 ± 4.1 | 103.5 ± 8.2 |
| 100 U/ml gamma-IFN | 38.9 ± 3.0 | 18.3 ± 7.0 | 83.0 ± 3.5 |

Example 12

Antisense Effects are Abolished by Sense Strand Controls

The antisense oligonucleotide inhibition of ICAM-1 expression by the oligonucleotides ISIS 1570 and ISIS 1939 could be reversed by hybridization of the oligonucleotides with their respective sense strands. The phosphorothioate sense strand for ISIS 1570 (ISIS 1575), when applied alone, slightly enhanced IL-1β-induced ICAM-1 expression. Premixing ISIS 1570 with ISIS 1575 at equal molar concentrations, prior to addition to the cells, blocked the effects of ISIS 1570. The complement to ISIS 1939 (ISIS 2115) enhanced ICAM-1 expression by 46% when added to the cells alone. Prehybridization of ISIS 2115 to ISIS 1939 completely blocked the inhibition of ICAM-1 expression by ISIS 1939.

Example 13

Specificity of Antisense Inhibition of ICAM-1

The specificity of the antisense oligonucleotides ISIS 1570 and ISIS 1939 for ICAM-1 was evaluated by immunoprecipitation of $^{35}$S-labelled proteins. A549 cells were grown to confluence in 25 cm$^2$ tissue culture flasks and treated with antisense oligonucleotides as described in previous examples. The cells were stimulated with interleukin-1β for 14 hours, washed with methionine-free DMEM plus 10% dialyzed fetal calf serum, and incubated for 1 hour in methionine-free medium containing 10% dialyzed fetal calf serum, 1 μM oligonucleotide and interleukin-1, as indicated. $^{35}$S-Methionine/cysteine mixture (Tran$^{35}$S-label, purchased from ICN, Costa Mesa, Calif.) was added to the cells to an activity of 100 μCi/ml and the cells were incubated an additional 2 hours. Cellular proteins were extracted by incubation with 50 mM Tris-HCl pH 8.0, 150 mM NaCl, 1.0% NP-40, 0.5% deoxycholate and 2 mM EDTA (0.5 ml per well) at 4° C. for 30 minutes. The extracts were clarified by centrifugation at 18,000×g for 20 minutes. The supernatants were preadsorbed with 200 μl protein G-Sepharose beads (Bethesda Research Labs, Bethesda Md.) for 2 hours at 4° C., divided equally and incubated with either 5 μg ICAM-1 monoclonal antibody (purchased from AMAC Inc., Westbrook Me.) or HLA-A,B antibody (W6/32, produced by murine hybridoma cells obtained from the American Type Culture Collection, Bethesda, Md.) for 15 hours at 4° C. Immune complexes were trapped by incubation with 200 μl of a 50% suspension of protein G-Sepharose (v/v) for 2 hours at 4° C., washed 5 times with lysis buffer and resolved on an SDS-polyacrylamide gel. Proteins were detected by autoradiography.

Treatment of A549 cells with 5 units/ml of interleukin-1β was shown to result in the synthesis of a 95–100 kDa protein migrating as a doublet which was immunoprecipitated with the monoclonal antibody to ICAM-1. The appearance as a doublet is believed to be due to differently glycosylated forms of ICAM-1. Pretreatment of the cells with the antisense oligonucleotide ISIS 1570 at a concentration of 1 μM decreased the synthesis of ICAM-1 by approximately 50%, while 1 μM ISIS 1939 decreased ICAM-1 synthesis to near background. Antisense oligonucleotide ISIS 1940, inactive in the ICAMI-1 ELISA assay did not significantly reduce ICAM-1 synthesis. None of the antisense oligonucleotides hybridizable with ICAM-1 targets had a demonstrable effect on HLA-A, B synthesis, demonstrating the specificity of the oligonucleotides for ICAM -1. Furthermore, the proteins which nonspecifically precipitated with the ICAM-1 antibody and protein G-Sepharose were not significantly affected by treatment with the antisense oligonucleotides.

Example 14

Figure 10:
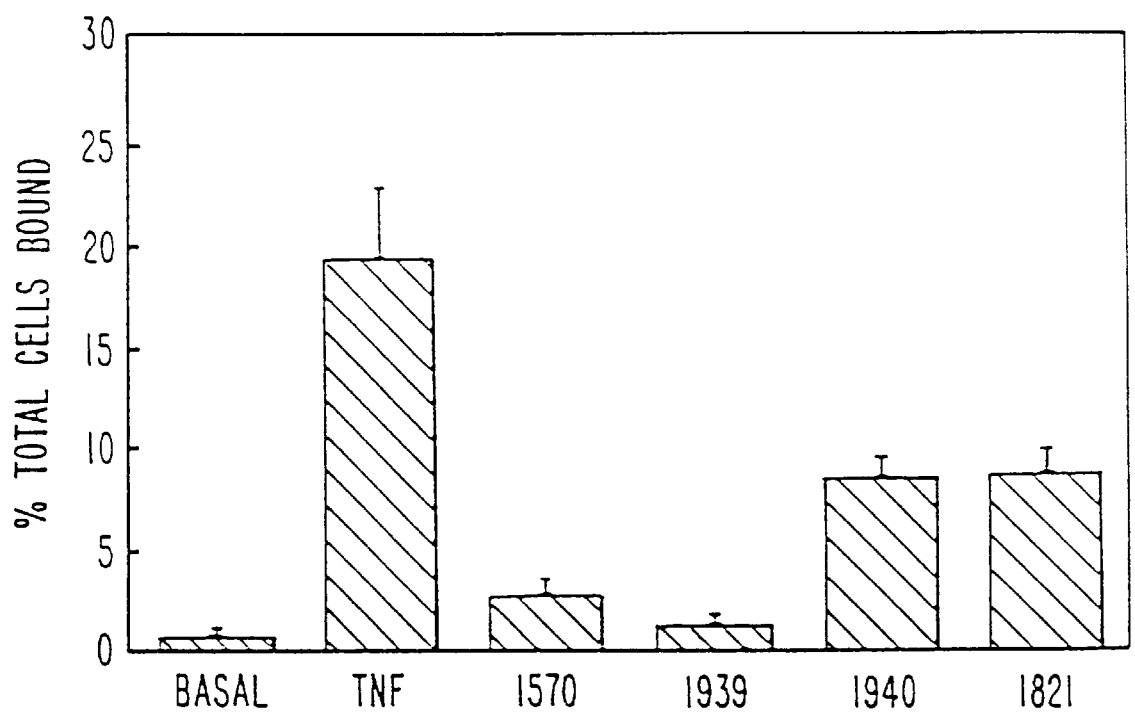
FIG. 10 is a graphical representation of the effect of selected antisense oligonucleotides on ICAM-1 mediated adhesion of DMSO differentiated HL-60 cells to control and tumor necrosis factor treated human umbilical vein endothelial cells.

Screening of Additional Antisense Oligonucleotides for Activity against ICAM-1 by Cell Adhesion Assay Human umbilical vein endothelial (HUVEC) cells were grown and treated with oligonucleotides as in above examples. Cells were treated with either ISIS 1939, ISIS 1940, or the control oligonucleotide ISIS 1821 for 4 hours, then stimulated with TNF-α for 20 hours. Basal HUVEC minimally bound HL-60 cells, while TNF-stimulated HUVEC bound 19% of the total cells added. Pretreatment of the HUVEC monolayer with 0.3 μM ISIS 1939 reduced the adherence of HL-60 cells to basal levels, as shown in FIG. 10. The control oligonucleotide, ISIS 1821, and ISIS 1940 reduced the percentage of cells adhering from 19% to 9%. These data indicate that antisense oligonucleotides targeting ICAM-1 may specifically decrease adherence of a leukocyte-like cell line (HL-60) to TNF-α-treated HUVEC.

Example 15

ELISA Screening of Antisense Oligonucleotides for Activity Against ELAM-1 Gene Expression Primary human umbilical vein endothelial (HUVEC) cells, passage 2 to 5, were plated in 96-well plates and allowed to reach confluence. Cells were washed three times with Opti-MEM (GIBCO, Grand Island N.Y.). Cells were treated with increasing concentrations of oligonucleotide diluted in Opti-MEM containing 10 μg/ml DOTMA solution (Bethesda Research Labs, Bethesda Md.) for 4 hours at 37° C. The medium was removed and replaced with EGM-UV (Clonetics, San Diego Calif.) plus oligonucleotide. Tumor necrosis factor a was added to the medium (2.5 ng/ml) and the cells were incubated an additional 4 hours at 37° C.

ELAM-1 expression was determined by ELISA. Cells were gently washed three times with Dulbecco's phosphate-buffered saline (D-PBS) prewarmed to 37° C. Cells were fixed with 95% ethanol at 4° C. for 20 minutes, washed three times with D-PBS and blocked with 2% BSA in D-PBS. Cells were incubated with ELAM-1 monoclonal antibody BBA-1 (R&D Systems, Minneapolis Minn.) diluted to 0.5 μg/ml in D-PBS containing 2% BSA for 1 hour at 37° C. Cells were washed three times with D-PBS and the bound ELAM-1 antibody detected with biotinylated goat anti-mouse secondary antibody followed by β-galactosidase-conjugated streptavidin as described in previous examples.

The activity of antisense phosphorothioate oligonucleotides which target 11 different regions on the ELAM-1 cDNA (the ELAM-1 target sequence is shown in FIG. 2) and two oligonucleotides which target ICAM-1 (as controls) was determined using the ELAM-1 ELISA. The oligonucleotide and targets are shown in Table 2.

TABLE 2

ANTISENSE OLIGONUCLEOTIDES WHICH TARGET HUMAN ELAM-1

| ISIS NO | SEQ ID NO | TARGET REGION | MODIFICATION |
|---|---|---|---|
| 1926 | 28 | AUG Codon (143–164) | P=S |
| 2670 | 29 | 3'-Untranslated (3718–3737) | P=S |
| 2673 | 30 | 3'-Untranslated (2657–2677) | P=S |
| 2674 | 31 | 3'-Untranslated (2617–2637) | P=S |
| 2678 | 32 | 3'-Untranslated (3558–3577) | P=S |
| 2679 | 33 | 5'-Untranslated (41–60) | P=S |
| 2680 | 34 | 3'-Untranslated (3715–3729) | P=S |
| 2683 | 35 | AUG Codon (143–163) | P=S |
| 2686 | 36 | AUG Codon (149–169) | P=S |
| 2687 | 37 | 5'-Untranslated (18–37) | P=S |
| 2693 | 38 | 3'-Untranslated (2760–2788) | P=S |
| 2694 | 39 | 3'-Untranslated (2934–2954) | P=S |

Figure 11:
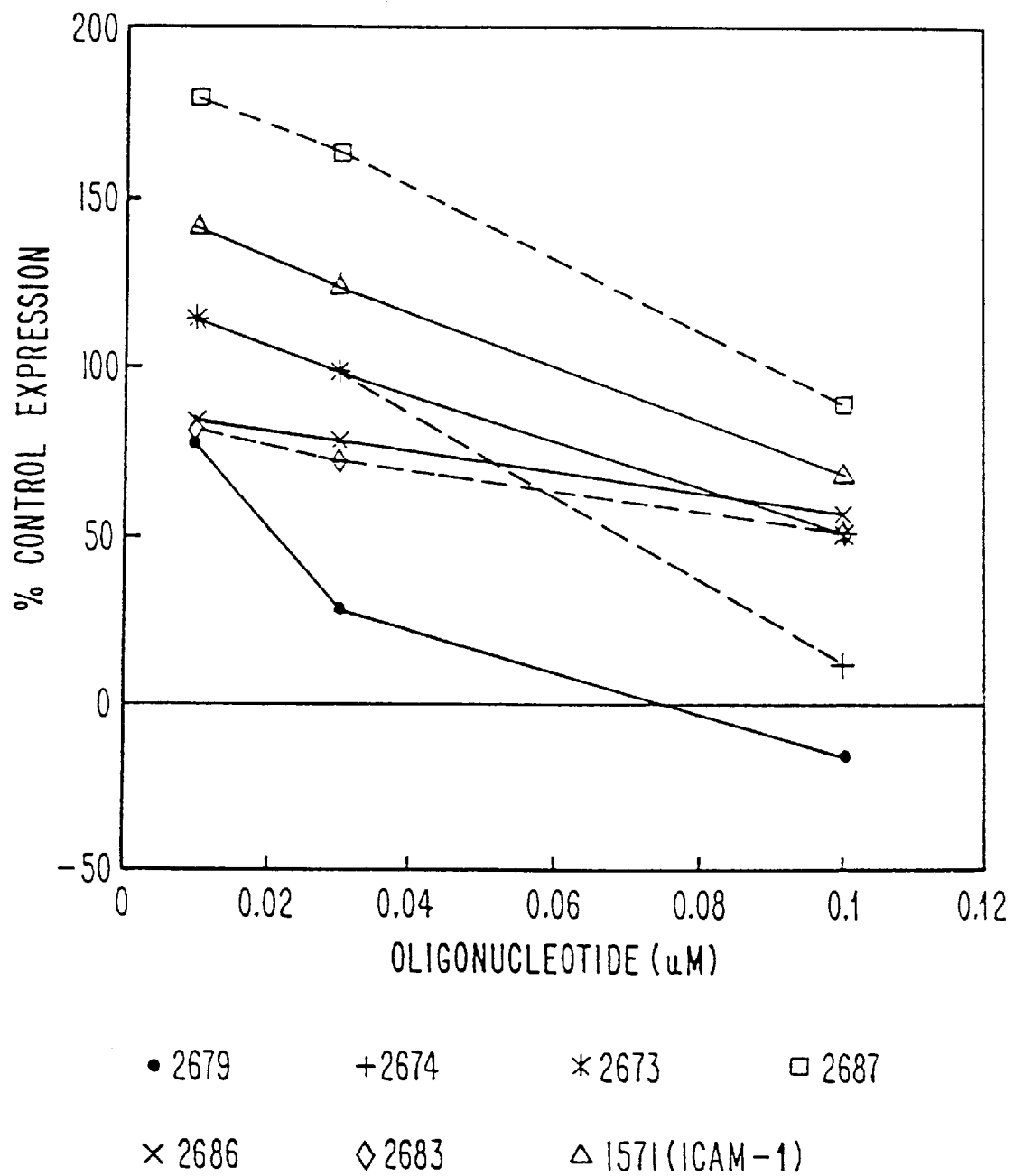
FIG. 11 is a graphical representation of the effects of selected antisense oligonucleotides on ELAM-1 expression on tumor necrosis factor-treated human umbilical vein endothelial cells.

In contrast to what was observed with antisense oligonucleotides targeted to ICAM-1, the most potent oligonucleotide modulator of ELAM-1 activity (ISIS 2679) was hybridizable with specific sequences in the 5'-untranslated region of ELAM-1. ISIS 2687, an oligonucleotide which hybridized to sequences ending three bases upstream of the ISIS 2679 target, did not show significant activity (FIG. 11). Therefore, ISIS 2679 hybridizes to a unique site on the ELAM-1 mRNA, which is uniquely sensitive to inhibition with antisense oligonucleotides. The sensitivity of this site to inhibition with antisense oligonucleotides was not predictable based upon RNA secondary structure predictions or information in the literature.

Example 16

Figure 12:
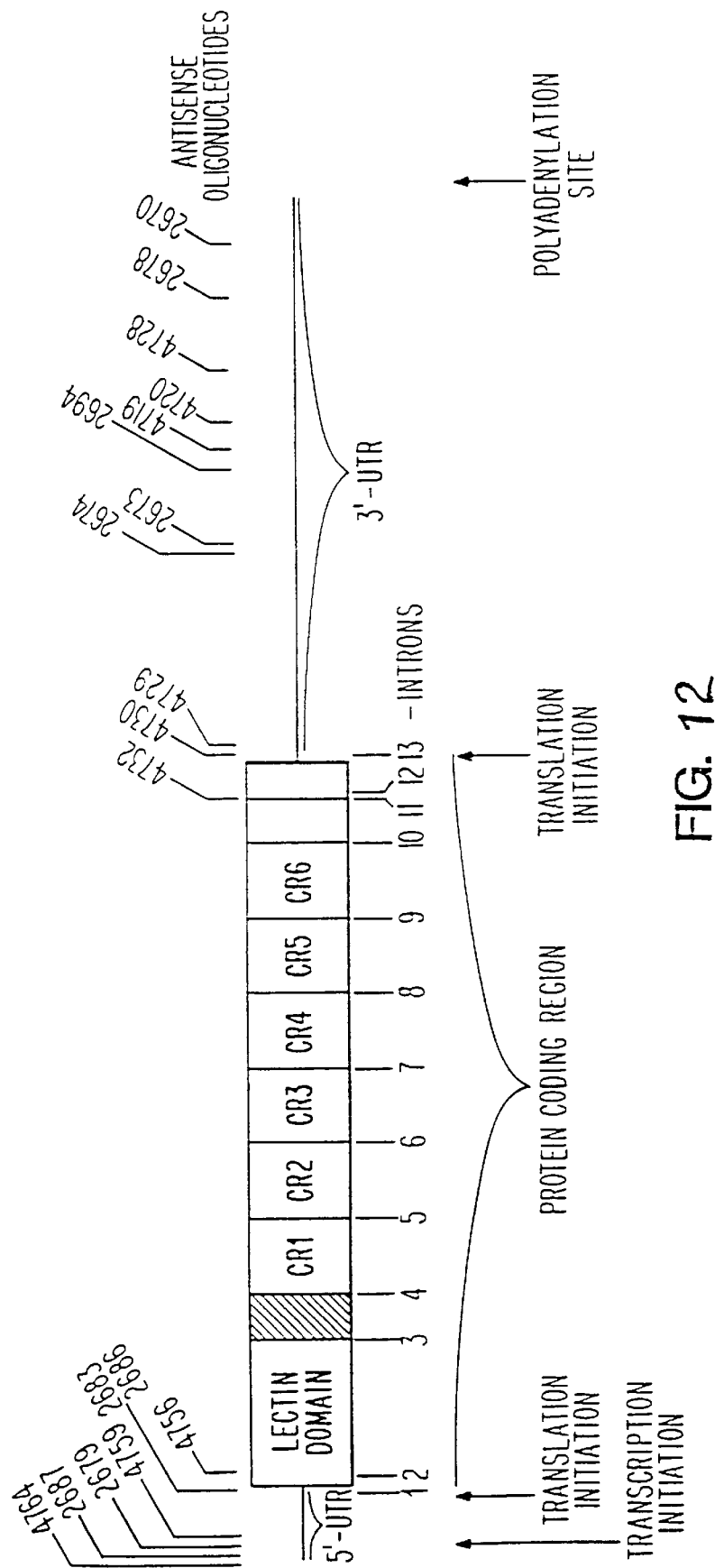
FIG. 12 is a graphical representation of the human ELAM-1 mRNA showing target sites of antisense oligonucleotides.

ELISA Screening of Additional Antisense Oligonucleotides for Activity against ELAM-1 Gene Expression Inhibition of ELAM-1 expression by eighteen antisense phosphorothioate oligonucleotides was determined using the ELISA assay as described in the previous examples. The target sites of these oligonucleotides on the ELAM-1 mRNA are shown in FIG. 12. The sequence and activity of each oligonucleotide against ELAM-1 are shown in Table 3. The oligonucleotides indicated by an asterisk (*) have IC50's of approximately 50 nM or below and are preferred. IC50 indicates the dosage of oligonucleotide which results in 50% inhibition of ELAM-1 expression. ELAM-1 expression is given as % of control.

Example 17

Figure 13:
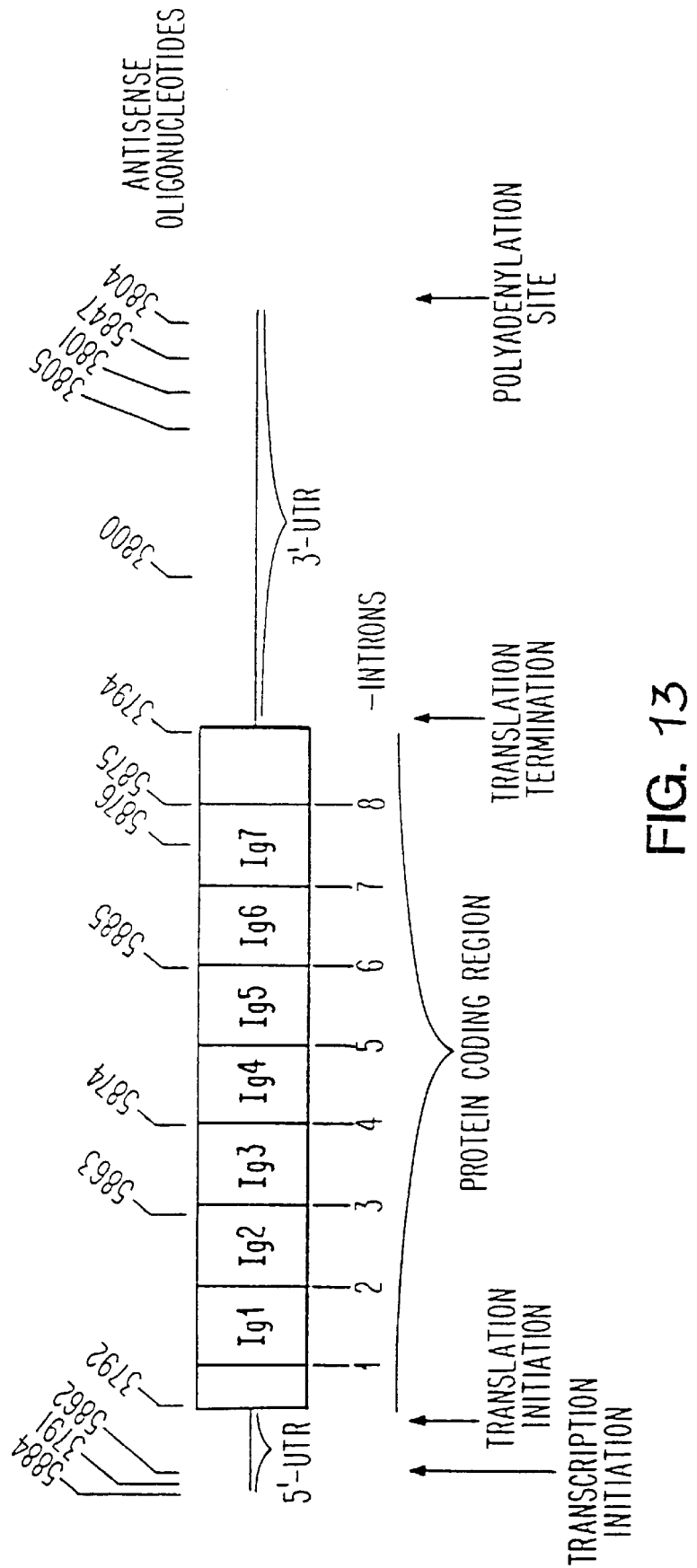
FIG. 13 is a graphical representation of the human VCAM-1 mRNA showing target sites of antisense oligonucleotides.

ELISA Screening of Antisense Oligonucleotides for Activity against VCAM-1 Gene Expression Inhibition of VCAM-1 expression by fifteen antisense phosphorothioate oligonucleotides was determined using the ELISA assay approximately as described in previous examples, except that cells were stimulated with TNF-β for 16 hours and VCAM-1 expression was detected by a VCAM-1 specific monoclonal antibody (R & D Systems, Minneapolis, Minn.) used at 0.5 μg/ml. The target sites of these oligonucleotides on the VCAM-1 mRNA are shown in FIG. 13. The VCAM-1 sequence is provided as FIG. 3. The sequence and activity of each oligonucleotide against VCAM-1 are shown in Table 4. The oligonucleotides indicated by an asterisk (*) have IC50's of approximately 50 nM or below and are preferred. IC50 indicates the dosage of oligonucleotide which results in 50% inhibition of VCAM-1 expression.

TABLE 3

Inhibition of human ELAN-1 expression by antisense oligonucleotides

| ISIS# | SEQ ID NO: | POSITION | SEQUENCE | VCAM-1 EXPRESSION | |
|---|---|---|---|---|---|
| | | | | 30 nM oligo | 50 nM oligo |
| *4764 | 52 | 5'-UTR1-19 | GAAGTCAGCCAAGAACAGCT | 70.2 | 50.2 |
| 2687 | 37 | 5'-UTR17-36 | TATAGGAGTTTTGATGTGAA | 91.1 | 73.8 |
| *2679 | 33 | 5'-UTR 40-59 | CTGCTGCCTCTGTCTCAGGT | 6.4 | 6.0 |
| *4759 | 53 | 5'-UTR 64-83 | ACAGGATCTCTCAGGTGGGT | 30.0 | 20.2 |
| *2683 | 35 | AUG 143-163 | AATCATGACTTCAAGAGTTCT | 47.9 | 48.5 |
| *2686 | 36 | AUG 148-168 | TGAAGCAATCATGACTTCAAG | 51.1 | 46.9 |
| *4756 | 54 | I/E 177-196 | CCAAAGTGAGAGCTGAGAGA | 53.9 | 35.7 |
| 4732 | 55 | Coding 1936-1955 | CTGATTCAAGGCTTTGGCAG | 68.5 | 55.3 |
| *4730 | 56 | I/E 3'UTR 2006-2025 | TTCCCCAGATGCACCTGTTT | 14.1 | 2.3 |
| *4729 | 57 | 3'-UTR 2063-2082 | GGGCCAGAGACCCGAGGAGA | 49.4 | 46.3 |
| *2674 | 31 | 3'-UTR 2617-2637 | CACAATCCTTAAGAACTCTTT | 33.5 | 28.1 |
| 2673 | 30 | 3'-UTR 2656-2676 | GTATGGAAGATTATAATATAT | 58.9 | 53.8 |
| 2694 | 39 | 3'-UTR 2933-2953 | GACAATATACAAACCTTCCAT | 72.0 | 64.6 |
| *4719 | 58 | 3'-UTR 2993-3012 | ACGTTTGGCCTCATGGAAGT | 36.8 | 34.7 |
| 4720 | 59 | 3'-UTR 3093-3112 | GGAATGCAAAGCACATCCAT | 63.5 | 70.6 |
| *2678 | 32 | 3'-UTR 3557-3576 | ACCTCTGCTGTTCTGATCCT | 24.9 | 15.3 |
| 2670 | 29 | 3'-UTR 3717-3736 | ACCACACTGGTATTTCACAC | 72.2 | 67.2 |

I/E indicates Intron/Exon junction
Oligonucleotides with IC50's of approximately 50 nM or below are indicated by an asterisk (*).

An additional oligonucleotide targeted to the 3'-untranslated region (ISIS 4728) did not inhibit ELAM expression.

TABLE 4

Inhibition of human VCAM-1 expression by antisense oligonucleotides
VCAM-1 expression is given as % of control

| ISIS# | SEQ ID NO: | POSITION | SEQUENCE | VCAM-1 EXPRESSION | |
|---|---|---|---|---|---|
| | | | | 30 nM oligo | 50 nM oligo |
| *5884 | 60 | 5'-UTR 1-19 | CGATGCAGATACCGCGGAGT | 79.2 | 37.2 |
| 3791 | 61 | 5'-UTR 38-58 | GCCTGGGAGGGTATTCAGCT | 92.6 | 58.0 |

TABLE 4-continued

Inhibition of human VCAM-1 expression by antisense oligonucleotides
VCAM-1 expression is given as % of control

| ISIS# | SEQ ID NO: | POSITION | SEQUENCE | VCAM-1 EXPRESSION 30 nM oligo | 50 nM oligo |
|---|---|---|---|---|---|
| 5862 | 62 | 5'-UTR 48-68 | CCTGTGTGTGCCTGGGAGGG | 115.0 | 83.5 |
| *3792 | 63 | AUG 110-129 | GGCATTTTAAGTTGCTGTCG | 68.7 | 33.7 |
| 5863 | 64 | CODING 745-764 | CAGCCTGCCTTACTGTGGGC | 95.8 | 66.7 |
| *5874 | 65 | CODING 1032-1052 | CTTGAACAATTAATTCCACCT | 66.5 | 35.3 |
| 5885 | 66 | E/I 1633-1649 + intron | TTACCATTGACATAAAGTGTT | 84.4 | 52.4 |
| *5876 | 67 | CODING 2038-2057 | CTGTGTCTCCTGTCTCCGCT | 43.5 | 26.6 |
| *5875 | 68 | CODING 2183-2203 | GTCTTTGTTGTTTTCTCTTCC | 59.2 | 34.8 |
| 3794 | 69 | TERMIN. 2344-2362 | TGAACATATCAAGCATTAGC | 75.3 | 52.6 |
| *3800 | 70 | 3'-UTR 2620-2639 | GCAATCTTGCTATGGCATAA | 64.4 | 47.7 |
| *3805 | 71 | 3'-UTR 2826-2845 | CCCGGCATCTTTACAAAACC | 67.7 | 44.9 |
| *3801 | 50 | 3'-UTR 2872-2892 | AACCCAGTGCTCCCTTTGCT | 36.5 | 21.3 |
| *5847 | 72 | 3'-UTR 2957-2976 | AACATCTCCGTACCATGCCA | 51.8 | 24.6 |
| *3804 | 51 | 3'-UTR 3005-3024 | GGCCACATTGGGAAAGTTGC | 55.1 | 29.3 |

E/I indicates exon/intron junction
Oligonucleotides with IC50's cf approximately 50 nM or below are indicated by an asterisk (*).

Example 18

ICAM-1 Expression in C8161 Human Melanoma Cells

Human melanoma cell line C8161 (a gift of Dr. Dan Welch, Hershey Medical Center) was derived from an abdominal wall metastasis from a patient with recurrent malignant melanoma. These cells form multiple metastases in lung, subcutis, spleen, liver and regional lymph nodes after subcutaneous, intradermal and intravenous injection into athymic nude mice. Cells were grown in DMA-F12 medium containing 10% fetal calf serum and were passaged using 2 mM EDTA.

Exposure of C8161 cells to TNF-α resulted in a six-fold increase in cell surface expression of ICAM-1 and an increase in ICAM-1 mRNA levels in these cells. ICAM-1 expression on the cell surface was measured by ELISA. Cells were treated with increasing concentrations of antisense oligonucleotides in the presence of 15 μg/ml Lipofectin for 4 hours at 37° C. ICAM-1 expression was induced by incubation with 5 ng/ml TNF-α for 16 hours. Cells were washed 3× in DPBS and fixed for 20 minutes in 2% formaldehyde. Cells were washed in DPBS, blocked with 2% BSA for 1 hour at 37° C. and incubated with ICAM-1 monoclonal antibody 84H10 (AMAC, Inc., Westbrooke, Me.). Detection of bound antibody was determined by incubation with a biotinylated goat anti-mouse IgG followed by incubation with β-galactosidase-conjugated streptavidin and developed with chlorophenol red-β-D-galactopyranoside and quantified by absorbance at 575 nm. ICAM-1 mRNA levels were measured by Northern blot analysis.

Example 19

Oligonucleotide Inhibition of ICAM-1 Expression in C8161 Human Melanoma Cells

Figure 14:
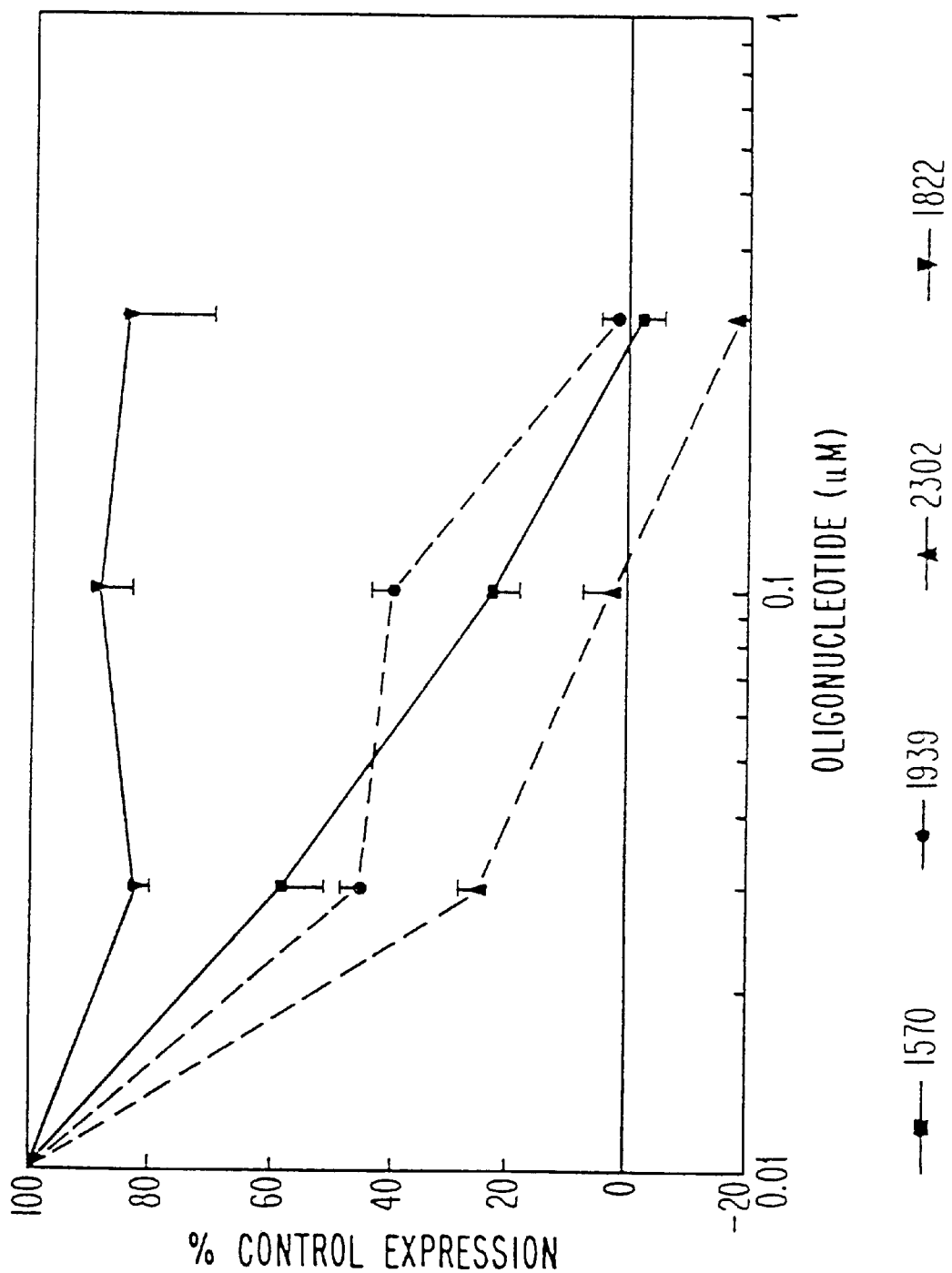
FIG. 14 is a line graph showing inhibition of ICAM-1 expression in C8161 human melanoma cells following treatment with antisense oligonucleotides complementary to ICAM-1.

As shown in FIG. 14, antisense oligonucleotides ICAM 1570 (SEQ ID NO: 1), ISIS 1939 (SEQ ID NO: 15) and ISIS 2302 (SEQ ID NO: 22) targeted to ICAM-1 decreased cell surface expression of ICAM-1 (detected by ELISA). ISIS 1822, a negative control oligonucleotide complementary to 5-lipoxygenase, did not affect ICAM-1 expression. The data were expressed as percentage of control activity, calculated as follows: (ICAM-1 expression for oligonucleotide-treated, cytokine-induced cells)-(basal ICAM-1 expression)/(ICAM-1 cytokine-induced expression)-(basal ICAM-1 expression)×100.

ISIS 1939 (SEQ ID NO: 15) and ISIS 2302 (SEQ ID NO: 22) markedly reduced ICAM-1 mRNA levels (detected by Northern blot analysis), but ISIS-1570 (SEQ ID NO: 1) decreased ICAM-1 mRNA levels only slightly.

Example 20

Experimental Metastasis Assay

To evaluate the role of ICAM-1 in metastasis, experimental metastasis assays were performed by injecting 1×10⁵ C8161 cells into the lateral tail vein of athymic nude mice. Treatment of C8161 cells with the cytokine TNF-α and interferon γ has previously been shown to result in an increased number of lung metastases when cells were injected into nude mice [Miller, D. E. and Welch, D. R., Proc. Am. Assoc. Cancer Res. 1990, 13, 353].

After 4 weeks, mice were sacrificed, organs were fixed in Bouin's fixative and metastatic lesions on lungs were scored with the aid of a dissecting microscope. Four-week-old female athymic nude mice (Harlan Sprague Dawley) were used. Animals were maintained under the guidelines of the NIH. Groups of 4–8 mice each were tested in experimental metastasis assays.

Example 21

Antisense Oligonucleotides ISIS 1570 and ISIS 2302 Decrease Metastatic Potential of C8161 Cells Treatment of C8161 cells with antisense oligonucleotides ISIS 1570 and ISIS 2302, complementary to ICAM-1, was performed in the presence of the cationic lipid, Lipofectin (Gibco/BRL, Gaithersburg, Md.). Cells were seeded in 60 mm tissue culture dishes at 10⁶ cells/ml and incubated at 37° C. for 3 days, washed with Opti-MEM (Gibco/BRL) 3 times and 100 μl of Opti-MEM medium was added to each well. 0.5 μM oligonucleotide and 15 μg/ml lipofectin were mixed at room temperature for 15 minutes. 25 μl of the oligonucleotide-lipofectin mixture was added to the appropriate dishes and incubated at 37° C. for 4 hours. The oligonucleotide-lipofectin mixture was removed and replaced with DME-F12 medium containing 10% fetal calf serum. After 4 hours, 500 U/ml TNF-α was added to the appropriate wells and incubated for 18 hours at which time cells were removed from the plates, counted and injected into athymic nude mice.

Treatment of C8161 cells with ISIS 1570 (SEQ ID NO: 1) or ISIS 2302 (SEQ ID NO: 22) decreased the metastatic potential of these cells, and eliminated the enhanced metastatic ability of C8161 which resulted from TNF-α treatment. Data are shown in Table 5.

TABLE 5

Effect of antisense oligonucleotides to ICAM-1 on experimental metastasis of human melanoma cell line C8161

| Treatment | No. Lung Metastases per Mouse (Mean + S.E.M.) |
|---|---|
| Lipofectin only | 64 ± 13 |
| Lipofectin + TNF-α | 81 ± 8 |
| ISIS-1570 + Lipofectin | 38 ± 15 |
| ISIS-2302 + Lipofectin | 23 ± 6 |
| ISIS-1570 + Lipofectin + TNF-α | 49 ± 6 |
| ISIS-2302 + Lipofectin + TNF-α | 31 ± 8 |

Example 22

Murine Models for Testing Antisense Oligonucleotides against ICAM-1

Many conditions which are believed to be mediated by intercellular adhesion molecules are not amenable to study in humans. For example, allograft rejection is a condition which is likely to be ameliorated by interference with ICAM-1 expression, but clearly this must be evaluated in animals rather than human transplant patients. Another such example is inflammatory bowel disease, and yet another is neutrophil migration (infiltration). These conditions can be tested in animal models, however, such as the mouse models used here.

Oligonucleotide sequences for inhibiting ICAM-1 expression in murine cells were identified. Murine ICAM-1 has approximately 50% homology with the human ICAM-1 sequence; a series of oligonucleotides which target the mouse ICAM-1 mRNA sequence were designed and synthesized, using information gained from evaluation of oligonucleotides targeted to human ICAM-1. These oligonucleotides were screened for activity using an immunoprecipitation assay.

Murine DCEK-ICAM-1 cells (a gift from Dr. Adrienne Brian, University of California at San Diego) were treated with 1 μM of oligonucleotide in the presence of 20 μg/ml DOTMA/DOPE solution for 4 hours at 37° C. The medium was replaced with methionine-free medium plus 10 dialyzed fetal calf serum and 1 μM antisense oligonucleotide. The cells were incubated for 1 hour in methionine-free medium, then 100 μCi/ml $^{35}$S-labeled methionine/cysteine mixture was added to the cells. Cells were incubated an additional 2 hours, washed 4 times with PBS, and extracted with buffer containing 20 mM Tris, pH 7.2, 20 mM KCl, 5 mM EDTA, 1% Triton X-100, 0.1 mM leupeptin, 10 μg/ml aprotinin, and 1 mM PMSF. ICAM-1 was immunoprecipitated from the extracts by incubating with a murine-specific ICAM-1 antibody (YN1/1.7.4) followed by protein G-sepharose. The immunoprecipitates were analyzed by SDS-PAGE and autoradiographed. Phosphorothioate oligonucleotides ISIS 3066 and 3069, which target the AUG codon of mouse ICAM-1, inhibited ICAM-1 synthesis by 48% and 63%, respectively, while oligonucleotides ISIS 3065 and ISIS 3082, which target sequences in the 3'-untranslated region of murine ICAM-1 mRNA inhibited ICAM-1 synthesis by 47% and 97%, respectively. The most active antisense oligonucleotide against mouse ICAM-1 was targeted to the 3'-untranslated region. ISIS 3082 was evaluated further based on these results; this 20-mer phosphorothioate oligonucleotide comprises the sequence (5' to 3') TGC ATC CCC CAG GCC ACC AT (SEQ ID NO: 83).

Example 23

Antisense Oligonucleotides to ICAM-1 Reduce Inflammatory Bowel Disease in Murine Model System A mouse model for inflammatory bowel disease (IBD) has recently been developed. Okayasu et al., *Gastroenterology* 1990, 98, 694–702. Administration of dextran sulfate to mice induces colitis that mimics human IBD in almost every detail. Dextran sulfate-induced IBD and human IBD have subsequently been closely compared at the histological level and the mouse model has been found to be an extremely reproducible and reliable model. It is used here to test the effect of ISIS 3082, a 20-base phosphorothioate antisense oligonucleotide which is complementary to the 3' untranslated region of the murine ICAM-1.

Female Swiss Webster mice (8 weeks of age) weighing approximately 25 to 30 grams are kept under standard conditions. Mice are allowed to acclimate for at least 5 days before initiation of experimental procedures. Mice are given 5% dextran sulfate sodium in their drinking water (available ad libitum) for 5 days. Concomitantly, ISIS 3082 oligonucleotide in pharmaceutical carrier, carrier alone (negative control) or TGF-β (known to protect against dextran sulfate-mediated colitis in mice) is administered. ISIS 3082 was given as daily subcutaneous injection of 1 mg/kg or 10 mg/kg for 5 days. TGF-β was given as 1 μg/mouse intracolonically. At 1 mg/kg, the oligonucleotide was as effective as TGF-β in protecting against dextran-sulfate-induced colitis.

Figure 15:
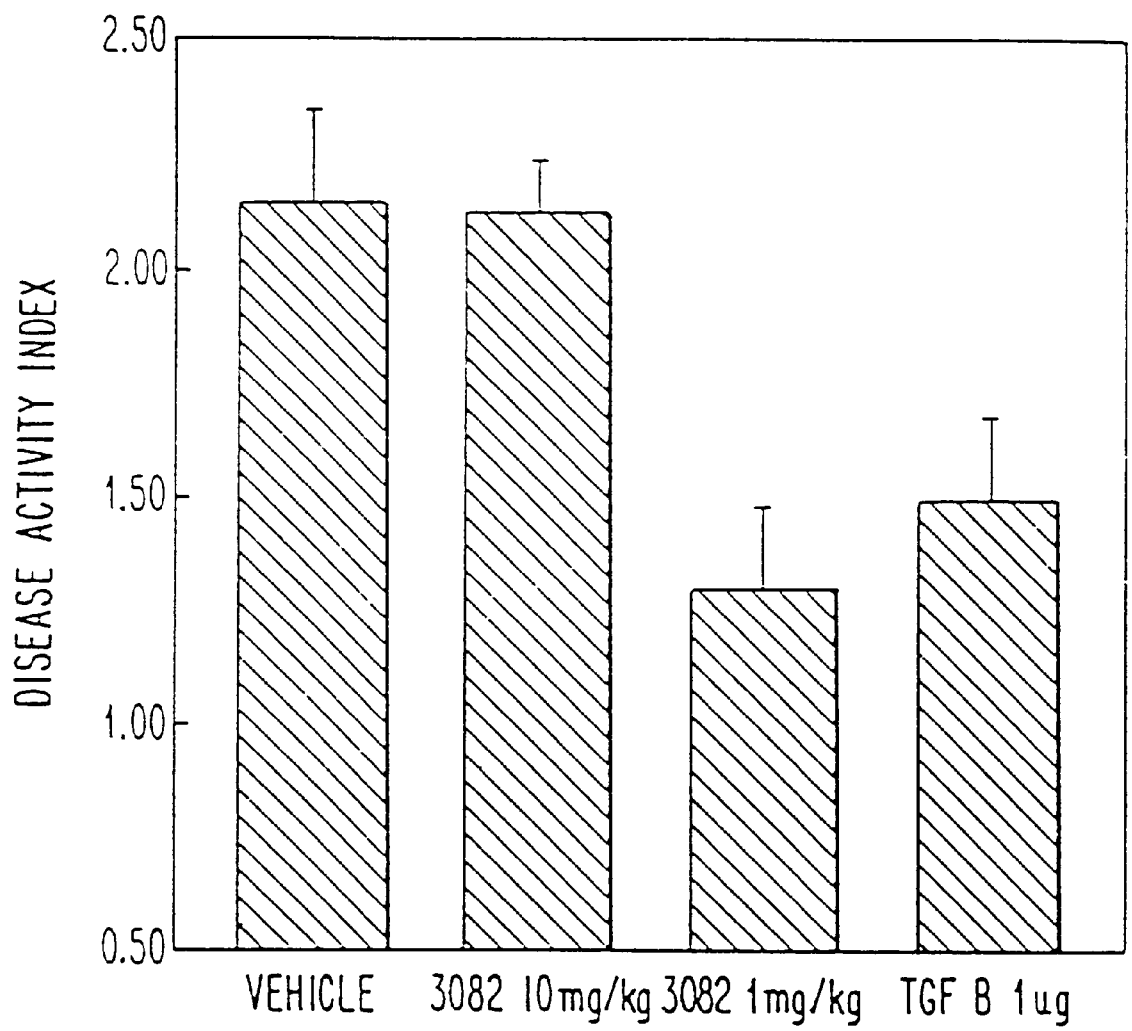
FIG. 15 is a bar graph showing the effect of ISIS 3082 on dextran sulfate (DSS)-induced inflammatory bowel disease.

Mice were sacrificed on day 6 and colons were subjected to histopathologic evaluation. Until sacrifice, disease activity was monitored by observing mice for weight changes and by observing stools for evidence of colitis. Mice were weighed daily. Stools were observed daily for changes in consistency and for presence of occult or gross bleeding. A scoring system was used to develop a disease activity index by which weight loss, stool consistency and presence of bleeding were graded on a scale of 0 to 3 (0 being normal and 3 being most severely affected) and an index was calculated. Drug-induced changes in the disease activity index were analyzed statistically. The disease activity index has been shown to correlate extremely well with IBD in general. Results are shown in FIG. 15. At 1 mg/kg, the oligonucleotide reduced the disease index by 40%.

Example 24

Antisense Oligonucleotide to ICAM-1 Increases Survival in Murine Heterotopic Heart Transplant Model To determine the therapeutic effects of ICAM-1 antisense oligonucleotide in preventing allograft rejection the murine ICAM-1 specific oligonucleotide ISIS 3082 was tested for activity in a murine vascularized heterotopic heart transplant model. Hearts from Balb/c mice were transplanted into the abdominal cavity of C3H mice as primary vascularized grafts essentially as described by Isobe et al., *Circulation* 1991, 84, 1246–1255. Oligonucleotides were administered by continuous intravenous administration via a 7-day Alzet pump. The mean survival time for untreated mice was 9.2±0.8 days (8, 9, 9, 9, 10, 10 days). Treatment of the mice for 7 days with 5 mg/kg ISIS 3082 increased the mean survival time to 14.3±4.6 days (11, 12, 13, 21 days).

Example 25

Antisense Oligonucleotide to ICAM-1 Decreases Leukocyte Migration

Leukocyte infiltration of tissues and organs is a major aspect of the inflammatory process and contributes to tissue damage resulting from inflammation. The effect of ISIS 3082 on leukocyte migration was examined using a mouse model in which carrageenan-soaked sponges were implanted subcutaneously. Carrageenan stimulates leukocyte migration and edema. Effect of oligonucleotide on leukocyte migration in inflammatory exudates is evaluated by quantitation of leukocytes infiltrating the implanted sponges. Following a four hour fast, 40 mice were assigned randomly to eight groups each containing five mice. Each mouse was anesthetized with METOFANE™ and a polyester sponge impregnated with 1 ml of a 20 mg/ml solution of carrageenan was implanted subcutaneously. Saline was administered intravenously to Group 1 at 10 ml/kg four hours prior to sponge implantation and this served as the vehicle control. Indomethacin (positive control) was administered orally at 3 mg/kg at a volume of 20 ml/kg to Group 2 immediately following surgery, again 6–8 hours later and again at 21 hours post-implantation. ISIS 3082 was administered intravenously at 5 mg/kg to Group 3 four hours prior to sponge implantation. ISIS 3082 was administered intravenously at 5 mg/kg to Group 4 immediately following sponge implantation. ISIS 3082 was administered intravenously at 5 mg/kg to Groups 5, 6, 7 and 8 at 2, 4, 8 and 18 hours following sponge implantation, respectively. Twenty-four hours after implantation, sponges were removed, immersed in EDTA and saline (5 ml) and squeezed dry. Total numbers of leukocytes in sponge exudate mixtures were determined.

The oral administration of indomethacin at 3 mg/kg produced a 79% reduction in mean leukocyte count when compared to the vehicle control group.

A 42% reduction in mean leukocyte count was observed following the administration of ISIS 3082 at 5 mg/kg four hours prior to sponge implantation (Group 3). A 47% reduction in mean leukocyte count was observed following the administration of ISIS 3082 at 5 mg/kg immediately following sponge implantation (Group 4). All animals appeared normal throughout the course of study.

Example 26

Oligonucleotide Labeling

In some of the following experiments antisense oligonucleotides were labeled in order to detect the presence of and/or measure the quantity thereof in samples taken during the course of the in vivo pharmacokinetic studies described herein. Although radiolabeling by tritium exchange is one preferred means of labeling antisense oligonucleotides for such in vivo studies, a variety of other means are available for incorporating a variety of radiological, chemical or enzymatic labels into oligonucleotides and other nucleic acids.

Essentially, the procedure of Graham et al. (*Nucleic Acids Research*, 1993, 21:3737) was used to label oligonucleotides by tritium exchange. Specifically, about 24 mg of oligonucleotide was dissolved in a mixture of 200 uL of sodium phosphate buffer (pH 7.8), 400 µL of 0.1 mM EDTA (pH 8.3) and 200 µL of deionized water. The pH of the resulting mixture was measured and adjusted to pH 7.8 using 0.095 N NaOH. The mixture was lyophilized overnight in a 1.25 mL gasketed polypropylene vial. The oligonucleotide was dissolved in 8.25 µL of beta-mercaptoethanol, which acts as a free radical scavenger (Graham et al., 1993, *Nucleic Acids Research*, 21:3737), and 400 µL of tritiated $H_2O$ (5 Ci/gram). The tube was capped, placed in a 90° C. oil bath for 9 hours without stirring, and then briefly centrifuged to remove any condensate from the inside lid of the tube. (As an optional analytical step, two 10 µL aliquots (one for HPLC analysis, one for PAGE analysis) were removed from the reaction tube; each aliquot was added to a separate 1.5 mL standard microfuge tube containing 490 µL of 50 uM sodium phosphate buffer (pH 7.8). The oligonucleotide mixture is then frozen in liquid nitrogen and transferred to a lyophilization apparatus wherein lyophilization was carried out under high vacuum, typically for 3 hours. The material was then resuspended in mL of double-distilled $H_2O$ and allowed to exchange for 1 hour at room temperature. After incubation, the mixture was again quick frozen and lyophilized overnight (as an optional analytical step, about 1 mg of the oligonucleotide material is removed for HPLC analysis). Three further lyophilizations were carried out, each with approximately 1 mL of double-distilled $H_2O$, to ensure the removal of any residual, unincorporated tritium. The final resuspended oligonucleotide solution is transferred to a clean polypropylene vial and assayed. The tritium labeled oligonucleotide is stored at about –70° C.

As is well known in the art, a variety of means are available to label oligonucleotides and other nucleic acids and to separate unincorporated label from the labeled nucleic acid. For example, double-stranded nucleic acids can be radiolabeled by nick translation and primer extension, and a variety of nucleic acids, including oligonucleotides, can be terminally radiolabeled by the use of enzymes such as T4 polynucleotide kinase or terminal deoxynucleotidyl transferase (see, generally, Chapter 3 In: *Short Protocols in Molecular Biology*, 2d Ed., Ausubel et al., eds., John Wiley & Sons, New York, N.Y., pages 3–11 to 3–38; and Chapter 10 In: *Molecular Cloning: A Laboratory Manual*, 2d Ed., Sambrook et al., eds., pages 10.1 to 10.70). It is also well known in the art to label oligonucleotides and other nucleic acids with nonradioactive labels such as, for example, enzymes, fluorescent moieties and the like (see, for example, Beck, 1992, *Methods in Enzymology*, 216:143; and Ruth, Chapter 6 In: *Protocols for Oligonucleotide Conjugates* (*Methods in Molecular Biology*, Volume 26) Agrawal, S., ed., Humana Press, Totowa, N.J., 1994, pages 167–185).

Example 27

Additional Oligonucleotides Targeted to the Coding Region of Human ICAM-1

The oligonucleotides in Table 6 were designed and synthesized as phosphorothioate oligodeoxynucleotides. As is true for other oligonucleotides targeted to human ICAM-1 cited herein, these oligonucleotides were designed to be complementary to the human ICAM-1 sequence as shown in FIG. 1.

The oligonucleotides shown in Table 6 are all complementary to the coding region of ICAM-1.

TABLE 6

| ISIS # | Sequence | SEQ ID NO: |
|---|---|---|
| 16851 | CTTGTGTATAAGCTGGCC | 86 |
| 16853 | CCCGGACAATCCCTCTCG | 87 |
| 16854 | TCTGCTGGGAATTTTCTG | 88 |
| 16855 | CACATTGGAGTCTGCTGG | 89 |
| 16856 | CTCGGGCAATGGGTTCCC | 90 |
| 16857 | TTAGACACTTGAGCTCGG | 91 |
| 16858 | ACAGTCACTGATTCCCCG | 92 |
| 16859 | ATCTCGAGTGACAGTCAC | 93 |
| 16860 | CACAGAGGTAGGTGCCCT | 94 |
| 16861 | CTCCCCTTGAGTGCTCCT | 95 |
| 16862 | TGACAATCTCATACCGGG | 96 |
| 16863 | CCACAGTGATGATGACAATC | 97 |
| 16865 | TACGTGCTGAGGCCTGCA | 98 |
| 16866 | GGCGGTTATAGAGGTACG | 99 |
| 16867 | CCTGTTGTAGTCTGTATTTC | 100 |
| 16868 | CCGGTAGGTGTAGCTGCA | 101 |
| 16869 | CTGTTGTATCTGACTGAG | 102 |
| 16870 | GATCAGATGCGTGGCCTA | 103 |

Example 28

Flow Cytometry and RNA Analysis of ICAM-1 Expression in HUVEC Cells

Human umbilical vein endothelial cells (HUVEC) were treated with oligonucleotide at 50 nM for 4 hours at 37° C. with 10 µg/mL LIPOFECTIN™ in OPTI-MEM™, followed by TNF-α induction of ICAM-1 expression at 5 ng/mL in EGM medium for 20 hours at 37° C. A portion of the cells were then fluorescently labeled with anti-ICAM-1-FITC or anti-ICAM-1-PE, and cell surface expression was assessed using flow cytometry. The RNA was extracted from the remainder of the cells using CATRIMOX-14 reagent (Iowa Biotechnology, Iowa City, Iowa.), and 10 µg of each sample's total RNA was separated by 1% agarose gel electrophoresis and transferred to a membrane. The blot was then probed with radiolabeled ICAM-1 and G3PDH probes, and the resulting bands were quantitated on a PHOSPHORIMAGER™ (Molecular Dynamics, Sunnyvale Calif.). Results of treated cells were compared to basal controls (no TNF-α induction, no oligonucleotide) and induced controls (TNF-α induction, no oligonucleotide). Results were expressed as percent control protein expression. For protein analysis, the results were calculated from flow cytometry results according to the formula:

$$\% \text{ control protein expression} = F_o - F_b / F_i - F_b$$

where $F_o$=mean oligonucleotide-treated fluorescence, $F_b$=mean basal fluorescence, and $F_i$=mean induced fluorescence. The results are shown in Table 7.

For RNA analysis, the ICAM-1 and G3PDH bands from the blots were quantitated and expressed as percent control, using the following formula:

$$\% \text{ control protein expression} = [ICAM_o - ICAM_b / G3PDH_o] \text{ divided by } [ICAM_i - ICAM_b / G3PDH_i],$$

where $ICAM_o$=oligonucleotide-treated ICAM-1 value, $ICAM_b$=basal ICAM-1 value, $G3PDH_o$=oligonucleotide-treated G3PDH value, $ICAM_i$=induced ICAM-1 value, and $G3PDH_i$=induced G3PDH value.

The results are shown in Table 7. ISIS 12344 is a scrambled control oligonucleotide with a phosphodiester backbone and a 2'-O-methoxyethyl modification on every nucleotide.

TABLE 7

| ISIS # | Sequence | % control expression ICAM-1 protein | % inhibition ICAM-1 protein | % control expression ICAM-1 RNA | % inhibition ICAM-1 RNA | SEQ ID NO: |
|---|---|---|---|---|---|---|
| 2302 | GCCCAAGCTGGCATCCGTCA | 23.1 | 76.9 | 22.2 | 77.8 | 22 |
| 12344 | GATCGCGTCGGACTATGAAG | 115.2 | — | 92.3 | 07.7 | 104 |
| 16851 | CTTGTGTATAAGCTGGCC | 42.1 | 57.9 | 40.7 | 59.3 | 86 |
| 16853 | CCCGGACAATCCCTCTCG | 49.1 | 50.9 | 50.2 | 49.8 | 87 |
| 16854 | TCTGCTGGGAATTTTCTG | 80.6 | 19.4 | 56.7 | 43.3 | 88 |
| 16855 | CACATTGGAGTCTGCTGG | 41.9 | 58.1 | 49.0 | 51.0 | 89 |
| 16856 | CTCGGGCAATGGGTTCCC | 70.8 | 29.2 | 75.4 | 24.6 | 90 |
| 16857 | TTAGACACTTGAGCTCGG | 71.5 | 28.5 | 50.4 | 49.6 | 91 |
| 16858 | ACAGTCACTGATTCCCCG | 35.3 | 64.7 | 32.5 | 67.5 | 92 |
| 16859 | ATCTCGAGTGACAGTCAC | 35.1 | 64.9 | 34.0 | 66.0 | 93 |
| 16860 | CACAGAGGTAGGTGCCCT | 33.3 | 66.7 | 33.5 | 66.5 | 94 |
| 16861 | CTCCCCTTGAGTGCTCCT | 46.7 | 53.3 | 53.5 | 46.5 | 95 |
| 16862 | TGACAATCTCATACCGGG | 66.2 | 33.8 | 84.2 | 15.8 | 96 |
| 16863 | CCACAGTGATGATGACAATC | 61.5 | 38.5 | 50.5 | 49.5 | 97 |
| 16865 | TACGTGCTGAGGCCTGCA | 21.6 | 78.4 | 18.7 | 81.3 | 98 |
| 16866 | GGCGGTTATAGAGGTACG | 37.4 | 62.6 | 43.7 | 56.3 | 99 |
| 16867 | CCTGTTGTAGTCTGTATTTC | 74.2 | 25.8 | 35.0 | 65.0 | 100 |
| 16868 | CCGGTAGGTGTAGCTGCA | 50.5 | 49.5 | 40.9 | 59.1 | 101 |
| 16869 | CTGTTGTATCTGACTGAG | 46.3 | 53.7 | 38.6 | 61.4 | 102 |
| 16870 | GATCAGATGCGTGGCCTA | 32.6 | 67.4 | 39.5 | 60.5 | 103 |

Dose-response curves were generated for ISIS 16865, 16870 and 16860. IC$_{50}$s were calculated for these compounds as well as ISIS 2302. HUVECs were seeded in 12-well plates and treated at 80% confluence. Oligonucleotides were purified by polyacrylamide gel electrophoresis prior to treatment, and cells were incubated with oligonucleotide at doses of 100 nM, 50 nM, 25 nM, 12.5 nM or 6.25 nM for 4 hours at 37° C. with 10 µg/mL LIPOFECTIN™ in OPTI-MEM™. Cells were then induced with TNF-α at 5 ng/mL in EGM for 20 hours at 37° C. Fluorescent labeling was done with anti-ICAM-1-FITC, followed by protein analysis using flow cytometry. Results were calculated as percent of control as described above. ISIS 2302 demonstrated an IC50 of 15.7 nM. ISIS 16865, 16870 and 16860 demonstrated IC50s of 17.7, 20.0 and 82.9 nM, respectively.

It was later determined that ISIS 16860 contained a one-base mismatch to the target sequence, and the oligonucleotide sequence fully complementary to the human ICAM-1 sequence is GACAGAGGTAGGTGCCCT (SEQ ID NO: 105). It is anticipated, therefore, that an oligonucleotide having SEQ ID NO: 105 Would be even more active than ISIS 16860, and is therefore also a preferred embodiment of this invention.

Example 29

Antisense to ICAM-1 Prevents Intestinal Inflammation in Rat

Antisense oligonucleotide sequences for inhibiting rat ICAM-1 expression were identified and screened in rat L2 cells. The most active sequence, ISIS 9125, displayed an $EC_{50}$ of approximately 150 nm. ISIS 9125 (AGGGCCACTGCTCGTCCACA; SEQ ID NO: 106) is a phosphorothioate oligodeoxynucleotide targeted to the 3' UTR of rat ICAM-1.

HLA-B27 transgenic rats develop spontaneous enterocolitis in a conventional environment. In a placebo-controlled study of intestinal inflammation, ISIS 9125 was administered to these rats. Forty-two HLA-B27 transgenic rats were divided into four groups. Intraperitoneal doses of 0, 0.5, 1 and 5 mg/kg oligonucleotide were given to each group of 20 animals. Groups of 20 HLA-B27-negative control littermates were tested with the same oligonucleotide doses. Animals were dosed every two days from week 16 to week 20, and were euthanized at week 21 and necropsied. The control littermates all showed normal intestinal pathology in the five areas examined: gastric, duodenum, jejunum, cecum and colon. Inflammation of the cecum and colon was quantified using the thickness of the cecal or intestinal mucosa in mm. The means of the scoring were compared. The results are shown in Table 8.

TABLE 8

Prevention of intestinal inflammation in rats by antisense oligo that inhibits ICAM-1

| ISIS 9125 Dose (mg/kg) | HLA-B27 Transgenic Rats (n = 42) | | Normal rat control littermates (n = 40) | |
| --- | --- | --- | --- | --- |
| | (mm) Cecal inflammation | (mm) Colon inflammation | (mm) Cecal inflammation | (mm) Colon inflammation |
| 0 (saline) | 0.5 | 0.43 | Normal[a] | Normal[a] |
| 0.5 | 0.46[b] | 0.37[bc] | 0.18 | 0.24 |
| 1.0 | 0.48[bd] | 0.37[bd] | 0.17 | 0.23 |
| 5.0 | 0.42[de] | 0.34[bcd] | Normal[a] | Normal[a] |

[a] = Not measured due to normal histology.
[b] = p < 0.001 compared to placebo
[c] = p < 0.001 between 0.5 mg/kg and 5.0 mg/kg dose groups
[d] = p < 0.001 between 1.0 mg/kg and 5.0 mg/kg dose groups
[e] = p = 0.005 compared to placebo Antisense to ICAM-1 was effective in preventing inflammatory bowel disease. Treatment of HLA-B27 rats with antisense to ICAM-1 resulted in statistically significant, dose-responsive reductions in colonic and cecal inflammation.

Example 30

Identification of Rat Oligonucleotides in vitro

Oligonucleotide sequences for inhibiting rat ICAM-1 expression were identified and screened in rat L2 cells. The most active sequence, ISIS 9125 (SEQ ID NO: 106), displayed an EC50 of approximately 150 nm. Sense and scrambled control sequences had no activity at doses from 150 nm to 1 µM.

Example 31

Rat Kidney Allografts

Kidneys from Lewis rats were transplanted into ACI rats. Control rats (no oligonucleotide treatment) had a mean graft survival time of 8.5±1.0 days (7, 8, 8, 9, 9, 10 days). Rats treated with oligonucleotide ISIS 9125 alone (10 mg/kg per day) for 7 days had a mean graft survival time of 9.2±1.3 days (8, 9, 9, 11 days). Rats treated with oligonucleotide ISIS 9125 alone (10 mg/kg per day) for 14 days had a mean graft survival time of >18.3 days (18, >7, >30 days).

Example 32

Rat Kidney Allografts with Cyclosporin

Kidneys from Lewis rats were transplanted into ACI rats. Control rats (no oligo, no cyclosporin) had a mean graft survival time of 8.5±1.0 days (7, 8, 8, 9, 9, 9, 10 days). Cyclosporin alone (2 mg/kg daily for 7 days) increased graft survival time to 10.5±3.4 days (7, 9, 11, 15 days). Rats treated with oligonucleotide ISIS 9125 alone (10 mg/kg per day for 7 days) had a mean graft survival time of 9.25 days (8, 9, 9, 11 days). Rats treated with both cyclosporin (2 mg/kg×7 days) and oligonucleotide ISIS 9125 (10 mg/kg×7 days) had a mean graft survival time of >24.2 days (10, 12, 24, 30, >45 days). Treatment with a reduced cyclosporin dose of 1 mg/kg for 14 days (no oligonucleotide) gave a mean graft survival time of >17.0 days (15, 18, >18). This cyclosporin regimen in combination with ISIS 9125 (10 mg/kg, 14 days) gave a mean graft survival time of >30 days (>30, >30, >30).

Example 33

Rat Cardiac Allografts

Hearts from Lewis rats were transplanted into ACI rats using a modification of the method described for mice. Control rats (no oligonucleotide treatment) had a mean graft survival time of 8.8±0.8 days (8, 8, 9, 9, 9, 10 days). Rats treated with oligonucleotide ISIS 9125 alone (2.5 mg/kg for 7 days) had a mean graft survival time of 12.0±1.7 days (10, 13, 13 days), rats treated with oligonucleotide ISIS 9125 alone (5 mg/kg for 7 days) had a mean graft survival time of 10±3.0 days (7, 10, 13 days) and rats treated with ISIS 9125 alone (10 mg/kg per day for 7 days) had a mean graft survival time of 18.0±3.8 days (13, 16, 16, 18, 22, 23 days).

Example 34

Rat Cardiac Allografts with Cyclosporin

Hearts from Lewis rats were transplanted into ACI rats as above. Control rats (no oligo, no cyclosporin) had a mean graft survival time of 8.8±0.8 days (8, 8, 9, 9, 9, 10 days). Cyclosporin alone (2 mg/kg daily for 7 days) increased graft survival time to 13.7±1.5 days (12, 14, 15 days) and cyclosporin alone (4 mg/kg for 7 days) gave a graft survival time of 16.7±3.8 days (14, 15, 21 days). Rats treated with oligonucleotide ISIS 9125 alone (5 mg/kg for 7 days) had a mean graft survival time of 10±3.0 days (7, 10, 13 days) and rats treated with ISIS 9125 alone (10 mg/kg per day for 7 days) had a mean graft survival time of 18.0±3.8 days (13, 16, 16, 18, 22, 23 days). Rats treated with both cyclosporin (4 mg/kg×7 days) and oligonucleotide ISIS 9125 (10 mg/kg×7 days) had a mean graft survival time of 21.7±7.4 days (16, 19, 30 days).

Example 35

Effect of Anti-ICAM-1 Oligonucleotide ISIS 3082 or Monoclonal Antibodies on Pancreatic Islet Allograft Survival and Islet Function Fresh pancreatic islets were transplanted under the renal subcapsular space or embolized into the liver after portal vein injection into mice of another strain.

Graft survival: There were four treatment groups following kidney capsule transplantation. 1) Recipient mice receiving no immunosuppressive treatment (control) had a mean survival time (MST)±standard deviation of 10.7±2.3 days. 2) Recipient mice treated with anti-LFA-1 monoclonal antibody, 50 mg daily intraperitoneally (IP) for 7 days had a MST of 27.2±4.8 days, p<0.01. 3) Recipient mice treated with anti- ICAM-1 monoclonal antibody YN1/1.7.4, 100 μg IP daily for 7 days, had a MST of 21.9±2.0 days, p<0.01. 4) Recipient mice treated with anti-ICAM-1 oligonucleotide ISIS 3082 (SEQ ID NO: 83), 5 mg/kg/day IP via osmotic pump had a MST of 28.9±12 days, p<0.01.

After portal vein administration, control mice survived 11.2±2.6 days and ISIS 3082 oligonucleotide-treated mice had a MST of 30.0±18 days, p<0.01.

Glucose tolerance tests: On postoperative day 2, the oligonucleotide-treated group had lower mean blood sugars compared to controls at 30 minutes (142.6±72 vs. 231.3±53.8, p<0.05) and 45 minutes (100.4±68.4 vs. 199.5±62.1, p<0.5). On postoperative day 7, the oligonucleotide-treated group also had lower mean blood sugars compared to controls at 30 minutes (189±58.5 vs. 251.5±70.1, p<0.05) and 45 minutes 148.6±40.2 vs. 210.7±58.2, p<0.5).

Significant islet allograft prolongation was achieved by ICAM-1 blockade. ICAM-1 antisense oligonucleotide was effective in improving islet function as well as prolonging graft survival.

Further experiments were done, again transplanting pancreatic islets (C57BL/10 mice)under the renal subcapsular space of recipient C3H mice. Mean allograft survival time (MST) was determined either by death of recipient or the first of two consecutive non-fasting blood sugar levels greater than 100 mg/dL. For untreated (saline) controls the MST was 11.9±0.9 days. A 7-day IP infusion of ISIS 3082 at 5 mg/kg/day gave an MST of 30.5±12.3 days. A 7-day daily IP injection of 100 μg anti-ICAM-1 monoclonal antibody (American Type Culture Collection, Rockville Md.) extended MST to 41.6±34.1 days, which was only slightly improved by combination of ICAM-1 antibody with ISIS 3082 (MST 47.3±34 days). In contrast, while blockade of LFA-1 with 7 daily IP injections of 50 μg of anti-LFA-1 antibody gave a similar MST of 42.8±25.9 days, combination of ISIS 3082 and the anti-LFA-1 antibody gave a greatly increased survival of 74±12.6 days.

Results were similar in mice in which islets were embolized into the liver after portal vein injection. Untreated control MST was 11+2.1 days, a 7-day IP infusion of ISIS 3082 at 5 mg/kg/day gave an MST of 25.9±20.2 days. A 7-day daily IP injection of 100 μg anti-ICAM-1 monoclonal antibody (American Type Culture Collection, Rockville Md.) extended the MST to 18.2±1.6 days, which was only slightly improved by combination of ICAM-1 antibody with ISIS 3082 (MST 28.4±13.6 days). In contrast, while blockade of LFA-1 with 7 daily IP injections of 50 μg of anti-LFA-1 antibody gave an MST of 43.8±28.7 days, combination of ISIS 3082 and the anti-LFA-1 antibody gave a mean survival of 65.7±27.3 days.

In some studies, recipient mice (kidney capsule transplant) were treated for 7 days with 5 mg/kg/day of ISIS 3082, beginning either the day before transplantation (day −1) or on the day of transplantation (day 0). MST was prolonged to 23.5±4.0 days and 19.6±3.7 days, respectively. Pretreatment of donor alone with a single IP injection of 5 mg/kg ISIS 3082 on day −1 failed to affect allograft survival (MST=12.8±1.3 days). However, combined donor pretreatment on day −1 with recipient 7-day treatment starting on day −1 prolonged islet survival to 36.6±5. 3 days. Results were similar for portal vein transplants.

Thus combined treatment of both allograft donor and recipient may be a preferred embodiment of the present invention.

Example 36

Pharmacological Activity of ISIS 3082 in a Murine Model of Arthritis

Type II collagen-induced arthritis is regarded as one of the better models for rheumatoid arthritis in humans. Both diseases have a humoral and cellular immune response against type II collagen, specific MHC class II linkage and a pronounced acute phase response. In addition, the histological changes which occur in the synovium of animals with collagen-induced arthritis are similar to that observed in patients with active rheumatoid arthritis.

Type II collagen was purified from bovine articular cartilage according to published methods. Male DBA-1 mice (H-2q) were injected intradermally with 100 μg of fetal bovine collagen II, emulsified in Freund's complete adjuvant. On day 21 a booster injection was given. The antisense oligonucleotide, ISIS 3082, targeted to murine ICAM-1, was administered by intraperitoneal injection at either 5 mg/kg or 10 mg/kg at indicated times. Prednisolone was used as a positive control and was administered by oral gavage.

Animals were examined three times per week for signs of arthritis (swelling, limping, redness of paws). Animals exhibiting any of these symptoms were considered arthritic.

For X-ray analysis, animals were placed in a ventral position on Kodak X-Omat MA film and exposed with 28 kV, 125 mAs at a distance of 45 cm from the X-ray device. Eighteen joints per paw were evaluated using a binocular microscope. Arthritis signs were loss of bone walls, loss of metaphyseal bone density or destruction of the joint architecture. Each joint was given a rating of 0 (non-arthritic) or 1 (arthritic). A score of 1 meant that at least one side of the articulation showed a clear loss of the bone wall contour or a clear loss of metaphyseal bone density. The theoretical maximum score was 72 per animal (all joints in all four paws affected). All X-ray photographs were evaluated at least twice in a blinded fashion by one investigator. Serum amyloid P component and anti-collagen antibodies were determined. A clinical scoring system was used in addition to monitoring the relative number of arthritic animals, which allowed severity of disease to be evaluated (number of affected paws plus intensity of disease). Every paw was given a score between 1 and 4, where 0 is absence of any arthritis signs and 4 is severe arthritis with redness and swelling of the whole pw, limping and severely reduced function (lack of grasping when climbing) of the affected paws.

Ten identically treated animals per group were used. The statistical difference between groups was calculated using the non-parametric Mann-Whitney U-test. Statistical analysis was performed using the InStat computer program (GraphPad, San Diego Calif.).

Treatment with the mouse ICAM-1 antisense oligonucleotide, ISIS 3082 (SEQ ID NO: 83), was initiated three days after the initial immunization with collagen. Mice treated three times per week by intraperitoneal injection with 5 mg/kg ISIS 3082 exhibited a reduction in the percent arthritic animals and X-ray score, but this was not statistically significant. Increasing the dose of ISIS 3082 to 10 mg/kg resulted in a significant, though not complete, reduction in both percent arthritic animal (approximately 37% reduction compared to control)and X-ray scores (approximately 45% reduction compared to either of two unrelated control oligonucleotides, ISIS 1082 (GCCGAGGTCCATGTCGTACGC; SEQ ID NO: 107) Or ISIS 4189 (CAGCCATGGTTCCCCCCAAC; SEQ ID NO: 108). The scrambled control oligonucleotide, 4189, did not significantly affect either the number of animals developing arthritis or the X-ray scores. Prednisolone administered at a dose of 30 mg/kg/day by mouth was used as a positive control and suppressed the development of arthritis in 90% of the animals and significantly reduced the severity of disease as assessed by X-ray score.

Based upon these results the dosing interval of ISIS 3082 was increased to 5 times per week. ISIS 3082 at either 5 mg/kg or 10 mg/kg significantly reduced the number of animals which developed arthritis, and did so in a dose-dependent manner. At day 64, nearly 75% of the untreated control animals had developed arthritis, while less than 10% of the prednisolone-treated animals developed arthritis. For ISIS 3082, the 5 mg/kg dose reduced the number of arthritic animals to approximately 15% (approximately 20% of control) and the 10 mg/kg dose reduced the number of arthritic animals to below 5% (approximately 7% of control). The 5 mg/kg oligonucleotide dose reduced the arthritic score by 50% compared to control, and the 10 mg/kg dose reduced the arthritic score by 93%.

While we do not wish to be bound by theory, it is believed that ISIS 3082 may have partially affected the humoral response to collagen immunization, because the oligonucleotide, given at 10 mg/kg, was found to partially reduce the level of anti-collagen antibody production.

Example 37

ISIS 3082 Effects on Murine Endotoxin-induced Pneumonia

The presence of endotoxin within the distal airspaces of the lung induces an inflammatory response that results in the accumulation of neutrophils and in the formation of edema with 24 hours. This response is attributed to an induction of cytokine production, which subsequently induce upregulation of adhesion molecules, including ICAM-1, and emigration of neutrophils and, later, mononuclear cells. Kumasaka et al., 1996, *J. Clin. Invest.* 97, 2362–2367. The effect of ISIS 3082 on this ICAM-1 upregulation and subsequent inflammatory response was examined.

Mice were treated with endotoxin and oligonucleotide as described in Kumasaka et al., 1996, *J. Clin. Invest.* 97, 2362–2367. Briefly, anesthetized mice received an intravenous injection of ISIS 3082 into the tail vein at doses of 0, 1, 10, 30 or 100 mg/kg. Two hours after oligonucleotide treatment, endotoxin (100 µl of 2 mg/ml) was instilled into the airways via the trachea for mice sacrificed 4 hr after endotoxin treatment. Control mice received no endotoxin. For mice sacrificed 24 hr after endotoxin treatment, mice received injections of ISIS 3082 or saline either 2 hr before or 2 hr before and 4 hr after endotoxin treatment. Monoclonal antibody to murine ICAM-1 was also used for comparison. Endotoxin induced a fivefold increase in ICAM-1 mRNA in the lungs within four hours of instillation. This increase was inhibited by ISIS 3082 when given at 30 mg/kg or 100 mg/kg, but not at 1 or 10 mg/kg. When animals were studied at 24 hr after endotoxin treatment, there was still a significant increase in the ICAM-1 mRNA. This increase was inhibited when ISIS 3082 was given at a dose of 100 mg/kg both 2 hr before and 4 hr after endotoxin treatment, but not when given only 2 hr before. These results are shown in Kumasaka et al., 1996, *J. Clin. Invest.* 97, 2362–2367.

The effect of ISIS 3082 on neutrophil emigration and edema formation induced by endotoxin was examined histologically. In control mice treated with saline at 2 hr before and 4 hr after endotoxin treatment, 2.6% of the distal lung was occupied by emigrated neutrophils 24 hr after endotoxin treatment. In mice pre-treated with ISIS 1082, an unrelated control oligonucleotide (SEQ ID NO: 107), the value was similar, 1.98%. In the mice pretreated with SIIS 3082, only 0.82% of the distal lung was occupied by emigrated neutrophils ($p<0.05$), indicating that the ICAM-1 antisense oligonucleotide inhibited neutrophil emigration into the lung by 596. Similar results were obtained with monoclonal antibodies to ICAM-1.

The accumulation of edema was measured by extravascular albumin. The lungs of mice that were given ISIS 3082 but no endotoxin showed no increase in extravascular albumin. Intratracheal instillation of endotoxin induced a significant increase in edema formation that was not inhibited by either ISIS 1082 (control) or ISIS 3082.

Example 38

Effect of ISIS 2302 on Human Cytotoxic Dermatitis in Xenografts

Cytotoxic tissue injury in which lymphocytes destroy target epithelial cells is typical of potentially life-threatening conditions including certain autoimmune diseases and allograft rejection. In skin, this phenomenon can take the form of naturally occurring disorders including erythema multiforme and lichen planus as well as certain drug eruptions and graft-vs-host disease. Christofidou-Solomidou et al., 1997, *Am. J. Path.*, 150, 631–639. A human skin-murine chimera model has been developed by grafting neonatal human foreskin to immunocompromised (SCID) mice. A dermatitis remarkably similar to human lichen planus develops with the human xenografts after microinjection of heterologous human peripheral blood mononuclear cells (PBMC). The xenografts are infiltrated by PBMCs, the majority of which are CD3+ T cells. This phenomenon is called epidermotropism.

Mice were engrafted with human skin and treated with human peripheral blood mononuclear cells as described in Christofidou-Solomidou et al., 1997, *Am. J. Path.*, 150, 631–639. The antisense oligonucleotide, ISIS 2302, targeted to human ICAM-1, was injected subcutaneously into the flanks of transplanted SCID mice at a dose of 10 mg/kg/day for 5 days, and 2 days after the start of antisense injections, 100 units of IFN-gamma was injected into each graft in 50 µl of saline. Grafts were harvested and stained for ICAM-1 expression 48 hours later. In other experiments oligonucleotide was administered by osmotic pump at a dose of 250 µg/mouse/day for 14 days. As described by Christofidou-Solomidou et al., (*Am. J. Path.*, 150, 631–639), ISIS 2302 reduced IFN-gamma-induced ICAM-1 levels in the xenografts when injected subcutaneously into mouse flank daily ($P<0.05$) but did not affect the expression of HLA-DR, another cell surface molecule upregulated by IFN-gamma. A sense control oligonucleotide (reverse complement of ISIS 2302) had no effect on either ICAM-1 or HLA-DR expression. In mice administered oligonucleotide by continuous subcutaneous osmotic pump, epidermotropism of CD3+ T cells was significantly inhibited by ISIS 2302 but not by sense or saline controls. There appeared to be less cytotoxic injury in the ISIS 2302-treated animals. Christofidou-Solomidou et al., 1997, *Am. J. Path.*, 150, 631–639.

Example 39

Use of Liposomally Encapsulated ISIS 3082 of Animal Model for Multiple Sclerosis Multiple sclerosis (MS) is a slowly progressive demyelinating autoimmune disease (see, generally, *The Merck Manual of Diagnosis and Therapy*, 15th Ed., pp.1414–1417, Berkow et al., eds., Rahway, N.J., 1987). Experimental autoimmune encephalomyelitis (EAE) is an artificially induced demyelinating disease that is used as an animal model for MS (for a review, see Burkhardt et al., *Rheumatol. Int.*, 1997, 17, 91). While not wishing to be bound by any particular theory, it was hoped that an antisense oligonucleotide targeted to a cellular adhesion molecule, encapsulated in liposomes, would extravasate through inflamed sites in the blood-brain barrier (BBB), and would thus be useful for treating MS and other disorders of the central nervous system.

In order to evaluate the ability of the liposomes of the invention to treat EAE, liposomes (DMPG:DPPC:Chol, 5:57:38 mol %) encapsulating ISIS 3082 (1.5 or 3.8 mg/kg) were prepared. ISIS 3082 is targeted to, and inhibits the expression of, the murine gene encoding ICAM-1. Because ICAM-1 mediates cell:cell interactions in a variety of immune system-related contexts, it was believed that delivery of ISIS 3082 to appropriate sites in vivo might alleviate some or all of the autoimmunologial responses associated with MS.

Lipid stock solutions were prepared at 20 mg/mL in chloroform. For liposomes having DMPG:DPPC:Chol in a molar ratio of 5:57:38, for example, DMPG, DPPC and Chol were dispensed into a 30 mL round bottom flask as follows for 150 µmol of total lipid:

| Component | Mole Ratio | Mole % | mg lipid | mL stock lipid solution |
|---|---|---|---|---|
| DMPG | 0.263 | 5 | 5.2 | 0.258 |
| DPPC | 3 | 57 | 62.7 | 3.137 |
| Chol | 2 | 38 | 22.0 | 1.102 |

Chloroform was removed by evaporation using a rotary evaporator, heating at 60° C. with a moderate vacuum. The lipid material dried as a thin film on the flask wall. Evaporation was continued using high vacuum for an additional 30 minutes at 60° C.

Oligonucleotide (ISIS 3082) was dissolved in water to 100 mg/mL. The solution was made isotonic (80–310 mOsm) with the addition of a small quantity of 5M NaCl as needed. The final solution was filtered through a 0.22 µm membrane. Then, 0.5 mL of the resultant oligo solution was added to the flask containing the lipid film. The flask was rotated at 240 rpm at 60° C. for 5 minutes. The lipid suspension was vortexed heavily to form large multi-lamellar liposomes.

The liposomes were frozen by immersing the flask into a dry ice/acetone bath for 5 minutes. Thawing of the liposomes was accomplished by immersing the flask into a 60° C. water bath as necessary. The preceding freeze/thaw steps were repeated 5 times. The resulting liposome solution appeared "creamy."

Large multi-lamellar liposomes were converted into near-uniform unilamellar liposomes by either (1) physical extrusion through polycarbonate membranes (Avestin, Inc., Ottawa, Ontario, Canada) of defined porosity (e.g., 100 nm) or microfluidization with a Model 110 S microfluidizer (Microfluidics International Corp., Newton, Mass.). Either technique produces unilamellar liposomes of approximately 90 to about 110 nm in diameter.

Nonencapsulated oligonucleotide material was separated from the liposomes by gel permeation chromatography using a Superdex-200 column (Pharmacia Biotech, Inc., Piscataway, N.J.) equilibrated in phosphate-buffered saline, pH 7.4. Encapsulation recovery was typically 25–30% and the final ISIS 2503 concentration in the liposomes was about 7 mg/mL. The liposome fractions were pooled and filter-sterilized through a 0.2 µm membrane (Gelman Sciences, Inc., Ann Arbor, Mich.). Liposomes were stored at 4° C. EAE was induced in female (SJL×BALB/c)F$_1$ mice (The Jackson Laboratory, Bar Harbor, Me.) at 6 to 8 weeks of age essentially according to the method of Myers et al. (*J. Neuroimmunol.*, 1992, 41, 1). Groups of mice (n=7 unless otherwise noted) were injected s.c. in the hind footpads and the base of the tail with 50 to 100 ug of synthetic peptides corresponding to the primary encephalitogenic determinants (i.e., residues 139–151, HCLGKWLGHPDKF-amide) of proteolipid protein (PLP) for SJL and (SJL×BALB/c)F$_1$ mice (p13, Tuohy et al., *J. Immunol.*, 1989, 142, 1523; Multiple Peptide Systems, San Diego, Calif.). Antigen was emulsified in complete Freund's adjuvant (CFA, Difco, Detroit, Mich.) and fortified with 4 mg/mL of heat-killed H37Ra *Mycobacterium tuberculosis*. Mice were injected s.c. on days 0 and 2 and, at the same time, 500 ng of pertussis toxin (Sigma Chemical Co., St. Louis, Mo.) was administered i.v. Animals were given drinking water by hand during periods of paralysis.

The liposomal formulations were administered i.v. daily during disease progression. EAE was clinically assessed according to the procedures and criteria of Myers et al. (*J. Immunol.*, 1993, 151, 2252). In brief, disease severity incidence and time of onset were measured according to defined grades of symptoms, from Grade 0 (no detectable signs of EAE) to Grade 4 (total paralysis/moribund state) and Grade 5 (death). The "Mean Onset Day" of EAE is calculated from the first day that Grade 1 or higher EAE symptoms were noted in a particular mouse (averaged for the group). The "Mean Peak Severity" represents the average within an experimental group of the highest grade of EAE attained by each mouse.

The results demonstrate that liposomes encapsulating ISIS 3082 provide relief from the severest symptoms of EAE and delay the onset of the disease. With regard to the severity of the symptoms of the disease, the Mean Peak Severity was 2.6 Grade Units for the control group (n=5), to which empty liposomes were administered, compared to 1.57 Grade Units for the group given liposomally formulated ISIS 3082 at a dose of 3.8 mg/kg. In the case of the group given liposomally formulated ISIS 3082 at a dose of 1.5 mg/kg, the symptoms of EAE were graded as relatively mild during the early course of the disease. Subsequently, however, 3 mice died fairly late in the course of EAE; although the cause of death in these instances was not determined, and may have been due to, e.g., pathogenic infection, the deaths of these animals resulted in them receiving a grade of 5 on the EAE symptom scale. As a result, the Mean Peak Severity of the group receiving liposomally formulated ISIS 3082 at a dose of 3.8 mg/kg was similar to that of the control group (2.5 Grade Units). In any event, however, ISIS 3082 formulated in liposomes extended the Mean Onset Day of EAE at either dose (14.7 days, 1.5 mg/kg dose; 16.7 days, 3.8 mg/kg dose) relative to the Mean Onset Day (13.2 days) for the control group.

These results demonstrate that inhibition of a cellular adhesion molecule, such as ICAM-1, by a bioactive agent (including, but not limited to, an antisense compound) results in a delay in the onset of, and a reduction in the severity of the symptoms of, autoimmune diseases such as MS.

Example 40

In Vitro Testing of Oligonucleotide Penetration of Skin

Male and female hairless SKH1 mice 6–8 weeks old were obtained from Charles River Laboratories (Wilmington, Mass.) and were euthanized using carbon dioxide asphyxiation. Fresh and frozen skins were mounted on a vertical Franz diffusion cell (Permegear, N.J.) with each skin having a diffusional area of 0.636 $cm^2$. Receptor chambers having a volume of 5.1 ml were filled with isotonic phosphate buffer (pH 7.2) containing 0.1% (v/v) of 36% aqueous formaldehyde as preservative. Receptor temperatures were maintained at 37±0.5° C. and stirred continuously at 600 rpm. The skins were allowed to hydrate for 1 hour prior to starting an experiment. Experiments generally were performed at 24 hours.

Penetration enhancers/vehicles were added into the donor compartment for 1 hour and then washed off with 500 μl of methanol. The total amount of enhancer/vehicle that was added to each donor compartment was 10 μl (unless otherwise noted). After methanol wash, the skin was lightly wiped and blown dry to remove any visible moisture. In an experiment studying the effect of methanol on penetration enhancement, no wash was performed. Also, in experiments studying the effects of pretreatment time, the amount of time the enhancer was allowed to stay on the skin was varied (i.e., 30 minutes or 1, 2 or 3 hours).

Oligonucleotide (ISIS 2302) was added on top of the enhancer solution. ISIS 2302 was added to each donor compartment as a 200 μl normal saline solution containing both 1 mg of unlabeled oligonucleotide and approximately 300,000 DPM of radiolabeled oligonucleotide. Epidermal, dermal and receptor penetration values are expressed as the ratio of the counts penetrated versus the control counts.

The following chemicals were used as enhancers/vehicles: propylene glycol, dimethyl sulfoxide (DMSO), isopropyl myristate, Azone, MIGLYOL™ 818, oleic acid, d-limonene, limonene, 1-dodecyl-2-pyrrolidinone, 1-methyl-2-pyrrolidinone, menthone, ethanol and TWEEN-40.

Statistical analyses were performed on Excel using Students t-test (two-sample assuming equal variances) along with averages, standard deviations, and standard errors. Female hairless mice were preferentially used as the studies progressed due to an uncharacterized but recurring follicular infection that appeared to preferentially target male mice.

The best epidermal penetration enhancers for the delivery of ISIS 2302 were shown to be isopropyl myristate (1.67%, 2.14% and 3.11%), menthone (2.93%), ethylene glycol (2.41%), 1-methyl-2-pyrrolidinone (2.41%), d-limonene (1.78%–1.55%), MIGLYOL 818® (1.62%) and dimethyl sulfoxide (1.56%). In contrast, for dermal penetration, the best penetration enhancers are Tween 40 (1.42%), oleic acid (~1.0%), d-limonene (0.72%), 1-dodecyl-2-pyrrolidinone (0.67%), DMSO (0.38%) and 1-methyl-2-pyrrolidinone (0.25%). There is no little or no correlation between epidermal penetration enhancement and dermal penetration enhancement, an effect which may be due to different mechanisms of action of delivery to the two layers, rates of penetration, the duration of the experiments, the duration of enhancer pretreatments, or a combination of such factors.

Experiments with Azone were carried out to examine how much of a factor methanol is in the delivery of ISIS 2302. Azone pretreatment with a methanol wash resulted in epidermal and dermal penetration values of 1.31% and 0.16%, respectively, whereas the values for experiments without methanol values were 0.72% and 0.13% for epidermal and dermal penetration, respectively. Ethanol had little effect on the penetration of ISIS 2302 when limonene was used as an enhancer. Higher volumes of limonene and isopropyl myristate did not result in an increase in the penetration.

Example 41

Cream Formulations and Effects of Oligonucleotide Chemistries

In order to formulate a cream from isopropyl myristate, its viscosity was increased using oil soluble agents and surfactants such as glyceryl monosterate, stearic acid and bees wax. Oligonucleotide was dissolved in a water phase consisting of aqueous surfactants and viscosity imparting agents such as polyoxyl-40 stearate and polyethylene glycol derivatives. Cream formulations consisting of water (36–45% w/w), isopropyl myristate (30–48% w/w), glyceryl monostearate (10–16% w/w), polyoxyl-40 stearate (0–156 w/w) and antimicrobial preservatives (benzyl alcohol, methylparaben, propylparaben) were studied in vitro for penetration. Oligonucleotide was thoroughly mixed with the cream formulations to give a final concentration of 1 mg oligonucleotide for each 149 mg cream. Appropriate controls were used to determine the radioactivity per mg of cream.

The cream formulation with 30% isopropyl myristate resulted in an epidermal penetration of 1.66% and a dermal penetration of 1.57% for ISIS 2302. Similar penetration values were seen with cream formulation containing 48% isopropyl myristate.

ISIS 15839 is an antisense oligonucleotide having the same sequence as ISIS 2302 (GCCCAAGCTGGCATCCGTCA; SEQ ID NO: 22), in which every cytosine is a 5-methylcytosine and wherein the eight residues at the 3' end (shown in bold) comprise a 2'-methoxyethoxy modification (other residues are 2'-deoxy). A cream formulation of ISIS 15839 with 30% isopropyl myristate showed a very high dermal penetration, i.e., 11% of the applied dose. These results demonstrate that oligonucleotides of different chemical compositions penetrate the skin when formulated in isopropyl myristate cream formulations.

Example 42

In Vivo Testing of ICAM-1 Suppression by ISIS 3082 Formulations Administered to Skin The oligonucleotide ISIS 3082 (SEQ ID NO: 83), which is targeted to the murine ICAM-1 gene, was mixed with empty ("f") liposomes or encapsulated into ("e") liposomes as set forth below to determine the degree of ICAM-1 suppression effected thereby:

1. DOPE-f Liposomes (DOPE:DPPC:Chol; 20:60:20% w/w) mixed with ISIS 3082 to obtain 10 mg/mL ISIS 3082;
2. ISIS 3082 solution at 10 mg/mL;
3. DOPE-f Liposomes (DOPE:DPPC:Chol; 20:60:20% w/w) mixed with ISIS 3082 to obtain 10 mg/mL ISIS 3082;
4. DOPE-e Liposomes (DOPE:DPPC:Chol; 20:60:20% w/w) with ISIS 3082 encapsulated in the liposomes, not purified, to obtain 10 mg/mL ISIS 3082;
5. DMPG-f Liposomes (DMPG:DPPC:Chol; 20:60:20% w/w) mixed with ISIS 3082 to obtain 10 mg/mL ISIS 3082;
6. DMPG-e Liposomes (DMPG:DPPC:Chol; 20:60:20% w/w) with ISIS 3082 encapsulated in the liposomes, not purified, to obtain 10 mg/mL ISIS 3082;
7. DMPC-f Liposomes (DMPC:DPPC:Chol; 20:60:20% w/w) mixed with ISIS 3082 to obtain 10 mg/mL ISIS 3082;
8. DMPC-e Liposomes (DMPC:DPPC:Chol; 20:60:20% w/w) with ISIS 3082 encapsulated in the DMPC liposomes, not purified, to obtain 10 mg/mL ISIS 3082;
12. No treatment, phorbol myristate acetate (PMA) positive control; and
13. No treatment, no PMA control (basal).

The liposomes were prepared by hydrating a dry film of lipids in a glass container with either phosphate buffered saline at pH 7.4 or a 10 mg/mL solution of ISIS 3082 in PBS. The hydrated lipids were then extruded 21 times through a 50 nm membrane to form small liposomes with final lipid concentration of ~100 mg/mL, drug concentration of ~10 mg/mL and particle size of ~100 nm.

Liposome formulations were applied to the back of hairless mice using a HILLTOP™ chamber that keeps the formulation in place. Three mice were tested in each group. Forty-eight hours after the formulation application, the treated part of the skin was challenged with PMA to induce ICAM-1. Mice were sacrificed 4 hours after PMA application and skin collected for Northern analyses of the mRNA levels.

The results with ISIS 3082 mixed with empty liposomes are as follows. The DOPE (1 and 2) and DMPG liposomes show about 30% to about 40% reduction in PMA-induced ICAM-1 expression, whereas the phosphate buffered saline solution formulation and DPPC liposomes show less than 10% reduction. The results prove that ISIS 3082 penetrates the skin when mixed with liposomes and that the penetration of drug thus achieved is sufficient to cause a biological effect.

When ISIS 3082 was encapsulated in the liposomes, the liposome formulations comprising DOPE, DPPC or DMPG and encapsulating ISIS 3082 all show a 30–50% reduction in ICAM-1 mRNA, showing that ISIS 3082 penetrates the skin when encapsulated in liposomes and that the penetration of drug thus achieved is sufficient to cause a biological effect.

Example 43

Preclinical Toxicological Analysis of ISIS 2302 in Animals

Doses of ISIS 2302 (SEQ ID NO: 22) up to 100 mg/kg and doses of ISIS 3082 (SEQ ID NO: 83), the murine analog of 2302, have been administered i.v. to mice every other day for 4 weeks, and doses of ISIS 2302 up to 50 mg/kg i.v. every other day for 4 weeks to monkeys (Henry et al , 1997, Toxicology 120,145–155) The sequence of ISIS 2302 is complementary to the simian ICAM-1 mRNA at 19 or 20 positions, and therefore ISIS 2302 has substantial pharmacological activity in simian endothelial cells in vitro, demonstrating an IC50 approximately twice that of an oligonucleotide with perfect homology to the monkey target sequence. The major toxicological finding in mice, as with other phosphorothioate oligonucleotides, was a nonspecific immune stimulation. In monkeys, nonspecific immune stimulation was not observed. However, dose-related and reversible changes in blood clotting time (prolongation of the activated partial thromboplastin time or aPTT) and alternative pathway complement activation) were seen at doses of 10 and 50 mg/kg. Both effects were clearly related to peak plasma drug levels, with a threshhold of approximately 50 µg/ml for complement activation and 30 µg/ml for prolongation of aPTT. Doses of 2 mg/kg produced no remarkable alterations. Minor structural changes in the kidney were also seen at doses of 10 and 50 mg/kg. In rodents and primates, pharmacokinetic studies demonstrated similar behavior, with plasma distribution half life on the order of 30–45 minutes but with "tissue half-lives" of 1–3 days. These results suggested that an every-other-day dose regimen would be appropriate for humans, with minimal tissue accumulation.

In planning initial exposure in humans, it was believed that a peak plasma level of 10–15 µg/ml, or approximately 25–30% of the threshhold for complement activation in monkeys, would provide an adequate margin of safety for initial Phase 1 dosing in humans. Extrapolating from monkey data, it was projected that a 2 mg/kg two-hour infusion would produce such peak drug levels in humans. Furthermore, 2 mg/kg was within the therapeutic range in animal models.

Standard mutagenicity studies of ISIS 2302 in bacteria and CHO cells were unremarkable. Animal reproductive studies with both ISIS 2302 and the murine analog have shown no evidence of teratogenicity or effect on fertility.

To explore the feasibility of subcutaneous injection, initial pharmacokinetic studies with this route of administration were undertaken in rat and monkey. A phosphate buffered saline formulation given subcutaneously at 1–2 mg/kg in a volume of 1 ml or less gave about 50% plasma bioavailability as compared to intravenous administration, with a time to maximal plasma concentration of 1–3 hours. One month, every-other-day subcutaneous toxicity studies with the PBS formulation were therefore undertaken in the mouse and the monkey. Tolerability and toxicity paralleled that in the intravenous studies, and 20 mg/kg at a concentration of 80 mg/mL, the highest monkey dose level, was well tolerated, without significant local (injection site), regional (lymph nodes) or laboratory findings. Plasma bioavailability was dose and drug concentration-dependent, but concentrations of 50 mg/mL and above and doses within or greater than the anticipated therapeutic range in humans (0.5–2 mg/kg) produced approximately 50% bioavailability.

Example 44

Preparation of Microemulsion and Cream Formulations of ISIS 2302

Microemulsion formulations were prepared, with concentrations of ISIS 2302 (SEQ ID NO: 22) at either 4 mg/ml or 12 mg/ml. A microemulsion of ISIS 2302 was prepared essentially according to the procedures of Panayiotis (*Pharm. Res.*, 1984, 11:1385). An aliquot of 0.6 ml of ISIS 2302 stock solution (200 mg/ml) was transferred to a 30 ml beaker containing 1.0 ml of Tween 80 (Sigma Chemical Company St. Louis, Mo.). Next, a mixture of 6.3 ml of Captex 355 (Abitec Corp., Janesville, Wis.) and 2.1 ml of Capmul MCM (Abitec Corp., Janesville, Wis.) was added to the beaker. The resultant solution was stirred until a clear solution was formed.

A water-in-oil microemulsion of ISIS 2302 was prepared essentially by adding the oil phase to the aqueous phase with adequate mixing. The aqueous phase was prepared by mixing 1 ml of a 100 mg/ml solution of ISIS 2302 and 1 ml of Tween 80 (Sigma Chemical Company St. Louis, Mo.). The oil phase was prepared by mixing 3 parts of Captex 355 (Abitec Corp., Janesville, Wis.) and 1 part of Capmul MCM (Abitec Corp., Janesville, Wis.). The oil phase was added to the aqueous phase with adequate stirring until the resultant mixture was a clear solution.

A water-in-oil cream formulation of ISIS 2302 was prepared by first preparing the two phases. A 4 ml aliquot of the ISIS 2302 stock solution (100 mg/ml) was transferred to a 10 ml beaker and warmed to 70° C. In a 30 ml beaker were placed 1 gram of Grill 3 (Croda, U.S.), 3 ml Captex 355 (Abitec Corp., Janesville, Wis.), and 3 ml of Labrasol (Gattefosse, France) and this mixture also warmed to 70° C. The aqueous solution of oligonucleotide was then poured slowly into the oil phase with vigorous mixing. Upon cooling to ambient temperature the desired water-in-oil cream formulation was obtained.

An oil-in-water cream formulation of ISIS 2302 was prepared by first preparing the two phases. A 2.3 ml aliquot of the ISIS 2302 stock solution (100 mg/ml) was mixed with 0.5 ml of Tween 80 (Sigma Chemical Company St. Louis, Mo.) in a 30 ml beaker and warmed to about 70° C. In a 10 ml beaker were placed 100 mg. of Grill 3 (Croda, U.S.), 1 ml Captex 355 (Abitec Corp., Janesville, Wis.), and 1 ml of Labrasol (Gattefosse, France) and this mixture also warmed to about 70° C. The oil phase was then poured into the aqueous solution of oligonucleotide with vigorous mixing. Upon cooling to ambient temperature the desired oil-in-water cream formulation was obtained.

Example 45

Bioavailability of ISIS 2302 Administered by Intrejejunal Instillation

The absolute bioavailability of oligonucleotide was assessed following intrajejunal instillation in several formulations.

Sprague-Dawley rats weighing 250–300 g were used. After overnight fasting, the rats were anesthetized with 5% pentobarbital (50 mg/kg) by intraperitoneal injection. After a midline abdominal incision was made, the small intestine was pulled out and injection site was located (2 cm after the ligament of Treitz). The intestine was put back into the body carefully. An aliquot of 0.5 mL drug formulation (10 mg of ISIS 2302) was then injected via a 27 gauge needle. Muscle was then surgically closed and skin was clipped after injection. 300 mL of blood was collected by cannula at each sampling time point (0.5, 1.0, 2.0 and 3.0 h) from the femoral vein. The rats were sacrificed in a carbon dioxide chamber 24 hours after dosing. Radioactivity of plasma samples were measured.

Five formulations were evaluated. Two solution formulations were prepared. Formulation 1a was prepared by dissolving ISIS 2302 and a combination of CDCA and fatty acid penetration enhancers to the desired concentrations. Formulation 1b was prepared by dissolving ISIS 2302 and a combination of UDCA and fatty acid penetration enhancers to the desired concentrations.

Formulation 1c was prepared as an emulsion of ISIS 2302 in a mixture of labrasol, aptex and Grill 3. Formulation 1d was also prepared as an emulsion that is similar to Formulation 1c with one difference in that CDCA and fatty acid penetration enhancers were incorporated into Formulation 1d at the same concentrations as were present in Formulation 1a. Formulation 1e was likewise prepared as an emulsion that is similar to Formulation 1c with one difference in that UDCA and fatty acid penetration enhancers were incorporated into Formulation 1e at the same concentrations as were present in Formulation 1b. All five formulations contained ISIS 2302 at a final concentration of 20 mg/ml.

The results of absolute bioavailability of ISIS 2302 as determined in this study are summarized in Table 9.

TABLE 9

Absolute Bioavailability of ISIS 2302 Following Intrajejunal Instillation in Rats

| Formulation | Composition | Absolute Bioavailability |
|---|---|---|
| 1a solution | ISIS 2302 + CDCA + Fatty acids | 14.6% (n = 5) |
| 1b solution | ISIS 2302 + UDCA + Fatty acids | 12.4% (n = 2) |
| 1c emulsion | ISIS 2302 + Labrasol + Captex + Grill 3 | 20.3% (n = 5) |
| 1d emulsion | ISIS 2302 + CDCA + Fatty acids + Labrasol + Captex + Grill 3 | 27.7% (n = 3) |
| 1e emulsion | ISIS 2302 + UDCA + Fatty acids + Labrasol + Captex + Grill 3 | 27.7% (n = 3) |

When a control solution of ISIS 2302 was administered no significant amount of oligonucleotides was found to be absorbed at steady state. In contrast, when ISIS 2302 was formulated as a solution that contained a mixture of fatty acid and bile salts (Formulations 1a and 1b) a significant amount of oligonucleotide was found to be absorbed and bioavailable in the systemic circulation. The absolute bioavailability of ISIS 2302 was found to be 14.6% from Formulation 1a (containing a mixture of CDCA and fatty acid penetration enhancers) and 12.4% from Formulation 1b (containing a mixture of UDCA and fatty acid penetration enhancers). The simple emulsion, Formulation 1c, that is devoid of any penetration enhancers was also effective in making a significant portion of the ISIS 2302 oligonucleotide bioavailable (absolute bioavailability of 20.4%).

When formulated as emulsions that contained a combination of penetration enhancers, the bioavailability of ISIS 2302 was found to increase even further. Formulation 1d, which is an emulsion containing a combination of CDCA and fatty acid penetration enhancers, afforded an absolute bioavailability of ISIS 2302 to the tune of 27.7%. A similar bioavailability of the oligonucleotide was also found when emulsion Formulation 1e containing UDCA instead of CDCA, as in Formulation 1d, was evaluated.

Example 46

Preparation of Enema Formulations

To evaluate the delivery and mucosal penetration of oligonucleotides into the colon following rectal delivery, the following formulations were prepared (Table 10). Solution and emulsion formulations of ISIS 2302 were prepared. Additives used in the formulations included saline, hydroxypropyl methyl cellulose (HPMC), carrageenan, Vitamin E a-tocopheryl polyethyelene glycol 1000 succinate (TPGS), Tween 80 and sorbitol.

Formulation 2a: A solution of ISIS 2302 was prepared in sterile saline at the desired concentration and used for in vivo evaluation.

Formulation 2b: A solution of ISIS 2302 and hydroxypropyl methyl cellulose (HPMC) was prepared such that the final concentration of ISIS 2302 was identical to that in Formulation 2a and the concentration of HPMC was 1.5%.

Formulation 2c: A solution of ISIS 2302 was prepared, as for Formulation 2a, containing 1.0% carrageenan and 2.5% Vitamin E TPGS.

TABLE 10

ISIS 2302 Formulations

| Formulation | Composition |
|---|---|
| 2a | ISIS 2302 in Saline |
| 2b | ISIS 2302 + 1.5% Hydroxypropyl Methyl Cellulose (HPMC) |
| 2c | ISIS 2302 + 1.0% Carrageenan + 2.5% Vitamin E a-Tocopheryl Polyethylene Glycol 1000 Succinate (TPGS) (Source: Eastman Chemical Company, NY) |
| 2d | ISIS 2302 in a water-in-oil emulsion |
| 2e | ISIS 2302 + 0.5% Tween 80 + 0.75% HPMC |
| 2f | ISIS 2302 + 5% Sorbitol + 0.75% HPMC |

Formulation 2d: A water-in-oil emulsion of ISIS 2302 was prepared following the general methods in the above example.

Formulation 2e: This formulation was prepared by mixing ISIS 2302, Tween 80 and HPMC in the appropriate quantities so as to afford a mixture that had the desired concentration of ISIS 2302, 0.5% Tween 80 and 0.75% HPMC.

Formulation 2f: This formulation was prepared by mixing ISIS 2302, Sorbitol and HPMC in the appropriate quantities so as to afford a mixture that had the desired concentration of ISIS 2302, 5% Tween 80 and 0.75% HPMC.

Example 47

Evaluation of Enema Formulations

Formulations of oligonucleotide were evaluated via rectal administration as enemas to laboratory beagle dogs. Following a period of overnight fasting, test dogs were first administered a cleansing enema and then dosed with a sample of the test formulation. The enema formulation was applied via a Foley catheter and held for a period of 1 h. In order to assess colonic tissue delivery and uptake of oligonucleotide, colon tissue biopsies were performed on the test animal, 3 h and 24 h after dosing. Tissue samples were processed and the amount of oligonucleotide present in the tissue assessed by capillary gel electrophoresis (CGE) and immunohistochemical (IHC) analyses.

Six formulations of ISIS 2302 as prepared in the previous example (Formulations 2a–2f) were administered to dogs via rectal enemas and the local distribution of ISIS 2302 in colonic tissue was determined by CGE and IHC at 3 h and 24 h following dosing. The results are shown in Table 11.

TABLE 11

Local Colonic Tissue Distribution of ISIS 2302 Following Rectal Enema in Dog

| Formu- | Immunohistochemistry | | CGE (mg/g) | |
|---|---|---|---|---|
| lation | 3 h | 24 h | 3 h | 24 h |
| 2a | ++++ | — | 782.2 ± 664.2 | NA |
| 2b | ++++ | — | 660.4 ± 439.6 | 6.8 ± 5.0 |
| 2c | ++++ | — | 557.8 ± 212.2 | 2.5 ± 1.4 |
| 2d | ++++ | — | 224.1 ± 78.3 | 1.2 ± 0.7 |
| 2e | ++++ | — | 620.7 ± 368.1 | 6.0 ± 5.9 |
| 2f | ++++ | — | | |

"++++" indicates strong immunohistochemical staining using a primary antibody to ISIS 2302;
"—" indicates no significant staining compared to background levels.

Example 48

Determination of Bioavailability of Oligonucleotides following Intrajejunal and Rectal administration of Formulations In order to determine the bioavailability of formulations of oligonucleotide drugs two different modes of administration were studied.

For intrajejunal instillation, Sprague-Dawley rats weighing 250–300 g were used. After overnight fasting, the rats were anesthetized with 5% pentobarbital (50 mg/kg) by intraperitoneal injection. After a midline abdominal incision was made, the small intestine was pulled out and injection site was located (2 cm after the ligament of Treitz). The intestine was put back into the body carefully. An aliquot of 1.0 mL drug formulation was then injected via a 27 gauge needle. Muscle was then surgically closed and skin was clipped after injection.

For rectal administration, test rats were first administered a cleansing enema following a period of overnight fasting, and then dosed with a sample of the test formulation. The enema formulation was applied via a catheter and held for a period of 1 hour.

In order to assess bioavailability of oligonucleotide, samples are processed and the amount of oligonucleotide present assessed by capillary gel electrophoresis (CGE) and HPLC analyses.

The absolute bioavailability of ISIS 2302 was determined following intrajejunal instillation in five Sprague-Daley rats and following rectal administration in seven rats. For intrajejunally administered ISIS 2302, the absolute bioavailability was 20.3% (n=5). For rectally administered ISIS 2302, the absolute bioavailability was 24.5% (n=7).

Example 49

Limiting Viral Dissemination via Inhibition of Cellular Adhesion

Adhesion molecules have been proposed to be mediators of viral dissemination in several systems. For example, in the case of the retrovirus, human immunodeficiency virus (HIV), studies have demonstrated that adhesion of infected cells to immobilized ICAM-1 induces HIV replication (Shattock et al., *J. Infect. Dis.*, 1996, 174, 54), and surface expression of ICAM-1 (CD54) is enhanced in T cell lines carrying the virus (Imai et al., *Int. J. Cancer*, 1993, 55, 811).

The association between adhesion molecules and human cytomegalovirus (CMV) is of particular interest. CMV is a member of the Herpesviridae family that is associated with worldwide morbidity and mortality in immunocompromised hosts (Sedmak et al., *Arch. Virol.*, 1995, 140, 111). CMV is known to infect multiple tissues and organs, but its mechanism(s) of dissemination are largely uncharacterized. Viral dissemination by the bloodstream has been suggested, but acceptance of the notion of hematogenous spread of CMV has been limited due to the fact that in vitro studies generally indicate that peripheral blood mononuclear cells (PBMCs) do not support the complete viral reproductive cycle. However, PBMCs can be infected by CMV by contact with virally infected endothelial cell monolayers (Waldman et al., *J. Infect. Dis.*, 1995, 171, 263).

ICAM-1 and other cellular adhesion molecules are up-regulated in fibroblasts infected with CMV (Grundy et al., *Immunol.*, 1993, 78, 405). Effective antiviral treatment with ganciclovir or foscarnet accentuates such up-regulation of adhesion molecules, suggesting that CMV immediate/early gene expression, which is not blocked by such treatment, is responsible for such CMV-mediated up-regulation of adhesion molecules (Craigen et al., *Transplantation*, 1996, 62, 1102).

CMV has been associated with allograft rejection, particularly transplant-associated arteriosclerosis. However, the role CMV plays in the development of transplant-associated arteriosclerosis remains unclear (Knight et al., *Transplantation*, 1997, 63, 1366). Even effective antiviral treatment of the transplant recipient with, e.g., ganciclovir or foscarnet, might not block allograft rejection as CMV infected cells could continue to provide a focus of proinflammatory activity, which could contribute to undesirable immunopathology and/or accentuate graft rejection or graft-versus-host disease (Craigen et al., *Transplantation*, 1996, 62, 1102). Treatment of transplant tissues ex vivo, and/or of transplant recipients in vivo, with inhibitors of cellular adhesion molecules (alone or in combination with antiviral agents) is expected to modulate viral-mediated up-regulation of such adhesion molecules and thus block such undesirable events.

In order to investigate the role of adhesion molecules such as ICAM-1 in viral dissemination, and to determine the potential of antisense oligonucleotides to prevent viral dissemination, the following experiments were carried out. ISIS 15537 is a uniform 2'-O-methoxyethyl modified oligonucleotide I which every backbone linkage is a phosphorothioate linkage and every cytidine is a 5-methylcytidine. This oligonucleotide has SEQ ID NO: 84, the same sequence as ISIS 3067. ISIS 14118 (GACGCATCGCGCCTACATCG; SEQ ID NO: 109) is an unrelated control oligonucleotide.

Endothelial cells were treated with ISIS 15537 or control oligonucleotide ISIS 14118 prior to CMV inoculation, incubated an additional 48 hours post-inoculation and examined by FACS. The results demonstrate specific and significant attenuation of CMV-mediated ICAM-1 expression by these antisense compounds. The attenuation of ICAM-1 expression was reflected by reduced adhesion of $^{5}$Cr-labeled T cells to oligonucleotide-treated CMV endothelial cell monolayers. These assays were performed essentially as described by Bennett et al. (*J. Immunol.*, 1994, 152, 3530) except that (1) T cells were used instead of HL-60 cells as adherent cells and (2) $^{51}$Cr was used instead of calcein to label the adherent cells.

Human Clinical Trials of an Antisense Oligonucleotide Targeting ICAM-1

Example 50

Phase 1 Clinical trials of ISIS 2302

The purpose of the first clinical trial with ISIS 2302 was to assess the safety and pharmacokinetics of intravenous administration of an anti-ICAM-1 antisense oligodeoxynucleotide in healthy subjects before commencing pilot therapeutic trials in target disease states. This was a double-blind, placebo-controlled, randomized (3:1, drug: placebo) study. Four healthy male volunteers were enrolled in each of seven single dose (0.06, 0.12, 0.24, 0.5, 1.0, 1.5 and 2.0 mg/kg) and multiple dose groups (0.2, 0.5, 1.0 and 2.0 mg/kg every other day for four doses). Groups were studied in a rising-dose fashion, and multiple dosing commenced after the first five single groups had completed the trial. ISIS 2302 (or sterile normal saline as placebo) was administered by intravenous infusion in a volume of 80 ml over two hours. Subjects remained recumbent, with continuous ECG monitoring for four hours after the beginning of each infusion. Before and at intervals after each infusion, supine blood pressure and pulse, clotting screen including aPTT, thrombin time, prothrombin time, serum complement split products C3a and C5a, neutrophil count, urine microproteins, and standard laboratory safety screen (hematology, blood biochemistry and urinalysis) were measured. Serum samples were collected from multiple dose groups at 14 and 21 days after the last infusion to be analyzed for the presence of antibodies to ISIS 2302. Blood samples were taken for measurements of plasma concentration of ISIS 2302 before and up to 24 hours after the beginning of infusion.

Complement split products were measured by commercially available C3a and C5a assay kits (Amersham). Plasma was examined for the presence of anti-ISIS 2302 antibodies using a modification of a previously described ELISA methodology. Lacy and Voss, 1989, *J. Immunol. Methods*, 116, 87–98. Uncoated areas on plates were blocked with 26 non-fat dried milk powder. Medium from a hybridoma cell line producing monoclonal antibodies which recognize ISIS 2302 served as a positive control. ISIS 2302 does not appear to be antigenic; consequently, monoclonal antibodies to ISIS 2302 had to be raised by immunizing mice with ISIS 2302 conjugated to keyhole limpet hemocyanin. Drug analysis was performed by capillary gel electrophoresis (CGE) as described by Leeds et al., 1996, *Anal. Biochem.*, 235, 36–43. A phosphorothioate standard oligonucleotide composed of 27 thymidine nucleotides (T27) was added to both plasma and urine as an internal standard. The linear range of concentrations of oligonucleotides detectable in plasma using this method was 10 nM to 20 $\mu$M (approximately 0.07 to 140 $\mu$g/ml).

During two-hour single infusions of ISIS 2302, metabolites co-migrating with synthesized n-1, n-2 and n-3 chain-shortened forms of the intact drug appeared rapidly in plasma, constituting 20% of total oligonucleotide after 30 minutes of infusion. Interestingly, the relative proportion of total oligonucleotide constituted by full length drug, n-1, n-2 and n-3 forms remained relatively constant during the two hours of infusion and for at least the four additional hours post-infusion during which metabolites could be measured. Intact drug therefore constituted the majority of oligonucleotide present at all times at which drug or metabolites were detectable.

Urine samples from the 1.0 and 2.0 mg/kg multiple dose groups were analyzed for concentrations of intact drug and metabolites. Although very low concentrations of drug or metabolites were excreted in urine (less than 0.5% of the total drug administered was excreted in the first six hours), intact drug and n-1, n-2 and n-3 forms could be measured, and the quantity of shorter forms could be estimated from electropherograms. The amount of intact drug excreted over six hours after the beginning of infusion averaged approximately 0.05% of the administered dose, and the estimated total excretion of parent drug and metabolites in this time period was less than 0.5% of the total dose.

Example 51

Phase 2 Clinical Trials of ISIS 2302—Overview

ISIS 2302 is being evaluated in Phase 2 trials for patients with five inflammatory disease indications: Crohn's disease, ulcerative colitis (both of which are forms of inflammatory bowel disease), rheumatoid arthritis, psoriasis and prophylaxis of acute renal allograft rejection. All but the psoriasis study are placebo controlled and double-masked. ISIS 2302 at doses of 0.5 to 2 mg/kg is administered three times weekly for 2 to 4 weeks by two-hour intravenous infusion. This dose range was chosen based on available toxicology data and experience with normal volunteers; furthermore, 2 mg/kg is within the therapeutic range in mice, and the similar pharmacokinetics seen in mice and humans made it likely that this would be a therapeutic dose in humans. The Phase 2a studies were therefore designed as fixed dose within patient, dose escalation studies, beginning at 0.5 mg/kg and escalating to 1 and 2 mg/kg every other day i.v. in successive cohorts.

Example 52

Human Clinical Studies on Intravenously Administered ISIS 2302 in Crohn's Disease A double-blinded, placebo-controlled, 20 patient study has validated the use of ISIS 2302 in treatment of Crohn's disease in particular, and other inflammatory diseases in general, particularly inflammatory bowel diseases. This was a randomized trial (3:1 ISIS 2302:placebo) that enrolled steroid-dependent patients with moderately active Crohn's disease despite background corticosteroids ($\leq$40mg prednisone or equivalent per day). Moderately active was defined as a Crohn's Disease Activity Index (CDAI) between 200 and 350. CDAI is composed of 8 variables derived from a patient diary, physical examination, and laboratory examination. At baseline (start of study), the average CDAI for patients in the ISIS 2302 treatment group was 294 and for patients in the placebo group, CDAI was 330. Background 5-ASA drugs were permitted. Corticosteroids and 5-ASA drugs were to remain stable during the treatment period and for one month of follow up. Thereafter, corticosteroid doses were adjusted by the investigator according to blinded clinical judgment. The primary efficacy measure was the CDAI, and a secondary measure the Endoscopic Index of Severity (EIS). CDAI was measured weekly through Day 40, again at Day 60, and monthly thereafter. Colonoscopy was performed, and EIS was calculated, at baseline and at Days 26, 60 and 120. A clinical remission was defined as a CDAI below 150. Mucosal biopsies were also taken for determination of histologic scoring, quantitation of cellular adhesion molecule expression, and possibly determination of tissue drug levels.

Isis 2302 was supplied at a concentration of 100 mg/mL in vials filled to 1.2 mL, containing 100 mg (1.0 mL) of recoverable drug in a saline solution. A dosage of, e.g., 2 mg/kg) was injected under sterile conditions into 100 mL of normal saline and infused over a two hour period by an infusion pump at a rate of 50 mL/hour via a free-running catheter in a peripheral vein. If a central line has been inserted for purposes other than this study, the line could be utilized for study drug administration. Placebo (saline) was provided in matching vials and also diluted into 100 mL for infusion. The patient's weight on Day 1 served as the basis for determining the dosage of study drug to be administered throughout the study. The patient's weight at Day 1, volume of study drug injected into the diluent, the volume of diluent and the volume of infusate injected and duration (elapsed time) of infusion of study drug were recorded. Vital signs were recorded just prior to each infusion and at 30 minute intervals during the infusion and the hour following. The patients were observed for an hour after infusion ended.

Results:

At the end of the trial (end of month 6), 5 of 15 (33%) of ISIS 2302-treated patients and no placebo-treated patients were completely weaned from corticosteroids. This was a highly statistically significant steroid sparing effect (p=0.0001).

Seven of 15 ISIS 2302-treated patients (47%) and no placebo-treated patients were in remission at the end of the 26-day treatment period, as assessed by a Crohn's Disease Activity Index (CDAI) below 150. At day 180 (end of study), five of these seven ISIS 2302-treated patients remained in remission, and none of the placebo-treated patients were in remission. ISIS 2302 also showed excellent patient tolerability.

Changes in intestinal mucosal ICAM-1 expression from Day 1 to Day 26 were measured for patients in each dose group. Mucosal biopsies 1 mm×1 mm were placed in OCT and snap-frozen. Representative frozen sections were dried, fixed, and immunohistochemically stained for CD54 (ICAM-1) using the DAB procedure and an anti-ICAM-1 antibody from Pharmingen, San Diego Calif. Slides were read in blinded fashion. Day 26 slides were compared to Day 0 slides and scored as improved (+1), without change (0) or worse (−1) for anti-ICAM-1 staining. Non-inflamed tissue was compared to non-inflamed, and inflamed to inflamed tissue where possible. Results are shown in Table 12.

TABLE 12

| | Outcome | | | |
|---|---|---|---|---|
| Dose | Improved | No Change | Worsened | Total |
| Placebo | 1 | 2 | 2 | 5 |
| 0.5 mg/kg | 1 | 2 | 0 | 3 |
| 1 mg/kg | 0 | 3 | 0 | 3 |
| 2 mg/kg | 7 | 2 | 0 | 9 |

Another clinical trial of ISIS 2302 in Crohn's disease is being conducted to assess the efficacy and tolerability of 1–5 intravenous infusions of ISIS 2302 in steroid-dependent Crohn's disease. Daily infusions of 2 mg/kg of 30 days have been safely administered to cynomolgus monkeys. Five daily i.v. infusions of 1 mg/kg have also been well tolerated in 2 patients with Crohn's disease, and 2 mg/kg in 3 Crohn's patients. As the plasma elimination half-life is under 60 minutes in humans, a daily regimen of 2 mg/kg should be well tolerated. A once-daily infusion of 2 mg/kg for 5 days is predicted to achieve similar tissue levels as a 2–4 week course of 2 mg/kg i.v. 3 times weekly. This study compares three different treatment regimens of a 2-hour infusion of ISIS 2302 (2 mg/kg daily×1, 3 and 5) in 120 patients with steroid-dependent moderately active Crohn's disease.

Example 53

Phase 1 trial of subcutaneously administered ISIS 2302

A Phase 1 subcutaneous study of ISIS 2302 was conducted in normal volunteers. In the first phase of the study, the tolerability and pharmacokinetics of a single 1 ml subcutaneous injection of ISIS 2302 at concentrations ranging from 50–200 mg/ml were administered in double-blinded, placebo controlled, randomized (3:1; study drug:placebo) fashion to cohorts of four subjects. All concentrations produced mild injection site erythema, edema and induration that lasted for a few days. This was more of a clinical observation than a patient complaint, and it appeared that all doses were adequately tolerated. Preliminary analysis indicates that plasma bioavailability appears to be about 50%, with a time to maximal concentration of 1–3 hours. Regimens of 1 mg/kg every other day for 4 doses or weekly for 4 weeks were marginally tolerated, with evidence of very low grade complement activation (C3a only and not C5a) and low grade lymphadenopathy in addition to the mild injection site reactions described above. A 2 mg/kg bolus regimen was not well tolerated.

An additional trial (30 patients/arm) of subcutaneously administered ISIS 2302 in Crohn's disease is ongoing to examine the effect of lower dose subcutaneous administration five days a week for 1, 2 and 4 weeks.

Example 54

Clinical Trial of ISIS 2302 in Ulcerative Colitis Patients

In ulcerative colitis patients, a Phase 2 trial is commencing with more intense, shortened courses of therapy compared to that used for Crohn's disease (two weeks—week 1 is 5 daily infusions and week two is three every-other-day infusions). Results are not yet available.

Example 55

Topical Administration of ISIS 2302 by Enema in Ulcerative Colitis Patients

Topical administration of ISIS 2302 by enema is being pursued in patients with disease of the left colon, which is accessible by enema. Aminosalicylates and steroids have proven to be effective by enema. In pre-clinical studies, ISIS 2302 given by enema demonstrated good tolerability and tissue uptake.

Example 56

Effect of Intravenous Administration of ISIS 2302 on Psoriasis

In psoriasis, a Phase 2a open labelled study is complete, in which patients were given 13 intravenous infusions of ISIS 2302 over 26 days. Patients have moderately active (5–40% body surface area involvement) plaque-type psoriasis vulgaris, resistant to medium potency topical corticosteroids. All dose groups) 0.5–2 mg/kg) showed a 20–30% reduction in the Psoriasis Area and Severity Index (PASI).

Example 57

Phase 2 trial of ISIS 2302 in Rheumatoid Arthritis

In rheumatoid arthritis, a 43-patient placebo-controlled, double-blinded study is nearing completion, in which patients were given 13 infusions over 26 days. Patients with active disease (at least 10 swollen joints plus at least two of the following: tender joints $\geq 12$, morning stiffness at least one hour, ESR $\geq 25$ for males and 35 for females) were dosed at 0.5, 1.0 and 2.0 mg/kg. The treatment regimen, duration of treatment and followup period were the same as for the Crohn's disease study. Efficacy was assessed by changes in swollen joint count, tender joint count, patient global assessment, physician global assessment, and pain by a visual analog scale.

Example 58

Phase 1 and 2 Trials of ISIS 2302 in Renal Transplant Patients

In prevention of acute renal transplant (cadaveric allograft) rejection, the Phase 1 segment in stable renal transplant patients is complete, with excellent tolerability being demonstrated. The 38-patient, phase 2 segment is underway. This is a single-center, double-blinded, placebo controlled, randomized (3:1) study which differs from the other phase 2a studies in four respects: 1) since most patients come from a distance, therapy is limited to two weeks for logistical reasons; 2) The study is divided into a Phase 1 and a Phase 2 segment; 3) two lower dose groups (0.05 and 0.1 mg/kg) were included; and 4)due to the perioperative nature of the treatment, the first two infusions are administered over 6 hours, the second two infusions over 4 hours and the remaining three infusions over 2 hours to reduce maximum plasma concentrations of drug during the immediate perioperative and postoperative periods. In the Phase 1 segment now complete, patients with stable cadaveric renal allografts at least 6 months post-transplant were administered a single 6 hour infusion of ISIS 2302 followed one week later by a two-week every-other-day regimen against a stable background of prednisone and cyclosporin A. Four patients each were assigned to the 0.05, 0.5, 1 and 2 mg/kg dose groups. All doses were well tolerated. There was no evidence of a pharmacological or pharmacokinetic interaction between ISIS 2302 and cyclosporin A. No patient experienced a rejection episode during or after treatment with ISIS 2302. As predicated, dose-related, transient increases in aPTT were observed, similar to those observed in normal volunteers at equivalent doses.

In the phase two study, four patients each are assigned to the 0.05, 0.1, 0.5 and 1 mg/kg dose groups, and 12 patients to the 2 mg/kg dose group. De novo renal transplant patients, recipients of cadaveric allografts, will be given 7 every-other-day infusions of ISIS 2302, beginning during the transplant procedure, in addition to their usual regimen of prednisone and cyclosporin A. Patients will be followed for 6 months post-transplantation to assess the incidence of acute rejection during this time period.

The incidence of acute rejection has been validated as an early surrogate for graft survival (Kahan, B. D., 1993, *Immunological Reviews*, 136, 29–49) and has served as the basis for approval of at least one drug, mycophenolate mofetil, for prevention of acute renal allograft rejection. Shanahan, W., 1998, *in Handbook of Experimental Pharmacology*, S. T. Crooke, ed., Springer-Verlag, Volume 131, 499–524. With standard therapy, consisting of prednisone, cyclosporine A ± azathioprine, the incidence of acute rejection within the first 3–6 months post-transplantation is a reliable 40–50%. It is believed that the addition of ISIS 2302 to the standard regimen will have a significant impact on the incidence of rejection, and hence graft survival, without unacceptable side effects.

What is claimed is:

1. An antisense oligonucleotide which is targeted to an mRNA encoding human intercellular adhesion molecule-1, and which inhibits the expression of said human intercellular adhesion molecule-1 with the proviso that the antisense oligonucleotide does not consist of SEQ ID NO: 84.

2. The antisense oligonucleotide of claim 1 which comprises at least one 2'-O-methoxyethyl modification.

3. The antisense oligonucleotide of claim 1 which has SEQ ID NO: 86, 87, 89, 91, 92, 93, 94, 95, 97, 98, 99, 100, 101, 102, 103 or 105.

4. A pharmaceutical composition comprising the antisense oligonucleotide of claim 3.

5. The pharmaceutical composition of claim 4 further comprising one or more of the following: saline, a colloidal dispersion system, a liposome, an emulsion, a cream or a penetration enhancer.

6. The pharmaceutical composition of claim 3 comprising SEQ ID NO: 22.

7. A method of modulating the synthesis of human intercellular adhesion molecule-1 comprising contacting a nucleic acid encoding said human intercellular adhesion molecule-1 with an antisense oligonucleotide of claim 1.

8. The method of claim 7 wherein said antisense oligonucleotide has SEQ ID NO: 22.

9. A method of treating an animal having a disease or condition selected from the group consisting of: inflammatory bowel disease, colitis, Crohn's disease, psoriasis, cytotoxic dermatitis, ulcerative colitis, and rheumatoid arthritis, comprising administering to said animal a prophylactic or therapeutic amount of the antisense oligonucleotide claim 1 whereby said disease or condition is prevented or treated.

10. The method of claim 9 wherein the antisense oligonucleotide is formulated in a pharmaceutical composition comprising one or more of the following: saline, a colloidal dispersion system, a liposome, an emulsion, a cream or a penetration enhancer.

11. The method of claim 9 wherein said animal is a human and the antisense oligonucleotide is targeted to human intercellular adhesion molecule-1.

12. The method of claim 11 wherein said disease or condition is a disease or condition of the skin.

13. The method of claim 12 wherein said disease or condition of the skin is psoriasis or cytotoxic dermatitis.

14. The method of claim 11 wherein said disease or condition is rheumatoid arthritis.

15. The method of claim 9 wherein said disease is pneumonia or multiple sclerosis.

16. The method of claim 11 wherein said antisense oligonucleotide has SEQ ID NO: 22.

17. The method of claim 9 wherein the disease or condition is an inflammatory disease or condition.

18. The method of claim 17 wherein said disease or condition is inflammatory bowel disease.

19. The method of claim 9 wherein said inflammatory bowel disease is Crohn's disease, colitis or ulcerative colitis.

20. A method of reducing corticosteroid use in a patient to whom corticosteroids are being administered or are likely to be administered comprising administering to said patient a therapeutically or prophylactically effective amount of an antisense oligonucleotide of claim 1.

21. The method of claim 20 wherein the patient has, is suspected of having or is prone to an inflammatory condition.

22. The method of claim 21 wherein the inflammatory condition is inflammatory bowel disease and the antisense oligonucleotide has SEQ ID NO: 22.

* * * * *

UNITED STATES PATENT AND TRADEMARK OFFICE
CERTIFICATE OF CORRECTION

PATENT NO. : 6,096,722
DATED : August 1, 2000
INVENTOR(S) : Bennett et al.

It is certified that error appears in the above-identified patent and that said Letters Patent is hereby corrected as shown below:

Title page,
Item [63], status of Application Serial No, 07/939,855 should be "pending".

Column 10,
Line 8, please delete "51" and insert -- 5' --.
Line 32, please delete "$CH_4$" and insert -- $CH_2$ --.

Column 18,
Line 8, please delete ":".

Column 19,
Line 7, please delete "Blaire®" and insert -- Blairex® --.

Column 22,
Line 48, please delete "ICAMI-1" and insert -- ICAM-1 --.

Column 27,
Line 3, please delete "Aamidites" and insert -- amidites --.

Column 28,
Line 54, please delete "tic" and insert -- tlc --.

Column 39,
Line 53, please delete "ICAMI-1" and insert -- ICAM-1 --.

Column 56,
Line 28, please delete "596" and insert -- 59% --.

Column 60,
Line 44, please delete "156" and insert -- 15% --.

Column 67,
Line 54, please delete "$^5Cr$" and insert -- $^{51}Cr$ --.

Column 68,
Line 31, please delete "26" and insert -- 2% --.

UNITED STATES PATENT AND TRADEMARK OFFICE
CERTIFICATE OF CORRECTION

PATENT NO. : 6,096,722
DATED : August 1, 2000
INVENTOR(S) : Bennett et al.

It is certified that error appears in the above-identified patent and that said Letters Patent is hereby corrected as shown below:

Column 113,
Line 29, please delete "claim 3" and insert -- claim 1 --.
Line 34, please delete "claim 3" and insert -- claim 4 --.

Signed and Sealed this

Fourteenth Day of May, 2002

Attest:

JAMES E. ROGAN
Attesting Officer  Director of the United States Patent and Trademark Office